US010973570B2

(12) United States Patent
Mathur et al.

(10) Patent No.: US 10,973,570 B2
(45) Date of Patent: Apr. 13, 2021

(54) APPARATUS AND METHOD FOR TREATMENT OF IN-STENT RESTENOSIS

(71) Applicant: Boston Scientific Scimed, Inc., Maple Grove, MN (US)

(72) Inventors: Prabodh Mathur, Laguna Niguel, CA (US); Meital Mazor, San Diego, CA (US); Dolores Perez, Escondido, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 259 days.

(21) Appl. No.: 15/586,040

(22) Filed: May 3, 2017

(65) Prior Publication Data

US 2017/0231694 A1 Aug. 17, 2017

Related U.S. Application Data

(63) Continuation of application No. 13/644,367, filed on Oct. 4, 2012, now Pat. No. 9,713,730.
(Continued)

(51) Int. Cl.
*A61B 18/14* (2006.01)
*A61B 18/00* (2006.01)
*A61B 18/12* (2006.01)

(52) U.S. Cl.
CPC .. *A61B 18/1492* (2013.01); *A61B 2018/0022* (2013.01); *A61B 2018/00267* (2013.01);
(Continued)

(58) Field of Classification Search
CPC ...... A61B 18/1492; A61B 2018/00023; A61B 2018/1465; A61B 2018/00267;
(Continued)

(56) References Cited

U.S. PATENT DOCUMENTS 6,319,242 B1 * 11/2001 Patterson ........... A61B 17/3207
604/508
2002/0016624 A1 2/2002 Patterson et al.
(Continued)

FOREIGN PATENT DOCUMENTS

JP H07-289557 A 11/1995

OTHER PUBLICATIONS

J. Nebeker et al., "Hypersensitivity Cases Associated With Drug-Eluting Coronary Stents: A Review of Available Cases From the Research on Adverse Drug Events and Reports (RADAR) Project", (2006), vol. 47, pp. 175-181.
(Continued)

*Primary Examiner* — Thomas A Giuliani
(74) *Attorney, Agent, or Firm* — Kacvinsky Daisak Bluni PLLC

(57) ABSTRACT

A catheter and catheter system can use energy tailored for remodeling and/or removal of target material proximate to a body lumen, often of stenotic material or tissue in the luminal wall of a blood vessel of a patient. An elongate flexible catheter body with a radially expendable structure may have a plurality of electrodes or other electrosurgical energy delivery surfaces to radically engage the luminal wall when the structure expands. Feedback using one or parameters of voltage, current, power, temperature, impedance magnitude, impedance phase angle, and frequency may be used to selectively control the delivery of energy.

18 Claims, 73 Drawing Sheets

Related U.S. Application Data

(60) Provisional application No. 61/542,949, filed on Oct. 4, 2011.

(52) U.S. Cl.
CPC ............ *A61B 2018/00404* (2013.01); *A61B 2018/00577* (2013.01); *A61B 2018/00642* (2013.01); *A61B 2018/00702* (2013.01); *A61B 2018/00714* (2013.01); *A61B 2018/00791* (2013.01); *A61B 2018/00827* (2013.01); *A61B 2018/00875* (2013.01); *A61B 2018/00892* (2013.01); *A61B 2018/124* (2013.01); *A61B 2018/1467* (2013.01)

(58) Field of Classification Search
CPC .. A61B 2018/0022; A61B 2018/00214; A61B 2018/00404; A61B 2018/00791; A61B 2018/00577; A61B 2018/124; A61B 2018/1467; A61B 2018/00702; A61B 2018/00714; A61B 2018/00642; A61N 1/18
USPC .......... 606/41, 42, 49, 50; 607/99, 102, 104, 607/113, 115, 116
See application file for complete search history.

(56) References Cited

U.S. PATENT DOCUMENTS

| | | |
|---|---|---|
| 2005/0096647 A1 | 5/2005 | Steinke et al. |
| 2006/0161246 A1 | 7/2006 | Rhim et al. |
| 2007/0038208 A1* | 2/2007 | Kefer ................. A61B 18/1233 606/34 |
| 2008/0125772 A1* | 5/2008 | Stone .................... A61M 25/10 606/41 |
| 2010/0034219 A1 | 2/2010 | Stadelmeier et al. |
| 2010/0168743 A1 | 7/2010 | Stone et al. |
| 2010/0204560 A1* | 8/2010 | Salahieh ............. A61B 5/0422 600/373 |
| 2011/0034912 A1 | 2/2011 | de Graff et al. |
| 2012/0095461 A1* | 4/2012 | Herscher ............ A61B 18/1492 606/45 |

OTHER PUBLICATIONS

Virmani et al., "Drug-eluting stents: caution and concerns for long-term outcome", (2004), vol. 15, pp. 313-318.

C. Brasselet et al., "Effect of local heating on restenosis and in-stent neointimal hyperplasia in the atherosclerotic rabbit model: a dose-ranging study", (2008), vol. 29, pp. 402-412.

* cited by examiner

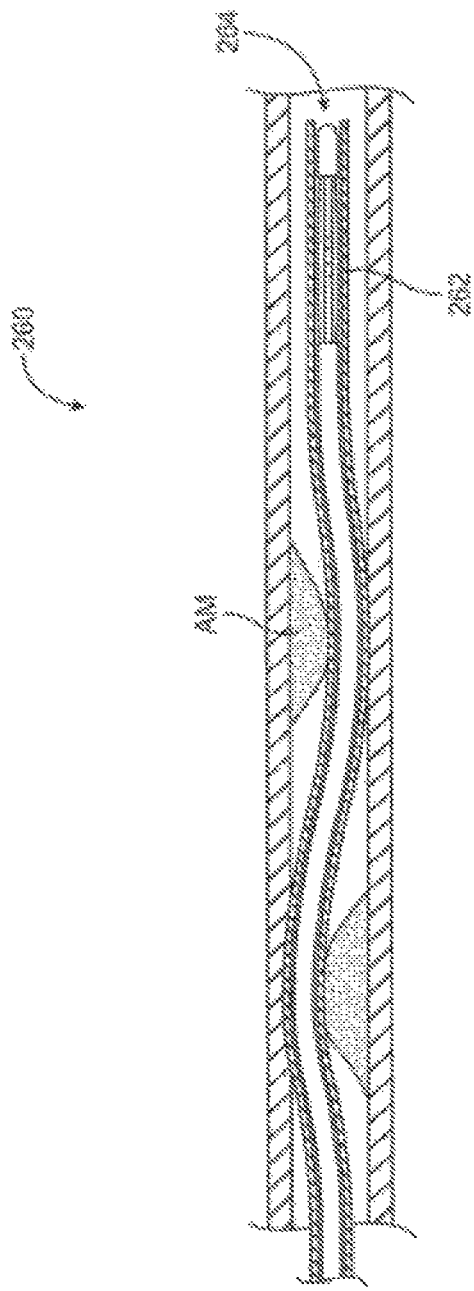

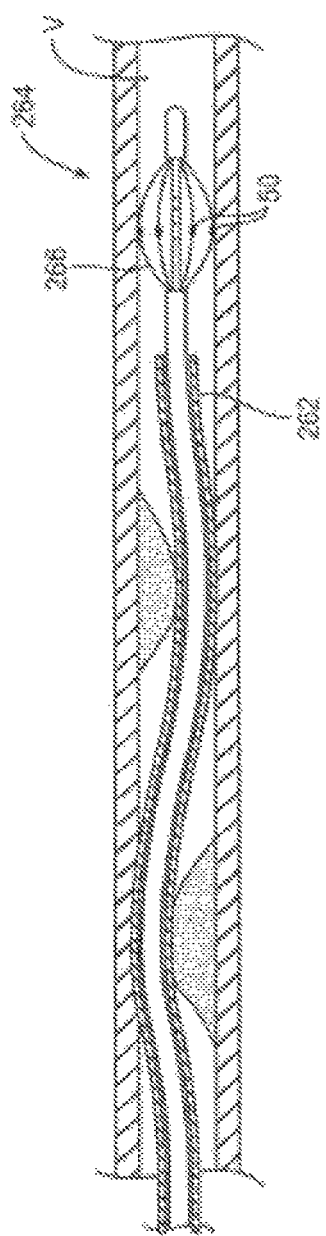

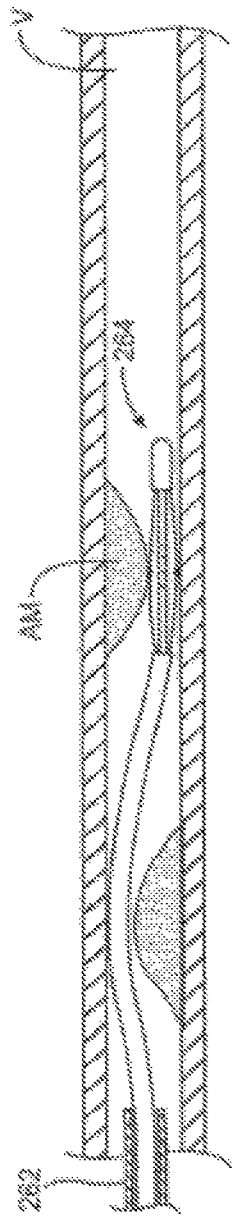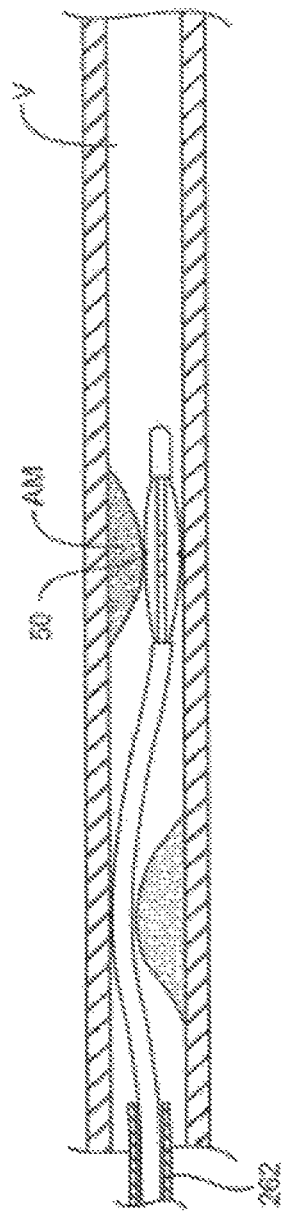

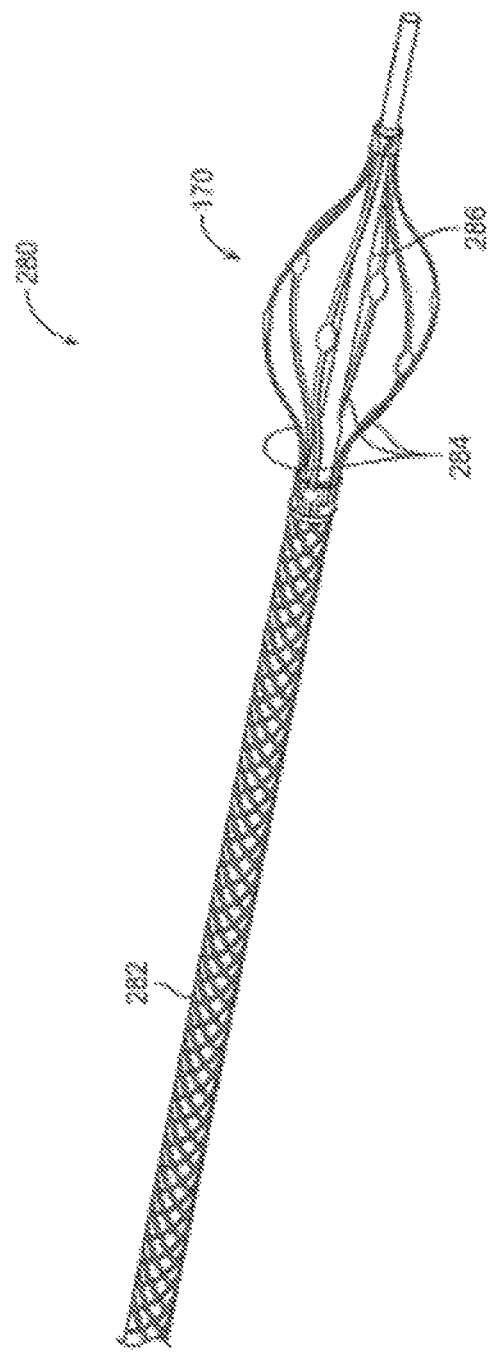

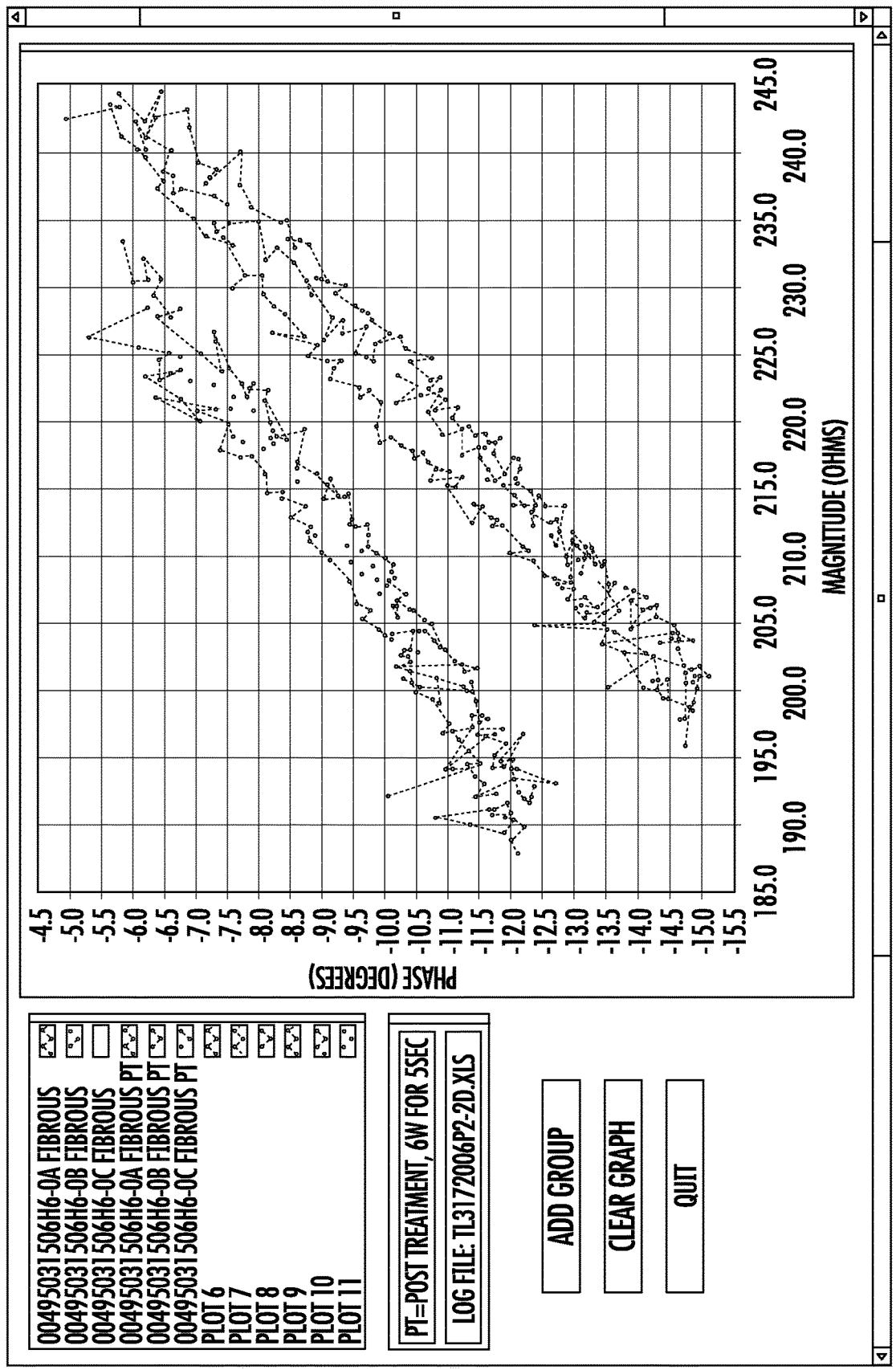
FIG. 3I1

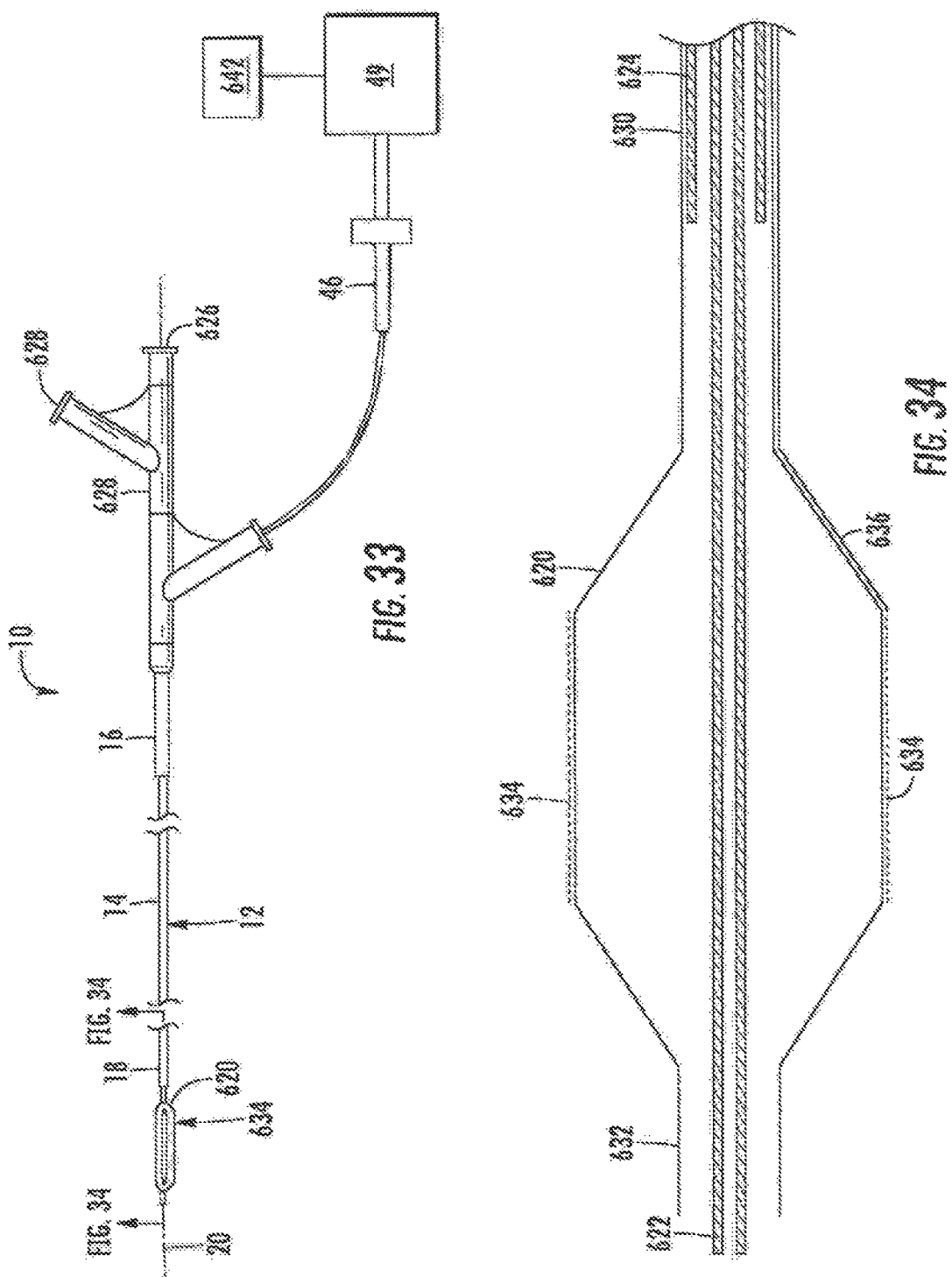

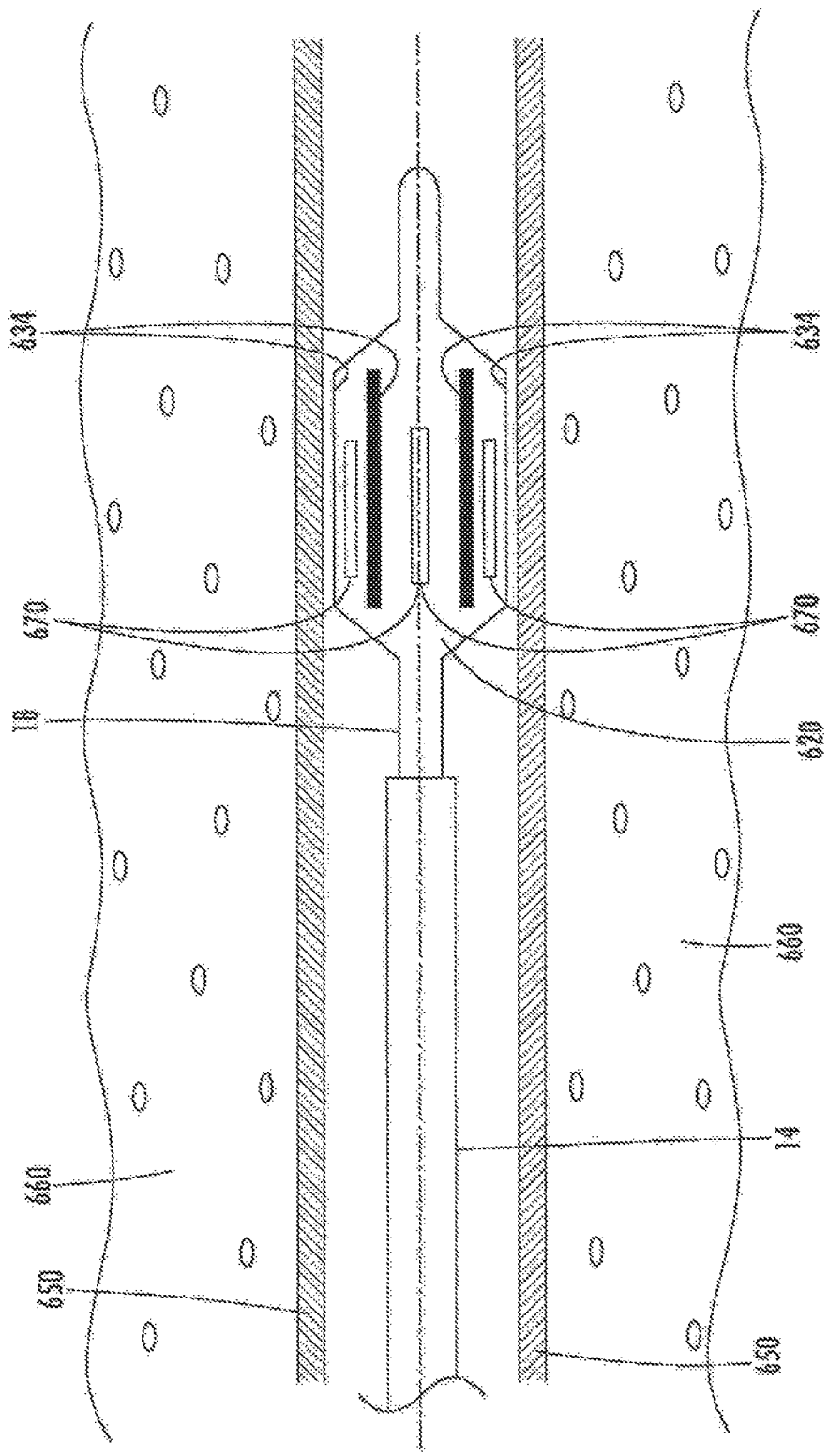

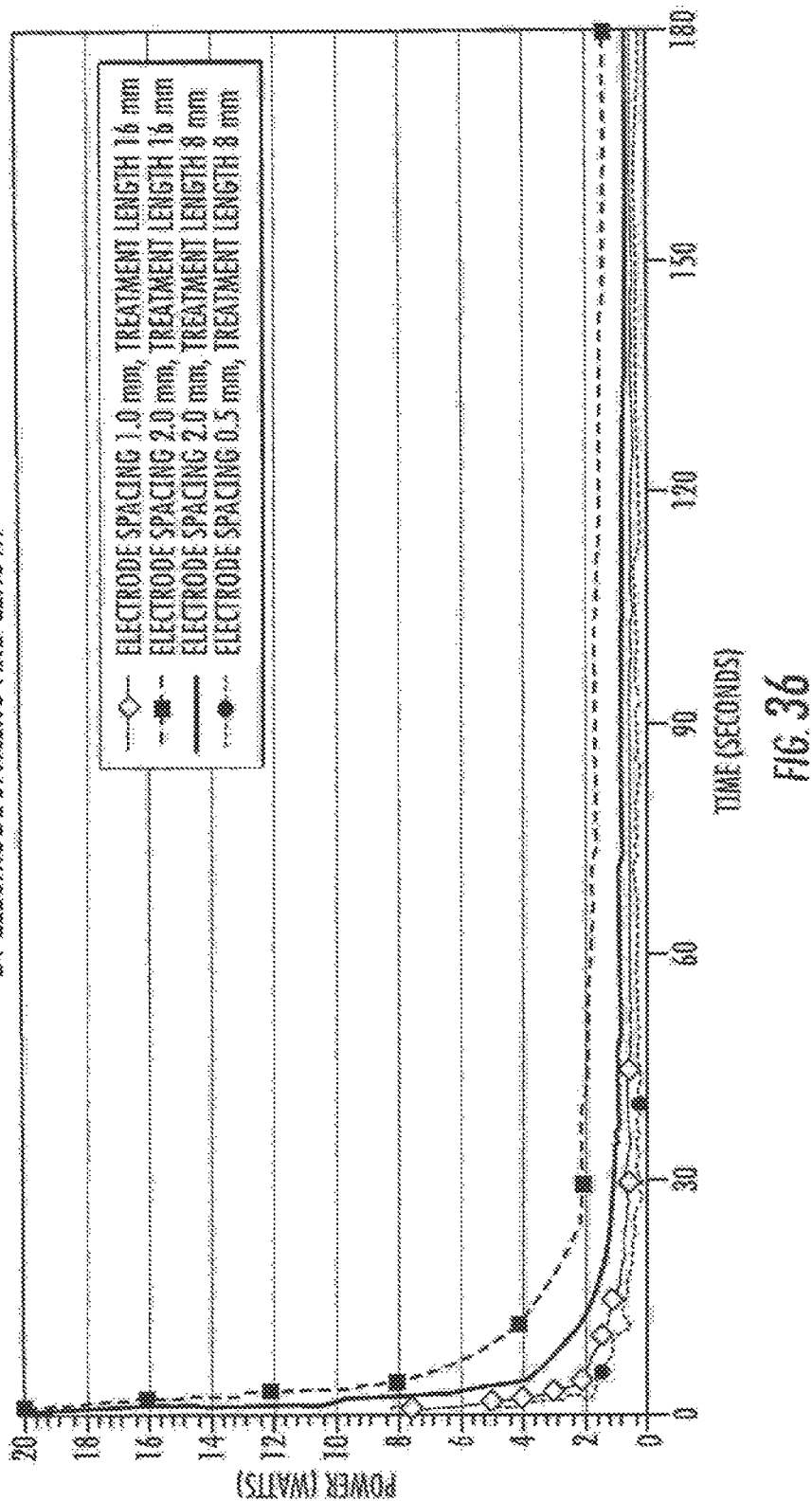

Dose #3: (4 Watts / 1 Seconds), 7 Day, 146f (4 Watts / 1 Second), 30 Day

Dose #4: (2 Watts / 4 Seconds),
7 Day, 145B (2 Watts / 4 Seconds), 30 Day, 145b (3 Watts / 2 Seconds), 30 Day

APPARATUS AND METHOD FOR TREATMENT OF IN-STENT RESTENOSIS

CROSS-REFERENCES TO RELATED APPLICATIONS

This application is a continuation of U.S. application Ser. No. 13/644,367, filed Oct. 4, 2012, now U.S. Pat. No. 9,713,730, which claims the benefit under 35 USC § 119(e) of U.S. Provisional Application No. 61/542,949, filed Oct. 4, 2011. The full disclosure of each of which is incorporated herein by reference in its their entirety for all purposes.

The present application is related to U.S. patent application Ser. No. 12/660,515 filed Feb. 2, 2010 (Allowed), entitled "Tuned RF Energy tor Selective Treatment of Atheroma and Other Target Tissues"; U.S. patent application Ser. No. 11/392,231 filed Mar. 28, 2006 (now U.S. Pat. No. 7,742,795); entitled "Tuned RF Energy for Selective Treatment of Atheroma and Other Target Tissues", the full, disclosures of which are incorporated herein by reference. The present application is related to U.S. patent application Ser. No. 10/338,138 filed on Sep. 10, 2004 (now U.S. Pat. No. 7,293,146), entitled "Selectable Eccentric Remodeling and/or Ablation of Atherosclerotic Material"; U.S. Provisional Application No, 60/852,787 filed on Oct. 18, 2006, entitled "Tuned RF Energy and Electrical Tissue Characterization For Selective Treatment Of Target Tissues"; U.S. Provisional Application No. 60/921,973 filed on Apr. 4, 2007, entitled "Tuned RF Energy and Electrical Tissue Characterization For Selective Treatment Of Target Tissues"; U.S. patent application Ser. No. 11/975,651 filed on Oct. 18, 2007, entitled "Tuned RF Energy and Electrical Tissue Characterization For Selective Treatment Of Target Tissues"; U.S. patent application Ser. No. 12/617,519 filed on Nov. 12, 2009 (Allowed), entitled "Selective Accumulation of Energy With or Without Knowledge of Tissue Topography"; U.S. patent application Ser. No. 11/975,474 filed on Oct. 18, 2007, entitled "Inducing Desirable Temperature Effects on Body Tissue"; U.S. patent application Ser. No. 11/975,383 filed on Oct. 18, 2007, entitled "System for Inducing Desirable Temperature Effects On Body Tissue"; U.S. patent application Ser. No. 12/616,720 filed on Nov. 13, 2009, entitled "Selective Drug Delivery in a Lumen"; U.S. application Ser. No. 12/564,268 filed on Sep. 22, 2009, entitled "Inducing Desirable Temperature Effects on Body Tissue Using Alternate Energy Sources"; and U.S. Provisional Application 61/177,744 filed on May 13, 2009, entitled "Directional Delivery of Energy and Bioactives", the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention is generally related to medical devices, systems, and methods. In exemplary embodiments, the invention provides catheter-based treatment for body tissues, which may further include treatment for luminal tissues, particularly for vascular stenosis and/or for delivery of energy proximate to a luminal wall. The methods, systems, and structures of the invention allow controlled delivery of tissue treatment energy, tissue remodeling and/or removal, often using both electrical diagnostic and/or control signals and electrosurgical energy.

Physicians use catheters to gain access to and repair interior tissues of the body, particularly within the lumens of the body such as blood vessels. A variety of means are known in the art for providing localized therapeutic effects in the area surrounding the target location. For example, balloon angioplasty, athetectomy, laser, cryogenic ablation, stents, and other catheter-based treatments of the like often are used to open arteries that have been narrowed due to disease.

Balloon angioplasty is often effective at opening a stenosed blood vessel, but the trauma associated with balloon dilation can impose significant injury, so that the benefits of balloon dilation may be limited in time. Stents are commonly used to extend the beneficial opening of the blood vessel.

Stenting, in conjunction with balloon dilation, is often the preferred treatment for stenotic disease such as atherosclerosis. In stenting, a collapsed metal framework is mounted on a balloon catheter that is introduced into the body. The stent is manipulated into the site of stenosis and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions.

Restenosis occurs when the treated vessel becomes re-blocked following its initial interventional treatment. It usually occurs within six months after the initial procedure. The mechanism of restenosis after balloon angioplasty is a combination of recoil, arterial vessel remodeling, and neointimal hyperplasia. Late lumen loss in stented segments is the result of intimal hyperplasia. Compared with balloon angioplasty alone, where the chance of restenosis may, for example, be estimated to be about 40%, stents have been shown to reduce the chance of restenosis in some cases to about 25%. Therefore, the majority of patients having angioplasty today are treated with stents. Restenosis can occur after the use of stents, and physicians refer to this as in-stent restenosis, which is typically seen three to six months after the stenting procedure. Several approaches have been developed to treat restenosis including ablation, atheroectomy, and drug eluting stents. In addition, work has also been initialed with systemic drug delivery (intravenous or oral) that may also improve procedural success rates. The existing available options for treatment of in-stent restenosis may have limitations such as procedural complexity, constraints caused by the pre-existing implant, limitations in long-term efficacy, extremely high product development costs and protracted regulatory pathways, costly medication regimens, and the challenges of vasclar biomechanics in places such as the leg.

In-stent restenosis involves the growth of new tissue within the arterial wall, and may be caused by a biological cascade mechanism of platelets, polymorphonuclear leucocytes, and macrophage aggregation leading to the migration of smooth muscle cells from the media to the intima coupled with smooth muscle cell proliferation at the intimal layer.

The acute onset of in-stent restenosis can begin with relocation of plaque and reorganization of thrombus, in conjunction with an acute inflammatory response to injury of the endothelium that promotes fibrin and platelet deposition. Leucocytes gather in and around the injury caused by balloon dilation and stent implantation. As the biological cascade continues, leucocyte recruitment is further sustained.

As the in-stent restenosis process continues, smooth muscle cells in the medial layer modify and migrate from the medial layer to the intimal layer before further proliferation as neointimal tissue. The volume of stenotic neointimal tissue is increased by smooth muscle cell synthesis of extracellular matrix predominantly comprised of proteoglycans and collagens.

None of the available interventional modalities provides optimal acute results, and long-term results can be poor. This is especially true for diffuse in-stent restenosis lesions, which are common. For example, treatment of a diffuse, long, coronary artery lesion with overlapping bare metal stents has been known to be associated with high rates of restenosis. By way of example, drug eluting stents were thought to be a revolutionary method of significant and sustained suppression of neointimal proliferation in cases of diffuse, long coronary lesions requiring overlapping stents. However, hypersensitivity reactions or cytotoxicity have been shown to be serious problems with stents coated with an antiproliferative drug. Nebeker, et al. have recently published data suggesting that the window of thrombotic risk associated with drug eluting stents extends far beyond that seen with bare metal stents, thus, post-operative anti-platelet therapy may be requisite for drug eluting stent patients (J Am Coll Cardiol (2006), 47: 175-181), the full contents of which are incorporated herein by reference. Furthermore, United States Food and Drug Administration reports and autopsy findings suggest that drug eluting stents may be a cause of systemic and intra-stent hypersensitivity reactions that, in some cases, have been associated with late thrombosis and death. This hypersensitivity or cytotoxicity, possibly induced by the coating comprising the drug carrier, is associated with delayed healing and poor endothelialization (Virmani, et al., Coron Artery Dis (2004), 15:313-318.), the full contents of which are incorporated herein by reference.

The application of energy to tissue has been shown to promote beneficial therapeutic responses, including for the treatment of tissue in or proximate to a body lumen. For example, thermal energy in controlled dosages may play a role in tissue debulking after thermal therapy by activation of Heat Shock Proteins (HSP's). HSP's are proteins that exist in most living cells (i.e. mammals, plants, and yeast). The often act like "chaperones" to ensure that a cell's normal functional proteins are in the right place at the right time. Their concentrations can increase in response to stress, such as heat, cold or lack of oxygen. Their increased presence can be a signal to the immune system for sick or necrotic cells that require removal, and therefore play a role in tissue debulking after a thermal treatment. Beneficial thermally-induced tissue effects have been disclosed by U.S. patent application Ser. No. 11/975,474 the full disclosure of which is incorporated herein by reference.

The application of energy to tissue proximate to an energy source is not limited to inducing tissue debulking. For example, radiofrequency energy may be used to affect energy conduction in nervous tissue in the fields of electrophysiology and neuromodulation; common examples include cardiac ablation to regulate heartbeat, neuromodulation to affect an expansive array of efferent and afferent nerve activity in physiologic processes such as those of the brain, digestive system, excretory processes, kidney and other organ function, sensory function, and the like.

In the example of thermal treatment of nerve tissue, such treatments may be ablative or non-ablative, wherein ablation causes long-term tissue damage while non-ablative energy may be in the form of stimulation or disruption of nerve conduction. The disruption of nerve conduction may be achieved by means that block or interfere with the transmission of nerve signals, which may for example be accomplished by means that change the nature of nerve tissue properties. The duration and extent of disruption may be tailored to the particular biologic process and may be a function of the energy dosage applied to the target site.

In the example of in-stent restenosis, a controlled application of radiofrequency energy may be used to cause resistive heating, and as a result the hydrogen bonds of the collagen contained in the tissue may be broken. This breaking of bonds may result in a more compliant stenosis that may be made to reshape around a balloon catheter while applying low pressure to the vessel wall (6 or less atmospheres) as opposed to the relatively high pressure (about 10-15 atmosphere) typical of regular balloon angioplasty. Thereby, this may facilitate restenotic tissue compression by the balloon and may result in a larger vessel lumen. In addition, Brasselet et al. have reported that moderate heating represents a promising approach to reduced neointimal hyperplasia by a mechanism involving decreased smooth muscle cell proliferation (Eur Heart J. (2008) 29(3):402-12), the full contents of which are incorporated herein by reference.

In light of the above, it would be advantageous to provide new devices, systems, and methods for diagnosing, characterizing, remodeling, and/or delivering therapeutic energy to tissue, which may further include stenosis of the lumens of the body, and particularly of the blood vessels. Specifically, it would be desirable to provide devices, systems, and methods for treating in-stent restenosis or energy delivery to other tissues proximate to a lumen where the delivery of energy in the form of a controlled dosage provides a means for interrupting biological activity. It would further be desirable to avoid significant cost or complexity while providing structures that could both characterize and remodel or remove target tissues such as plaques or other stenotic materials, nerve tissue, or other tissues such tissues found proximate to a lumen. It is further advantageous to avoid having to resort to the trauma known to be associated with dilation, excessive input of thermal energy to tissue, and the like, which may lead to chronic inflammatory response. It would also be beneficial if diagnosing and treating systems could provide some feedback on the progress of treatment.

BRIEF SUMMARY OF THE INVENTION

The present invention generally provides improved devices, systems, and methods for treating tissues proximate to a body lumen, including diseases of body lumens. Embodiments of the invention may allow treatment and/or analysis of the materials along these body lumens, optionally allowing target tissues such as nerve tissue, plaques, in-stent restenosis, or other lesions to be characterized using a variable frequency electrical power or signal source. Tissues may be locally treated by radially expanding an electrode array-supporting structure within (for example) a blood vessel. Further, circuits formed using selected electrodes of the array may be used for monitoring temperature and/or electrical characteristics (such as characteristic frequency, impedance phase angle, and impedance magnitude) of tissues along and adjacent to the blood vessel, so as to deliver a desired treatment to a targeted tissue region while avoiding significant thermal alteration of collateral tissues. Optionally, the same electrodes may be used to selectively (and often eccentrically) treat targeted tissues.

Embodiments of the invention may employ electrical energy to selectively heat target tissues and/or other body structures. For example, the electrical energy waveforms, application cycles, potentials, delivery systems, and the like may be tailored to help direct therapeutic energy into target tissues of the vasculature while inhibiting injury to collateral tissue structures. Tailoring may improve the efficacy of luminal therapies, may decrease collateral tissue damage, and in the case of in-stent restenosis, provide a means for delivering energy to stenotic material while avoiding electrical grounding caused by direct contact with an implanted stent.

For the treatment of in-stent restenosis, the ability to selectively energize electrodes based on temperature and/or electrical characteristics proximate to the points of an electrode array, in conjunction with monitoring changes in characteristics, may allow for a controlled delivery of energy. Furthermore, monitoring changes in electrical characteristics may provide the ability to halt energy delivery as an electrode comes into proximity or direct contact with the previously implanted stent while allowing energy delivery to continue in other circumferential locations where stenosis may remain present, until a substantially uniform recanalization of the restenosis occurs. Exemplary treatment systems and methods for physical targeting (for example, axial and/or radial targeting of occlusive tissues from within a blood vessel) and/or frequency targeting may make use of target tissue or disease localization information (for example, from intravascular imaging, or impedance measurement) and may optionally employ cooling to protect at least some tissues along a luminal wall.

In a first aspect the invention provides an energy delivery catheter system for energy delivery for such purposes as remodeling and/or reduction of material of, or adjacent to, body lumen of a patient. The system comprises an elongate flexible catheter body having a proximal end and a distal end with an axis there between. At least one energy delivers surface, preferably comprised to include an electrode, is disposed near the distal end. A power source is electrically coupled to the energy delivery surface(s). The power source energizes the energy delivery surface(s) with an electrical energy form that helps the energy heat the larger material while inhibiting collateral tissue damage.

In another aspect, the invention provides a method and system for analyzing a vessel wall of a blood vessel. The method comprises engaging the vessel wall with electrode of a probe (most preferably comprised of an expanding structure), and energizing the electrode with a variable frequency power source. The frequency of the power source is varied, and a target location of the vessel wall is characterized by monitoring a frequency-dependent characteristic of an electrical circuit. The electrical circuit comprises the power source, the electrode, and the engaged vessel wall. The system comprises a vascular probe having a proximal end, a distal end, and at least one electrode disposed near the distal end for engaging the vessel wall. A variable frequency power source may be coupled to the electrode such that when the electrode engages the vessel wall, an electrical circuit (including the power source, the electrode, and the engaged vessel wall) may be established. A processor may be coupled with the variable frequency power source, the processor configured to control energy delivery to one or more target treatment zones of the vessel wall by monitoring a frequency-dependent characteristic of the electrical circuit.

Optionally, the probe expands radially within the blood vessel so as to engage a plurality of electrodes against the vessel wall. The electrodes of the expanded probe may generally define a circumferentially distributed electrode array, and the electrodes of the array may be supported by the associated expandable structure of the probe. The expandable structure may comprise a balloon, or alternately an expandable basket having struts that may expand resiliently and independently within the blood vessel so as to couple the array to the vessel wall within non-circular lumens. An eccentric subset of the array, optionally a single electrode or a pair of electrodes adjacent the target tissue, may be energized to characterize tissues locally, and/or to eccentrically treat the characterized target tissue using a remodeling electrical potential. Feedback on the remodeling may be obtained by monitoring temperature and/or one or more characteristics of the electrical circuit while applying a variable-frequency signal, either during remodeling or by halting remodeling at least temporarily.

In exemplary embodiments, characterized target tissue may comprise a stenotic portion of a blood vessel, and the remodeling may be halted in response to temperature and/or the electrical characteristics of the circuit. For example, the remodeling may be halted in response to a change in a tissue signature signal, such as an impedance phase angle and magnitude at a selected frequency or range of frequencies, that may be related to a tissue temperature, actual or impending electrical contact with the metallic body of a stent, or the like. Target tissue may be characterized using tissue signature and/or tissue signature profiles, with the signature profiles comprising curves or sets of data representing a plurality of tissue signature measurements at different frequencies throughout a frequency range. The target tissue may be characterized by comparison of a measured tissue signature profile to at least one other tissue signature profile, and may allow for an eccentric selection of electrodes about the circumference of lumen. Some embodiments may allow differentiation between an implant or other inorganic object, targeted tissue and other tissues that have not been treated, optionally by checking changes of a subset of the tissue signature measurements of the signature profiles. Tissue signature profiles may be normalized and/or benchmarked to a known tissue of the patient (such as a health tissue identified using intravascular ultrasound or other known techniques). Target tissues may be characterized using relative slopes of tissue signature profiles or offsets between tissue signature profiles (and preferably both). The frequency range of the profiles will often extend below 50 KHz, typically extending from below about 50 KHz to over 1 MHz, and in some embodiments extending from about 4 Hz to about 2 MHz.

Many embodiments will be suitable for treating or characterizing a plurality of localized materials distributed about the blood vessel or proximate to the wall of the blood vessel at a depth as deep as 5 mm or more, and optionally for selectively treating the characterized materials with different remodeling treatments using the electrodes.

In many embodiments, gentle heating energy added before, during, and/or after dilation of a blood vessel may increase dilation effectiveness while lowering complications. Benefits of the heating may be enhanced (and/or complications inhibited) by limiting heating of the adventitial layer below a deleterious response threshold. In many cases, such heating of the intima and/or media may be provided using heating times of less than about 180 seconds, often being less than 60 seconds, and sometimes 10 seconds or less. Power may range from less than 0.5 Watts to 20 Watts or more. In some cases higher power may be used for shorter periods of time, while in other cases, very low power may be used for longer durations. Efficient coupling of the energy to the target tissue by matching the driving potential of the circuit to the target tissue phase angle may enhance desirable heating efficiency, effectively maximizing the area under the electrical power curve. The matching of the phase angle need not be absolute, and while complete phase matching to a characterized target tissue may have benefits, alternative systems may pre-set appropriate potentials to substantially match typical target tissues; though the actual phase angles may not be matched precisely, heating localization within the target tissues may be significantly better than using a standard power form.

In many embodiments, electrodes may be energized using closed loop control. Most typically the power generator may be controlled to vary voltage or electrode firing time such that a controlled output is held substantially constant; alternately current may be varied. Further, control loop parameters may be selected from one or more of power, impedance, impedance phase angle, and temperature. Power generation and control that may be used in combination with the embodiments described herein has been described by U.S. Patent Application 61/342,191, entitled "Power Generating and Control Apparatus for the Treatment of Tissue", the full disclosure of which is incorporated herein by reference.

In embodiments where power is used as a regulated parameter, voltage and current may be measured and voltage may be modulated to achieve a relatively constant power output within a tolerance according to a preset or defined power set point. Optionally the phase angle difference between voltage and current may be included in the power calculation to make power factor corrections based on the phase angle difference.

In embodiments where impedance is used as a regulated parameter, measured changes in impedance or impedance phase angle based on changes in tissue temperature and/or tissue state may be used to define a threshold at which power may be halted or allowed to continue where power is modulated to maintain the defined impedance or phase angle within a tolerance for a period of time.

In embodiments where temperature is used as a regulated parameter, a temperature sensor comprised of a thermocouple, thermistor, infrared sensor, or the like, may be used to measure temperature where a defined temperature or temperature range may be used in conjunction with power modulation to maintain temperature in proximity to the sensor within a temperature range. In some embodiments, a relatively uniform temperature in the region proximate to a powered electrode may be achieved by establishing a reference voltage and varying the firing time of one or more electrodes are fired to reach a temperature and then hold the temperature through the control of the duty cycle of the power to each electrode. Power control schemes may calculate the power requirements of the electrode having the greatest draw and then modulate firing time for electrodes having a lesser power draw over a given time interval (most often being small fractions of a second).

In some embodiments, more than one of voltage, current, impedance, and temperature may be used as closed loop control parameters. For example, current may be a closed loop control parameter where power is delivered in the proximity of highly conductive materials, such as metallic stents. In this case it may be prudent to limit current, such as by stopping power delivery when the impedance is at or below a given level. Or, in the case of a power-limited control algorithm (which will increase current when impedance drops) one may additionally limit the maximum current that is delivered at or below a given impedance level. This method has the effect of reducing power as impedance falls below a given threshold. Optionally, some embodiments may employ one or both of pulse width modulation of energy, and amplitude modulation of energy as a means of control.

In embodiments where energy is delivered to a plurality of electrodes at the same time, electrodes may be powered and controlled either by separate, independent circuits having their own control loops, or by firing these electrodes sequentially. Electrodes may be fired simultaneously, in subgroups fired in sequence, in combinations, or individually in any sequence. For instance, electrode combinations may be chosen so as to minimize the space between treatment zones, where treatment zones may be defined by the tissue volume between paired electrodes. For example, an in-stent restenosis may require energy delivery around the full circumference of a lumen but the open portion of the lumen may not be concentric with the natural center of the healthy vessel. In this circumstance, individual pairs of bipolar electrodes may be energized and controlled until a desired temperature is reached or until proximity to the implanted stent is reached. Electrode pairs may optionally be selected again, so as to fill in the gaps between the first tissue treatment zones, and the controlled delivery of energy may be repeated such that essentially the full circumference of the lumen receives treatment. In a preferred embodiment for treating in-stent restenosis, electrode pairs are energized sequentially to create a first pattern of treatment zones. Electrode pairs next to be energized are then indexed so as to create a second pattern of treatment zones, with at least some degree of overlap with the first treatment zones, and then energized sequentially to complete the energy treatment dosage to be used.

Tissue treatment may involve the application of energy, typically in the form of radiofrequency, microwave and/or ultrasound energy to electrodes. This energy will be controlled so as to limit a temperature of target and/or collateral tissues proximate to a luminal wall, for example, so as to limit the heating of an in-stent restenosis of the intimal layer of an artery structure. In some embodiments, the surface temperature range is from about 50° C. to about 90° C. For gentle healing, the surface temperature may range from about 50° C. to about 75° C. while for more aggressive heating, the surface temperature may range from about 75° C. to about 90° C. Limiting heating of a target tissue to less than a surface temperature in a range from about 50° C. to about 75° C., such that the bulk tissue temperature remains mostly below 50° C.-55° C., may inhibit an immune response that might otherwise lead to stenosis. For example, relatively mild surface temperatures between about 50° C. and about 75° C., and most preferably between about 50° C. and about 65° C. may be sufficient to denature and break protein bonds during treatment, immediately after treatment, and/or more than one hour, more than one day, more than one week, or even more than one month after the treatment through a healing response of the tissue to she treatment so as to provide a bigger vessel lumen and improved blood flow.

BRIEF DESCRIPTION OF THE DRAWINGS

FIGS. 14A-E are cross sectional side views through a body lumen showing additional aspects of treatment methods and devices described herein.

FIG. 16 is a perspective view of an exemplary catheter assembly.

FIG. 33 schematically illustrates an alternate embodiment of the system of FIG. 2, wherein the expanding structure comprises a balloon.

FIG. 33A schematically illustrates the system of FIG. 33 positioned to deliver energy to tissues proximate to a body lumen.

FIG. 34 is a sectional view of the balloon of FIG. 33.

FIG. 36 illustrates relationships between energy delivery and electrode spacing for the systems of FIGS. 2 and 33.

DETAILED DESCRIPTION OF THE INVENTION

Figure 1A:
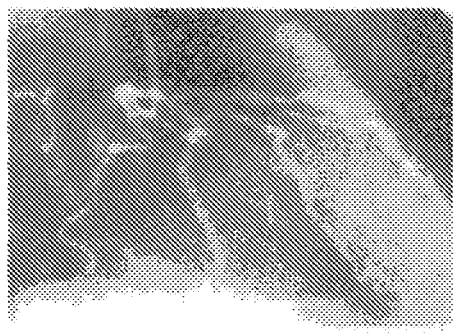
FIG. 1A illustrates diffuse atherosclerotic disease in which a substantial length of multiple blood vessels has limited effective diameters.

The present invention provides devices, systems, and methods to treat and/or analyze luminal tissue or tissues proximate to a lumen. The anatomical structure into which the catheter is placed may be, for example, the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the kidney, the liver, the ureter, the ejaculatory duct, the vas deferens, the urethra, the uterine cavity, the vaginal canal, and the cervical canal. The invention will be particularly useful for characterizing and treating materials along an artery, such as to open the artery lumen and increase blood flow, further including stenosis developed as a result of prior stent implantation. Remodeling may involve the application of electrosurgical energy, typically in the form of radiofrequency, laser, microwave, or ultrasound energy potentials to energy delivery surfaces such as electrodes, antennas, and other such energy delivery structures. This energy will preferably be controlled so as to limit a temperature of target and/or collateral tissues, for example, limiting the heating of healthy tissue collateral to the target tissue. In many embodiments, the energy will be controlled to limit the maximum temperature of an outer layer or adventitia of the blood vessel to no more than about 65° C. Inhibiting heating of non-target tissues (such as an intimal layer adjacent to an in-stent restenosis) may inhibit an immune response that might otherwise lead to further restenosis. Many embodiments may apply sufficient energy to target tissues to cause heating to as much as about 85° C. or more while inhibiting collateral damage through selective application of heating energy. Relatively mild heating energies may be sufficient to denature and shrink stenotic material during treatment, immediately after treatment, and/or more than one hour or even more than one month after the treatment through a healing response to the treatment so as to provide a bigger vessel lumen and improved blood flow.

Smooth muscle contraction may be avoided, without actually killing or ablating it, by heating the smooth muscle to 47-48° C. The actin and myosin proteins become denatured but vital oxidative metabolic enzymes remain intact. This can promote luminal dilation or at minimum, prevent construction (i.e. angioplasty balloon expansion vessel recoil or vasospasms often linked as a contributor to acute anginal attacks). Also, thermal energy must be low enough to prevent "thermal fixation", where tissue is "fixed" analogous to formalin fixation that prevents a desired immune-system-activated tissue debulking. As a general guide to tissue-temperature effects, below is a list of tissue temperature correlations that fall within the 2-10 second duration range at a given temperature:

42° C.=protein denaturation
41°-44° C.=DNA susceptibility
43° C.=spontaneous depolarizations
45° C.=mitochondrial breakdown
47.5° C.=contractile protein breakdown
48° C.=depolarization incapable
50° C.=blood cells become amorphous
50° C.=intracellular toxicity
50° C.=irreversible cell death
>50° C.=oncosis Inducing a therapeutic temperature with radiofrequency energy for even a second can result in a longer duration of elevated temperatures due to the build-up heat that continues to thermally diffuse into surrounding tissue. Irreversible cell death temperatures are suggested above but in reality comprise a wide range of temperatures capable of such effect. These temperatures can mathematically be described by a "line-fit" algorithm of y=0.011x+55.01, whereas the y-axis is temperature in (° C.) and the x-axis is in time in (sec). This demonstrates irreversible cell death as a relationship of temperature vs. time with the above described slope starting from 55° C. at 1 second to 45° C. at 1000 seconds. At temperatures higher than 55° C., time for cell death is too short to be effectively measured, and below 45° C. the time required is too long to be useful. Excessive or uncontrolled application of tissue temperatures above 60° C. become capable of immediate tissue debulking but may render healthy vessel tissue stenosed, charred, perforated or vaporized. Examples of these tissue-temperature effects are:

72°-86° C.=type 1 collagen breakdown
85° C.=blood coagulation/clumping
82-96° C.=type 3 collagen breakdown
100° C.=intracellular/interstitial fluid phase change–"popping">100° C.=tissue desiccation
100°-200° C.=tissue glucose sticks to electrode
>200° C.=rapid vaporization/cell explosions (cutting), carbonization Thermal therapy may cause the activation of heat shock proteins that aid in tissue debulking. Heat shock proteins exist in most living cells to ensure that a cell's normal functional proteins are in the right place at the right time. Their concentrations can increase in response to stress, such as heat, cold, or lack of oxygen. Their increased presence can be a signal to the immune system for the presence of sick or necrotic cells that require removal, and therefore play a role in tissue debulking after a thermal treatment. A controlled delivery of energy that activates heat shock proteins, but that avoids applying energy sufficient to cause undesirable tissue damage, may provide an effective means for delivering therapeutic effects for tissues proximate to a luminal wall. This biological response may be particularly advantageous for the treatment of in-stent restenosis where an acute response to thermal energy may be used to debulk hyperplastic stenotic tissue growth, that itself was the product of a chronic inflammatory response to dilation and or the presence of a stent while avoiding thermal damage that may result in further restenosis. Hence, energy treatment of tissues proximate to a lumen may comprise gentle heating, removal, denaturing, shrinkage, melting, and the like, of the target tissues. Optionally, targeted material within the layers of an artery may be denatured so as to improve blood flow or to interrupt biological functioning while avoiding the generation of debris or lesions that may subsequently cause occlusion due to tissue damage. A bipolar electrode configuration is the most preferred method of implementation in order to better control the flow of energy to selectively treat tissue proximate to the luminal wall.

Embodiments of the present invention will often provide electrosurgical capabilities, sensing or imaging suitable for measuring stenosis, atheroma and/or vascular walls. As stenosis may be eccentric relative to an axis of the blood vessel over 50% of the time, possibly in as much as (or even more than) 75% of cases. The devices and methods of the present invention will often be particularly well suited for directing treatment eccentrically, often in response to circumferential detecting or imaging of the material proximate to the lumen. While the methods and devices described herein allow such eccentric treatments, the devices may also be used for treatment of radially symmetric lumens or tissues by selectively directing energy in a radially symmetric pattern.

While the present invention may be used in combination with stenting and/or balloon dilation, it is particularly well suited for increasing the open diameter of blood vessels in which stenting and balloon angioplasty are know to have limitations, such as treatment of in-stent restenosis, and diffuse disease, in which stenosis is spread along a significant length of an artery rather than being localized in one area. The present invention may also provide advantages in treatment of tissues proximate to, but, not located on the surface of a luminal wall, for example, tissue at a depth of as much as 5 mm or more. The invention may also find advantageous use for treatment of tortuous, sharply-curved vessels, as no stent need be advanced into or expanded within the sharp bends of such blood vessels; this may further include the arteries of the leg where prior stenting has been complicated by implant fracture, persistent diffuse disease, or vessel tortuosity. Still further advantageous applications include treatment along bifurcations (where side branch blockage may be an issue) and in the peripheral extremities such as the legs, feet, and arms where implants may not reach due to size limitations, or other factors that prevent use of stents.

Embodiments of the invention may measure impedance of a circuit, and particularly of a circuit that includes an electrode coupled with a luminal wall or other tissue. Such impedance measurements of alternating current (AC) circuits may often include a measurement of both a real portion or magnitude of the impedance, and an imaginary portion or phase angle of the impedance. The impedance magnitude and phase angle generated at an appropriate frequency by a tissue coupled to the electrode may provide a tissue signature. To enhance the accuracy of tissue signature measurements, a plurality of individual measurements (often three or more) may be taken and averaged. By measuring tissue signatures at a plurality of different frequencies within a frequency range, a signature profile forth tissue may be generated, with the signature profiles optionally comprising a curve or curve-fit of phase angles and magnitudes throughout a frequency range. For example, measurement may be taken at one frequency, or as few as 2 different frequencies, or as many as 100 or more different frequencies. In some embodiments, tissue signature measurements may be compared, and/or a smaller number (2-10 or 5-50) of such measurements may be included in a tissue signature profile. Tissue signature measurements may depend on the measurement conditions (including the configuration of the electrodes/tissue coupling), particularly when the measurements are performed by transmitting bipolar tissue sensing current between two electrodes that are supported by a radially expandable support structure. Nonetheless, the relative tissue signatures and/or signature profiles of different tissues of different patients, particularly the relative offsets and/or the relative slopes, will often be sufficiently consistent to allow the tissue signatures and signature profiles to be used to distinguish between one or more of implant surfaces, target tissue, tissue proximate to the electrodes.

The present invention may additionally take advantage of the differences in tissue properties, if one tissue has a better thermal conductivity (k) than another type of tissue, it will conduct heat away more rapidly. If one tissue has a lower specific heat capacity (cp) than another type of tissue, its temperature will increase more given the same amount of energy applied to the same mass (and volume, assuming relatively similar tissue density). If one type of tissue has denser vasculature, or is reliably in closer proximity to well-perfused areas, it will conduct heat away more rapidly.

Optionally, baseline measurements of tissues, which may be characterized via intravascular ultrasound, optical coherence tomography, etc., may be taken to help differentiate adjacent tissues, as the tissue signatures and/or signature profiles may differ from person to person. Additionally, the tissue signatures and/or signature profile curves may be normalized to facilitate identification of the relevant slopes, offsets, etc., between different tissues. Once sufficient frequency and profile correlations have been established between tissue signatures, and the profiles of different tissues for a number of different patients and measurement conditions, tissue characterization of at least some patients may be provided without having to resort to other baseline tissue characterization methodologies. Correlations may include any of impedance magnitude, phase angle, including the relative slopes and/or offsets thereof.

Figure 1B:
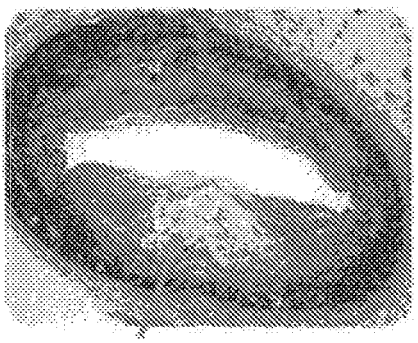
FIG. 1B illustrates vulnerable plaque within a blood vessel.
Figure 1C:
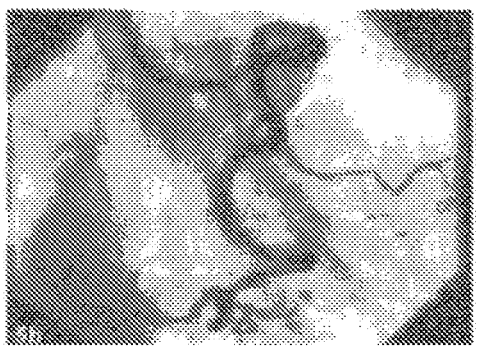
FIG. 1C illustrates the sharp bends or tortuosity of some blood vessels.
Figure 1D:
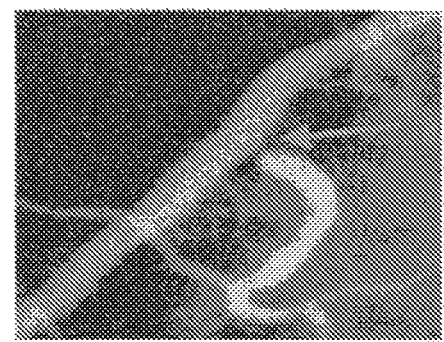
FIG. 1D illustrates atherosclerotic disease at a bifurcation.
Figure 1E:
FIG. 1E illustrates a lesion associated with anterosclerotic disease of the extremities.
Figure 1F:
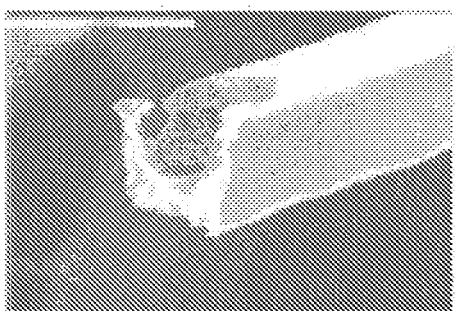
FIG. 1F is an illustration of a stent fracture or corrosion.

Diffuse disease and vulnerable plaque are illustrated in FIGS. 1A and 1B, respectively. FIG. 1C illustrates vascular that can result from atherosclerotic disease of the extremities. FIG. 1F illustrates a stent structural member fracture which may result in eventual restenosis of the artery.

Figure 1G:
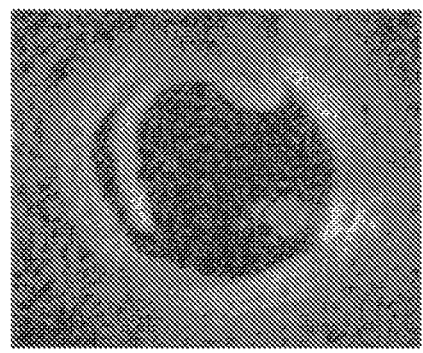
FIG. 1G illustrates a dissection within a blood vessel.
Figure 1H:
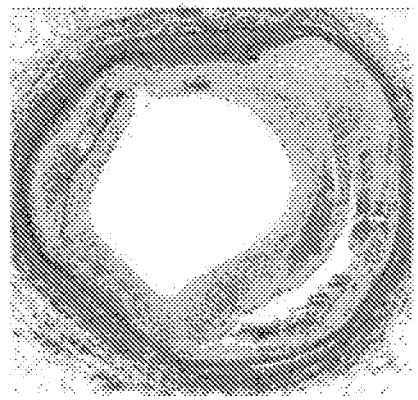
FIG. 1H illustrates a circumferential measurement of an artery wall around a healthy artery.
Figure 1I:
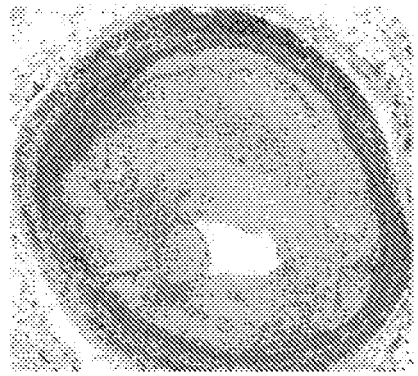
FIG. 1I illustrates circumferential distribution of atheroma about a restenosed artery.

Arterial dissection and restenosis may be understood with reference to FIGS. 1G through 1I. The artery comprises three layers: an endothelial layer, a medial layer, and adventitial layer. During angioplasty, the inside layer may delaminate or detach partially from the wall so as to form a dissection as illustrated in FIG. 1G. Such dissections divert and may obstruct blood flow. As can be understood by comparing FIGS. 1H and 1I, angioplasty is a relatively aggressive procedure which may injure the tissue of the blood vessel. In response to this injury, the presence of a stent, and/or in the continuing progression of the original atherosclerotic disease, the opened artery may restenose or subsequently decrease in diameter as illustrated in FIG. 1I.

In general, the present invention provides a catheter that is relatively quick and easy to use by the physician. The catheter system of the present invention may allow arteries to be opened to a significant percentage of their nominal or native artery diameter. In some embodiments, arteries may be opened to as much as about 85%, while acute openings may be less than 85%. Rapid stenosis reduction may be effected using sufficient power to heat tissues locally to temperatures ranging from about 50° C. to about 65° C. using gentle heating.

Alternatively, a milder treatment may be implemented, for example, providing a lumen of about 50% native diameter when treatment is complete, but that may still provide as much as 80% or more of native vessel open diameters after a subsequent healing process is complete (see Table 3). Resorption of treated luminal tissues is a preferred biological response by the targeted tissue treatment areas. Some embodiments may heat at least some stenotic tissue to a temperature in a range from about 55° C. to about 80° C. Higher temperatures up to about 100° C. could be used for the purpose of the tissue treatment.

In other embodiments, heating may be controlled so as to provide tissue temperatures in a range between about 50° C. and about 65° C., with some embodiments benefiting from maximum tissue temperatures of about 63° C. Advantageously, the systems and methods of the present invention may be used below the balloon dilation pressures typically associated with balloon angioplasty (6 atmospheres or less as opposed to 10 or more atmospheres), thereby avoiding dissections and dilation-based tissue injury known to chronically result in restenosis. Optionally, treatments of tissues may be repeated during a single surgical session, or after a month or more (even after a year or more) to provide or maintain a desired opening of the lumen.

To keep surface temperatures of the tissue in a range from about 50° C. to about 65° C., power is applied to treatment zones (tissue between electrode pairs) using combinations of power and time that are chosen to derive the desired tissue response. Table 1 shows sample results of experimental testing done on a cadaver aorta using various electrode energy settings and surface temperatures achieved versus time. By ranging the average power between 1 and 5 Watts for between 0.5 and 10 seconds, the surface temperature reached was between 50° C. and 65° C. Trial doses are shown below in Table 1.

TABLE 1

| Approx. Power | Average Time | Surface Temp |
| --- | --- | --- |
| 1 Watt | 8 sec | 50° C. |
| 2 Watt | 2 sec | 50° C. |
| 3 Watt | 1.3 sec | 50° C. |
| 4 Watt | 1 sec | 50° C. |
| 5 Watt | 5 sec | 50° C. |
| 2 Watt | 4 sec | 60° C. |
| 3 Watt | 2 sec | 60° C. |

TABLE 1-continued

| Approx. Power | Average Time | Surface Temp |
| --- | --- | --- |
| 4 Watt | 1.5 sec | 60° C. |
| 5 Watt | 1 sec | 60° C. |
| 3 Watt | 3 sec | 65° C. |
| 4 Watt | 2 sec | 65° C. |

Regarding the length and spacing of the electrodes within a particular pair, these factors are inter-related with power and impedance. As the length of the electrodes, decreases, the impedance seen by the generator will go up, but the volume of tissue will go down, so that the power setting on the generator may be decreased. As the gap between the electrodes widens, the impedance seen by the generator will also go up, but the volume of tissue will go up as well, so that the power setting on the generator should be increased. Hence, there are roughly opposed effects on load impedance when decreasing electrode length and increasing electrode spacing.

Desired power, energy, and time of the treatment are likewise inter-related, and may also be at least related with electrode geometry. Speaking very generally, lower power treatments applied for long times tends to result in treatments with relatively higher total energies, while higher power treatments for shorter times tends to result in lower energy treatments. If the electrode spacing were doubled, power may increase by four times. The power transmitted into the tissue can be calibrated and scaled to the particular electrode configuration, often in order to keep the power and energy density in a desirable range.

Power settings may be scaled by varying the electrode configuration. If, for instance, the inner edge-to-edge spacing of the electrodes were doubled, roughly 4 times the power may be applied because the volume of tissue becomes roughly 4 times larger. As such, an electrode configuration that is somewhat different from the exemplary embodiments described herein could be used within a power range of roughly 4 to 20 Watts. Shortening the electrodes, and thus shortening and reducing the volume of the remodeling zones, would also affect the magnitude of the power that may be applied to the tissue volume.

Referring to FIG. 36, in order to quantify this complex set of relationships, and bound the preferred space within which the exemplary treatment device operates, an empirical relationship between safe values of several of these parameters may be generated and provided graphically, in table form, or by a mathematical relationships. An exemplary equation describing a particularly advantageous relationship is: power=$b*x^2*L*(t^{-0.59})$, where b is a parameter in the range of 0.2 to 0.6, x is the inner edge-to-edge spacing of the electrodes in millimeters, L is the length of the electrodes in millimeters (and also the approximate length of the remodeling zone), the power is in Watts, and t is time in seconds, b has units of Watts/(mm^3)*(seconds^0.59). Exemplary treatments in the range described by this equation include treatments such as 4 Watts for 2 seconds, 3 Watts for 3 seconds, 2 Watts for 4 seconds, and 1 Watt for 12 seconds using the exemplary electrode geometries described herein. Additional, very low power and long duration treatments such as 0.25 Watts for 180 seconds are including in this relationship. Alternative suitable treatment ranges fall within or near the set of curves shown in FIG. 36, which shows approximate numbers for maximum power and time by electrode dimensions. Still further alternative treatment parameter values can be understood with reference to Table 2, which shows total energies for different combinations of power and time for a few different electrode pair geometries.

TABLE 2

| Exemplary Peripheral Treatment Catheter | | | Alternative I Peripheral Treatment Catheter | | | Alternative II Peripheral Treatment Catheter | | | Exemplary Coronary Treatment Catheter | | |
|---|---|---|---|---|---|---|---|---|---|---|---|
| X = 1 mm, L = 16 mm | | Total | X = 2 mm, L = 16 mm | | Total | X = 2 mm, L = 8 mm | | Total | X = 0.5 mm, L = 8 mm | | Total |
| Time (s) | Power (W) | Energy (J) | Time (s) | Power (W) | Energy (J) | Time (s) | Power (W) | Energy (J) | Time (s) | Power (W) | Energy (J) |
| 1 | 5 | 5 | 1 | 20 | 20 | 1 | 10 | 10 | 1 | 0.625 | 0.625 |
| 2 | 4 | 8 | 2 | 16 | 32 | 2 | 8 | 16 | 2 | 0.5 | 1 |
| 3 | 3 | 9 | 3 | 12 | 36 | 3 | 6 | 18 | 3 | 0.375 | 1.125 |
| 4 | 2 | 8 | 4 | 8 | 32 | 4 | 4 | 16 | 4 | 0.25 | 1 |
| 12 | 1 | 12 | 12 | 4 | 48 | 12 | 2 | 24 | 12 | 0.125 | 1.5 |
| 30 | 0.5 | 15 | 30 | 2 | 60 | 30 | 1 | 30 | 30 | 0.0625 | 1.875 |
| 180 | 0.25 | 45 | 180 | 1 | 180 | 180 | 0.5 | 90 | 180 | 0.03125 | 5.625 |

Figure 2:
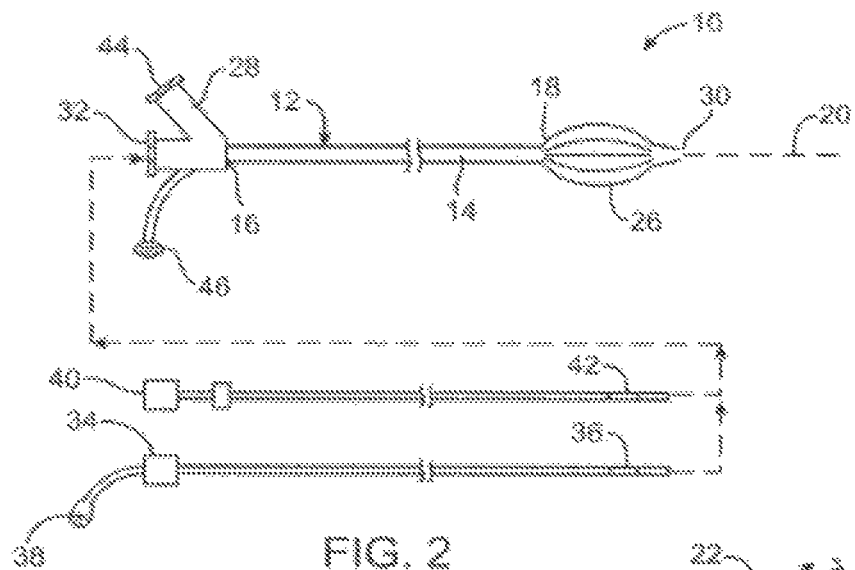
FIG. 2 schematically illustrates an energy delivery catheter system according to the present invention.
Figure 3:
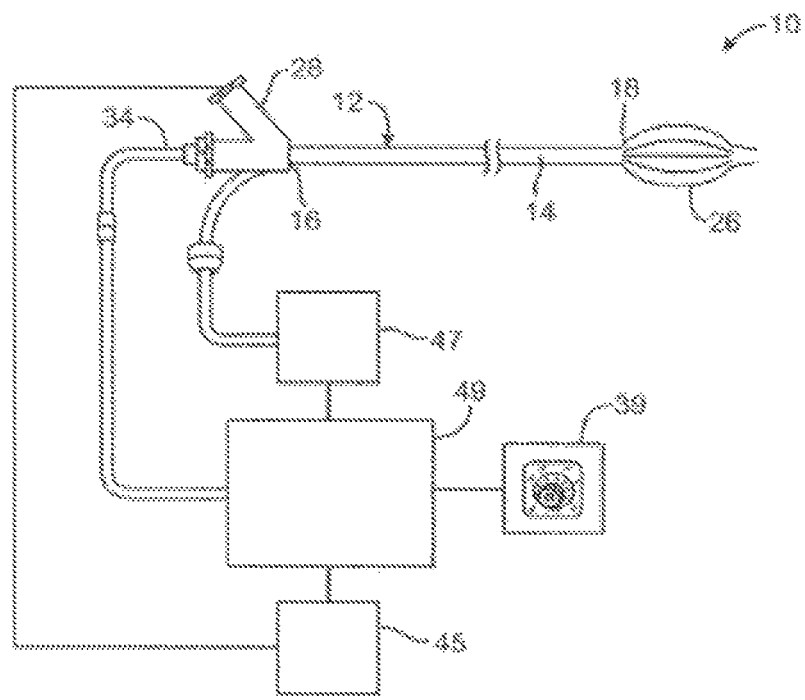
FIG. 3 schematically illustrates a catheter system for remodeling atherosclerotic material, the system including the catheter of FIG. 2.

An exemplary catheter system 10 is schematically illustrated in FIGS. 2 and 3. An energy delivery catheter 12 includes a catheter body 14 having a proximal end 16 and a distal end 18. Catheter body 14 is flexible and defines a catheter axis 20, and includes an aspiration lumen 22 and an irrigation lumen 24 (see FIG. 3). Still further lumens may be provided for a guidewire, imaging system, or the like as described below. Lumen 22 may be used for sensing and/or imaging as well as aspiration.

Catheter 12 includes a radially expandable structure 26 adjacent distal end 18 and a housing 28 adjacent proximal end 16. A distal tip 30 may include an integral tip valve to seal aspiration lumen 22 and allow passage of guidewires, imaging, and the like.

Proximal housing 28 includes a first connector 32 in fluid communication with aspiration lumen 22. Aspiration lumen 22 may have an aspiration port within expandable structure 26 so as to allow aspiration or aspiration of debris and gasses from within the expandable structure. Aspiration lumen 22 may also be used as an access lumen for guidewires, intravascular imaging catheters, and/or distally advancing intravascular radiation treatment catheters or restenosis inhibiting drugs. Hence, connector 32 may selectively accommodate an imaging catheter 34 having an atherosclerotic material detector 36 advanceable within catheter body 14 adjacent to and/or beyond distal end 18, the detector often comprising an intravascular ultrasound transducer, an optical coherent tomography sensor, an MRI antenna, or the like. An imaging connector 38 of imaging catheter 34 transmits imaging signals allowing circumferential measurement of atherosclerotic thicknesses about axis 20 to a display 39.

Optionally, connector 32 also accommodates a restenosis inhibiting treatment catheter 40, the treatment catheter here comprising an intravascular radiation catheter. Such a radiation catheter may include a radiation source 42 which can again be advanced distally within catheter body 14 to or beyond expandable structure 26.

Figure 4:
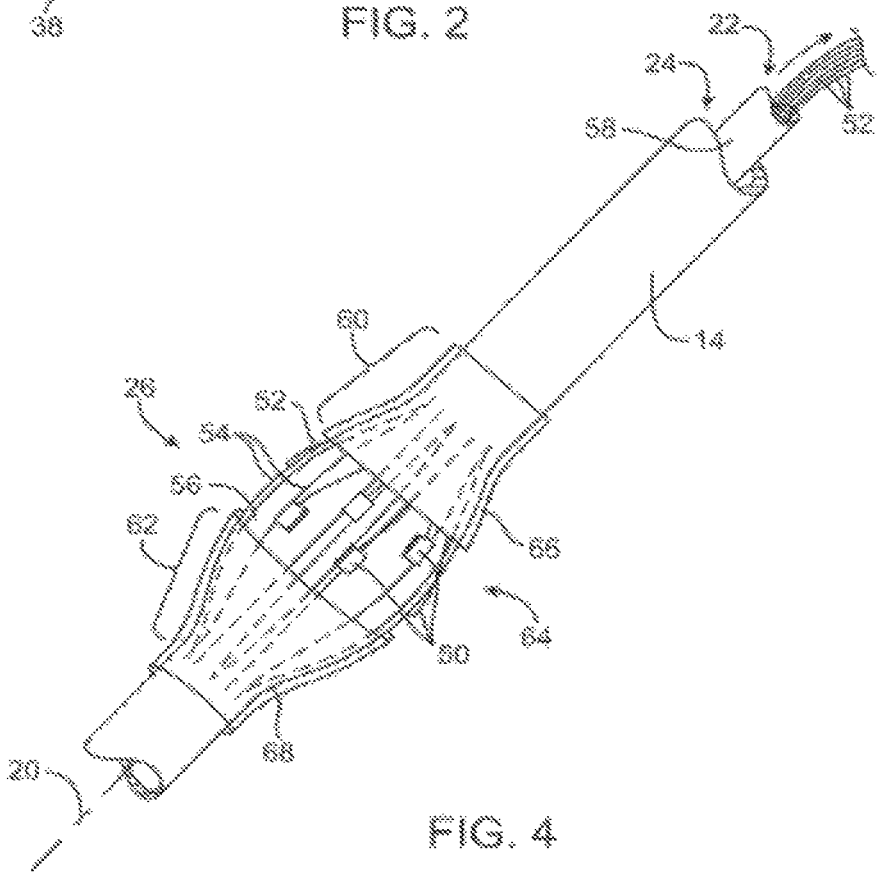
FIG. 4 illustrates an expandable basket and an associated electrode array of the catheter system of FIG. 2.

A second connector 44 of proximal housing 28 is in fluid communication with irrigation lumen 24 (see FIG. 4). Second connector 44 may be coupled to an irrigation fluid source for introducing conductive or non-conductive liquids, or the like, ideally for introducing heparinized saline. Both first and second connectors 32, 44 may optionally comprise a standard connector such as a Luer-Loc™ connector. In FIG. 3 connector 44 is schematically shown coupled to an aspiration vacuum source/infusion fluid source 45.

Referring now to FIG. 16, an exemplary catheter system 280 is illustrated. In this embodiment, catheter body 282 includes only a single lumen, which is large enough to accommodate an imaging catheter therein and also to be used as an irrigation lumen to bring irrigation fluid to irrigation ports 284. The lumen may decrease in diameter distally of irrigation ports 284, with the decreased diameter portion 286 fittingly receiving the imaging catheter within the lumen thereof so as to direct the irrigation fluid radially outward through the plurality of irrigation ports. This embodiment may be particularly useful when remodeling atherosclerotic materials using the methods illustrated in FIGS. 14A-14H, in which mile heating improves vessel size, optionally without requiring aspiration.

Catheter body 282 may include a braided shaft in which conductive wires (for example copper wires or beryllium-copper wires) are coated with a high temperature and/or high strength insulation material such as a layer of polyimide or the like. The braided wires may be sandwiched between layers of materials forming the shaft of catheter body 282. The shaft may, for example, comprise a plurality of layers of polyethylene, an inner Teflon™ PTFE layer, an outer nylon layer, and the like.

The wires of shaft 282 may be braided so as to inhibit capacitive losses between wires when electrical currents run through them. Capacitive losses may be decreased when a wire that carries a current from an energy source to an electrode of the catheter system and a wire that carries a current from an electrode back to the energy source are not parallel, but at an angle, ideally being perpendicular. This may be achieved by braiding the wires with appropriate pitch or a number of peaks per inch. The basket structure 170 of catheter system 280 may be included, with the basket structure being described in more detail with reference to FIGS. 12A-12H. Guide 286 may extend through basket 170 and may comprise a material transparent to the imaging catheter, optionally comprising HDPE, PET, or the like.

Referring now to FIGS. 2,3, and 4, proximal housing 28 also accommodates an electrical connector 46. Connector 46 includes a plurality of electrical connections, each electrically coupled to an electrode 50 via a dedicated conductor 52. This allows a subset of electrodes 50 to be easily energized, the electrodes often being energized with bipolar or monopolar radiofrequency energy. Hence, electrical connector 46 will often be coupled to an radiofrequency generator via a controller 47, with the controller allowing energy to be selectively directed to an eccentric portion of an engaged luminal wall. When monopolar radiofrequency energy is employed, patient ground may (for example) be provided by an external electrode or an electrode on catheter body 14. A processor 49 may manipulate signals from imaging catheter 34 to generate an image on display 39, may coordinate aspiration, irrigation, and/or treatment, and may automatically register the treatment with the image.

Processor 49 will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a nonvolatile memory, etc.) and/or a recording media (such as a floppy disk, a hard drive, a CD, a DVD, a memory stick, etc.). The code and/or associated data and signals may also be transmitted to or from the processor via a network connection (such as a wireless network, an Ethernet, an internet, an intranet), and some or all of the code may also be transmitted between components of catheter system 10 and within processor 49 via one or more bus, and appropriate standard or proprietary communications cards, connectors, and cables, will often be included in the processor. Processor 49 will often be configured to perform the calculations and signal transmission steps described herein at least in part by programming the processor with the softward code, which may be written as a single program, a series of separate subroutines or related programs. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit or a combination thereof. Standard or proprietary input devices (such as a printer, speakers, display, etc.) associated with modern computer systems may also be included, and processors having a plurality of processing units (or even separate computers) may be employed in a wide range of centralized or distributed data processing architectures.

In general, the present invention may make use of highly elastic, expandable structures, particularly of balloons or expandable structures formed from structural members separated by perforations so as to define a basket. Such structures can conform to an artery diameter before, during, and/or after atherosclerotic material removal. This expandability allows for direct contact of the electrodes against a targeted area, although the systems of the present invention may also make use of conductive fluid environments to complete a radiofrequency energy path, or conversely, use non-conductive fluid to enhance energy directed through tissue. Multiple electrodes can be distributed circumferentially around an intermediate portion of the expandable structure, and a subset of these electrodes can be activated to allow for eccentric tissue treatment.

Expandable structure 26 is illustrated in more detail in FIG. 4. Expandable structure 26 may expand resiliently when released from within a restraining sheath, or may expand by pulling tip 30 toward distal end 18 (see FIG. 2), optionally using a pullwire, an inner catheter body 58, or the like. Expandable structure 26 here comprises a perforate structure or basket having a series of structural struts or elements 54 with opening or perforations 56 therebetween. Perforations 56 may be formed, for example, by cutting elongate slits in a flexible tube material, or the basket may be formed by braiding elongate wires or ribbons, or other such suitable materials.

Expandable structure 26 generally includes a proximal portion 60, a distal portion 62, and an intermediate portion 64 therebetween. Each electrode 50 is mounted on an associated basket element 54 along intermediate portion 64, with an associated conductor 52 extending proximally from the electrode. Electrodes 50 are distributed circumferentially about axis 20 in an array, adjacent electrodes preferably being axially offset, ideally being staggered or alternating between proximal and distal axial locations. This allows bipolar energy to be directed between adjacent circumferential (sometimes axially offset) electrodes between adjacent distal electrodes, between adjacent proximal electrodes, and the like.

In some embodiments, proximal and distal barriers 66, 68 expand radially with proximal and distal portions 60, 62 of expandable structure 26. Barriers 66, 68 inhibit any debris and gases generated adjacent electrodes 50 from traveling within the body lumen beyond catheter 12. Barriers 66, 68 also allow an at least partially isolated environment to be established within the body lumen, for example, by replacing blood within a blood vessel with a more advantageous fluid environment forth electrodes. Alternative barriers may be provided instead of (or in combination with) barriers 66, 68, including one or more balloons axially offset from expandable member 26, elastic lips, or other such barrier structures. In other embodiments remodeling may be effected without generating significant debris, a desired treatment environment may be provided with localized irrigation and/or aspiration flows so that some systems may forego the use of barriers.

Figure 5:
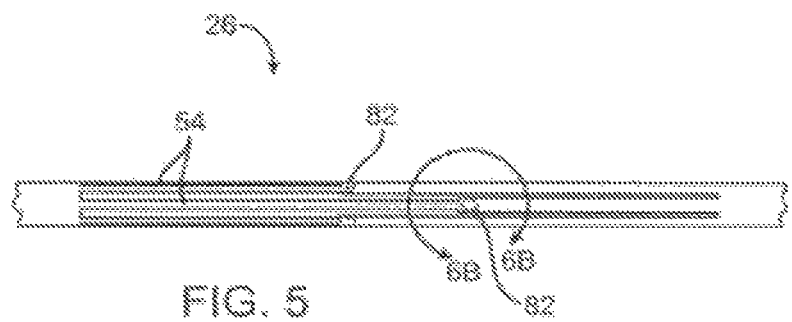
FIGS. 5 and 6 illustrate an exemplary basket structure having alternating axially offset electrodes in a circumferential array.
Figure 6:
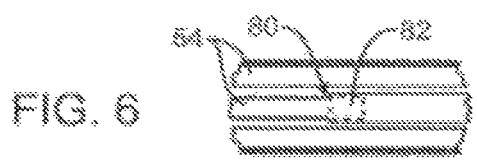

An exemplary expandable structure 26 is formed by cutting slots in a superelastic alloy tube such as a nickel titanium alloy or Nitinol™ tube. As can be understood with reference to FIG. 6, expandable structures 54 may have circumferential widths 80 which are enhanced adjacent an electrode and/or electrode mounting location 82. As can be seen in FIG. 5, the localized enhancement of the width 80 adjacent electrode mounting pads 82 may be axially offset, as described above. The slots forming expandable members 54, and hence the expandable members themselves may, for example, be 0.8 inches in length, with the expandable members having a circumferential width of about 0.25 inches.

Figure 7A:
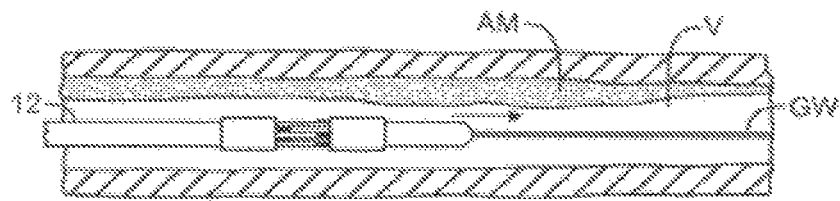
FIGS. 7A-E illustrate an exemplary atherosclerotic material remodeling and/or removal method using the catheter system of FIG. 2.
Figure 7B:
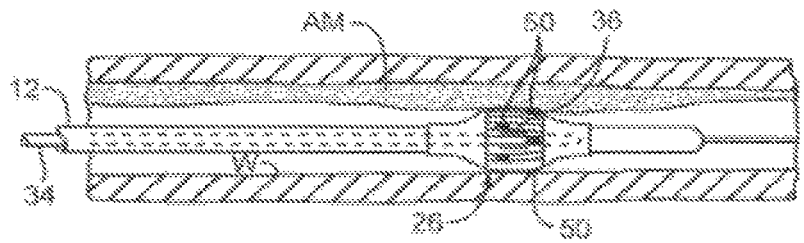
Figure 7C:

Referring now to FIGS. 7A and 7B, side and end views of an expandable barrier in the form of a collapsible cone can be seen. Barrier 66 here comprises a braided Nitinol™ wire 84 coated in silicone, for example, by dipping a braid of a superelastic alloy such as a Nitinol™ braid in liquid silicone and allowing it to harden. Such cones may then be mounted over the proximal and distal portions of the expandable structure. As noted above, a variety of alternative barrier membranes may be employed. FIG. 7C illustrates a basket 75 with an integral barrier 77 coated directly on the basket. Barrier 77 comprises a polyurethane, which may be quite tear resistant. Alternative barrier membranes may comprise other materials such as PT1-E, or the like.

Figure 8:
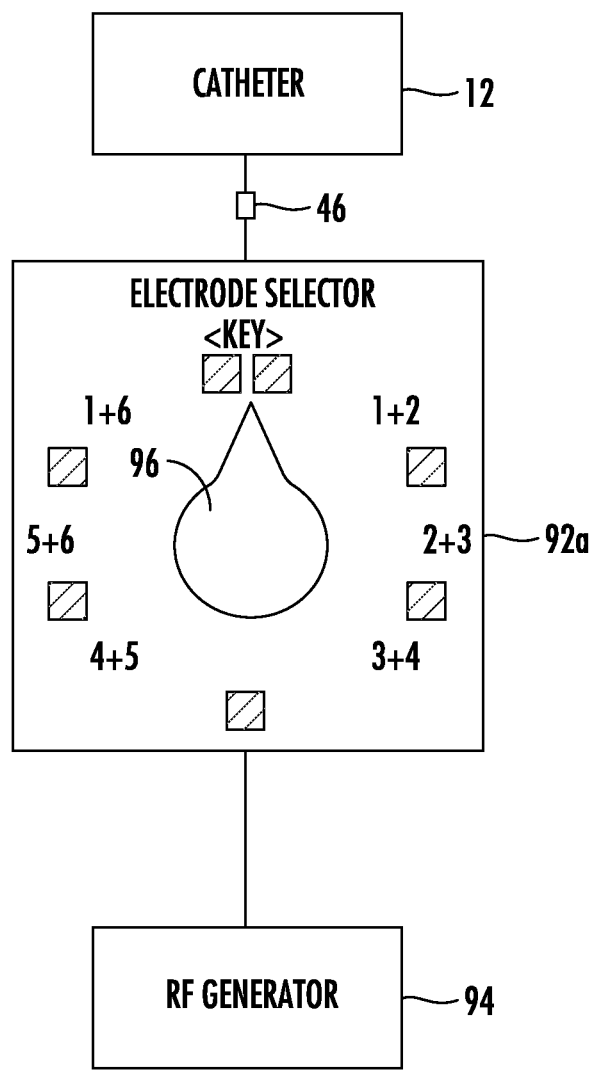
FIGS. 8-10 schematically illustrate controllers for selectively energizing electrodes in the system of FIG. 2.
Figure 9:
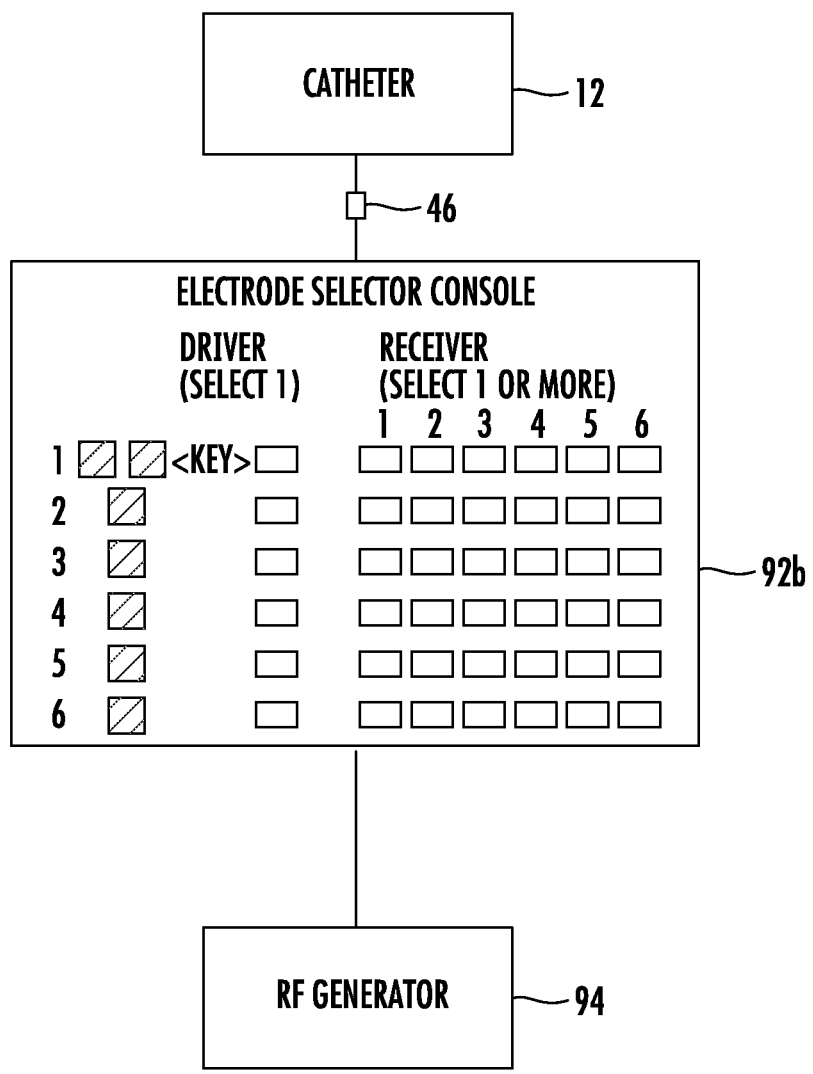

Referring now to FIGS. 8 and 9, exemplary electrodes 50, supported by polyimide alloy expandable members 54 may be coated with a high-temperature polymer. Conductors 52 extend proximally from electrodes 50 as described above. High contrast radiopaque markers such as gold, platinum, or platinum/iridium alloy may be attached to or near these struts. The markers could also be used as the electrodes.

Referring now to FIGS. 33, 33A, 34, 35A-35F, the present invention discloses a method for remodeling artery tissue using a catheter system that uses mild heat to provide tissue surface temperatures in a range between about 50° C. and about 65° C. to gently remodel the tissue, such that arteries may be opened. The method includes expanding a catheter balloon within the artery lumen with a first pressure that brings the balloon in contact with the artery tissue. The plurality of electrodes 634 are coupled with the artery tissue 650 so as to define a plurality of remodeling zones in the artery tissue 650 when the balloon 620 is in contact with the artery tissue 650. The plurality of electrode pairs 634A-634F are then energized with associated desired quantities of bipolar tissue remodeling energy so as to heat each of the plurality of remodeling zones with the associated desired tissue remodeling energy, the remodeling energy being configured to avoid muscular contraction and inhibit both acute and long-term occlusion of the lumen. In some instances, it may be desirable to obtain baseline measurements of the tissues to be treated (which may be characterized with means such as intravascular ultrasound, optical coherence tomography, etc.). Baseline measurements may be taken to help differentiate adjacent tissues, as the tissue signatures and/or signature profiles may differ from person to person. Additionally, the tissue signatures and/or signature profile curves may be normalized to facilitate identification of the relevant slopes, offsets, and the like between different tissues.

As shown in FIG. 33, one embodiment of a catheter system for use in the present invention includes an angioplasty catheter with a plurality of electrodes 634 mounted on the exterior of a angioplasty balloon 620. A radiofrequency controller 49, generator or power source 642, and connecting cable 46 provide energy to the catheter. Catheters may be approximately 135 cm in length and may be provided with balloon diameters ranging from about 2 mm to about 10 mm so as to accommodate common arterial sizes. The catheter uses mechanical and radiant energy intended to modify tissue proximate to a lumen 660, such as in-stent restenosis, or other diseased tissue, resulting in a larger artery lumen. The temperature that is generated is low and the total application time is shorter than most angioplasty procedures performed today. The catheter device is compatible with standard angioplasty equipment, thereby allowing access of vasculature via contralateral or ipsilateral common femoral approach using conventional angioplasty techniques. The catheter system 10 includes a balloon catheter 12 having a catheter body 14 with a proximal end 16 and a distal end 18. Catheter body 14 is flexible and defines a catheter axis 20, and may include one or more lumens, such as a guidewire lumen and an inflatable lumen. Still further lumens may be provided if desired for other treatments or applications, such as perfusion, fluid delivery, imaging, or the like. Catheter 12 includes an inflatable balloon 620. Housing 629 includes a first connector 626 in communication with guidewire lumen 622 and a second connector 628 in fluid communication with inflation lumen 624. Inflation lumen 624 extends between balloon 620 and second connector 28. Both first and second connectors 626, 628 may optionally comprise a standard connector, such as a Luer-Loc™ connector. Housing 629 also accommodates an electrical connector 638 electrically coupled to electrodes 634 via conductors 636. This allows electrodes 634 to be easily energized, the electrodes often being energized by a controller 49 and power source 642, such as bipolar or monopolar radiofrequency energy, microwave energy, ultrasound energy, or other suitable energy sources. In one embodiment, electrical connector 46 is coupled to a radiofrequency generator via a controller 49, with controller 49 allowing energy to be selectively directed to electrodes 634. Electrodes 634 are mounted on a surface of balloon 620, with associated conductors 636 extending proximally from the electrodes. Electrodes 634 may be arranged in many different patterns or arrays on balloon 620. The system 10 may be used for monopolar or bipolar application of energy. For delivery of monopolar energy, a ground electrode is used, either on the catheter shaft 14, or on the patients skin, such as a ground electrode pad. For delivery of bipolar energy, adjacent electrodes are axially offset to allow bipolar energy to be directed between adjacent circumferential (axially offset) electrodes 634.

Referring to FIGS. 33, 33A, 34, and 35D, multiplexing between selected electrodes of an array or sub-array can be effected by selectively energizing a plurality of electrode pairs, such as those shown by 634A-634F, treatment zones for the sub-array being disposed between the electrodes of the pairs so that the energy passes therethrough. For example, a pair of electrodes selected from electrodes 634A, 634B, 634C, 634D, 634E, 634F distributed about balloon 620 (with the selected electrodes optionally being positioned opposite each other) may be energized and then turned off, with another pair then being energized, and so forth. An example of a firing order may be 634A and 634D, then 634B and 634E, then 634C and 634F. Bipolar potentials between the electrodes of the pair can induce energy paths 653 in the same general tissue region, with the power dissipated into the tissue optionally remaining substantially constant. The electrode combinations 634A-634F may be chosen so as to minimize the space between treatment zones as represented by energy path 653, where treatment zones may be defined by the tissue volume between paired electrodes. For example, an in-stent restenosis may require energy delivery around the full circumference of a lumen but the open portion of the lumen may not be concentric with the natural center of the healthy vessel (as shown, for example in FIG. 35A). In this circumstance, individual pairs of electrodes 634A-634F may be energized and controlled until a desired temperature is reached or until proximity to the implanted stent 652 is reached (FIG. 35E). Electrode pairs may optionally be selected again so as to fill in the gaps between the first tissue treatment zones 653 and the controlled delivery of energy may be repeated such that essentially the full circumference of the lumen receives treatment and is restored as shown in FIG. 35F. Most preferably for treating in-stent restenosis, a first plurality of electrode pairs selected from 634A-634F are energized sequentially to create a first pattern of treatment zones. Then, an indexed plurality of electrode pairs selected from 634A-634F are chosen so as to create a second pattern of treatment zones, with at least some degree of overlap with the first treatment zones, and then energized sequentially to complete the energy treatment dosage to be used. An exemplary energy dose for in-stent restenosis may be for the first plurality of electrodes to be provided 4 Watts of power for 2 seconds, and the second plurality of electrodes to b provided 4 Watts of power for 1 second.

Figure 13:
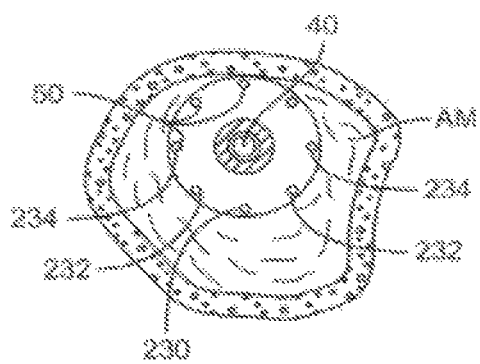
FIG. 13 is a schematic cross sectional view showing the application of different power levels through different electrodes so as to eccentrically remodel atherosclerotic materials.

Referring now to FIG. 13, controllers of the catheter systems described herein may allow distribution of differing power levels to differing pairs of electrodes. For example, in response to a circumferential distribution of atherosclerotic material AM such as that illustrated in FIG. 13, a controller may direct 50 watts of energy to a first electrode 230, 30 watts of energy to a pair of second electrodes 232 and only 10 watts of energy to a pair of third electrodes 234. Other electrodes may have no energy directed to them. In some embodiments, a differing power directed to the differing electrodes may be provided by controlling the duty cycle, for example, with 50 watts being provided by energizing one or more electrode for 50% of the time, 30 watts being provided by energizing an electrode 30% of the time, and the like. The power and the duration of the cycle may be of any value to achieve the desired treatment, which for example, may include powers and times computed within a temperature regulating closed-loop control algorithm.

Referring now to FIG. 34, balloon 620 generally includes a proximal portion 630 coupled to inflation lumen 624 and a distal portion 632 coupled to guidewire lumen 622. Balloon 620 expands radially when inflated with a fluid or a gas. In some embodiments, the fluid or gas may be non-conductive and cooled. In some embodiments, balloon 620 may be a low pressure balloon pressurized to 6 atmospheres or less to contact the artery tissue. In other embodiments, balloon 620 is a standard angioplasty balloon. Balloon 620 may comprise a compliant or non-compliant balloon having folds to facilitate reconfiguring the balloon from a radially expanded, inflated configuration to a low profile configuration, particularly for repositioning or removal after use. In a preferred embodiment, balloon 620 is comprised of a compliant material and is inflated to a pressure of 6 atmospheres or less.

Delivering radiofrequency energy directly to a specimen requires a monopolar or bipolar pathway. In a monopolar configuration there is a single pole or electrode from which the energy emanates and a grounding plate or pad to absorb the energy and complete the circuit. This configuration creates higher energy densities at the electrode than at the grounding pad, resulting in a single affected area or treatment zone at the electrode that is directly related to the geometry of the electrode and the power applied to the electrode. As the surface area of the monopolar electrode increases, so does the size of the treatment zone. The bipolar configuration uses two poles or electrodes to set up an electric field between the electrodes thus creating a conduction path for the current to flow. Unlike the monopolar electrode configuration where only surface area is deterministic to the treatment zone, the bipolar electrode configuration has three determining factors: electrode separation, parallel length, and width; each of which have a separate and distinct effect on the treatment zone.

Taking into consideration the effect each determining factor has on the affected treatment zone, and the overall impedance as seen by the generator, the separtion or distance between electrodes has the greatest effect, followed by parallel length and lastly electrode width. Electrode separation is goverened by Coulombs law, where at very close distances the impedance as seen by a generator is very small and as separation of the electrodes increases the impedance increases at a rate that is proportional to the square of their separation. As this separation increases, a higher potential energy is generated due to the increase in impecdaance creating a greater flux density that results in a greater treatment depth. The effect of increasing the paralel length shared by the two electrodes causes the treatment zone to increase only as much as the parallel electrode length is increased. There are no additional depth effects only an increase due to added length. This additional length causes the impedance as seen by the generator to decrease due to the increase in potential parallel paths for the current to flow through. Electrode width has the least effect on the treatment zone and is governed by the same laws as electrode separation. As the width of the electrode is increased incrementally, the added effect is small due to the inverse square law for eac incremental element placed on the outer edges of the existing electrode elements. Although this effect may be small it aides in reducing the surface heat generated by reducing the current density at the inside edge of the electrode pairs. This effect is amplified as the conductance of the electrode material approaches the conductance of the tissue being treated due to the path of least resistance becoming the tissue rather than the electrode itself.

Referring to FIGS. 33 and 33A, catheter body 14, with distal end 18 and balloon 620, of catheter system 10 is positioned within a body lumen such that electrodes 634 may deliver energy to tissues proximate to electrodes 634 such as the tissues of the luminal wall 650 and tissues adjacent the luminal wall 660. The type and location of tissues 650 and 660 may be of any type found within proximaity of a body lumen up to a distance of about 1 cm or more with the most preferred distances being approximately within about 5 mm or less.

Referring now to FIGS. 35A-35F, atherosclerosis (FIG. 35A) is a common form of tissue disease affecting the arterial luminal wall 650, resulting in a greatly reduced luminal diameter 651 or a completely occluded lumen (not shown). One of ordinary skill in the art will recognize that luminal wall 650 is comprised of the intimal, medial, and adventitial layers, and may be further comprised of many cellular and/or tissue states and types as it may relate to the specific anatomical location and/or biological process desired to be treated by the delivery of therapeutic energy.

Figure 35A:
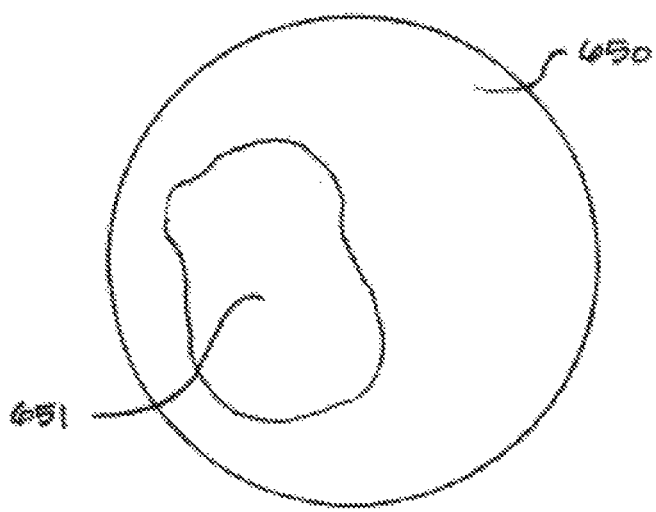
FIG. 35A is a cross sectional view of a body lumen with occlusion.
Figure 35B:
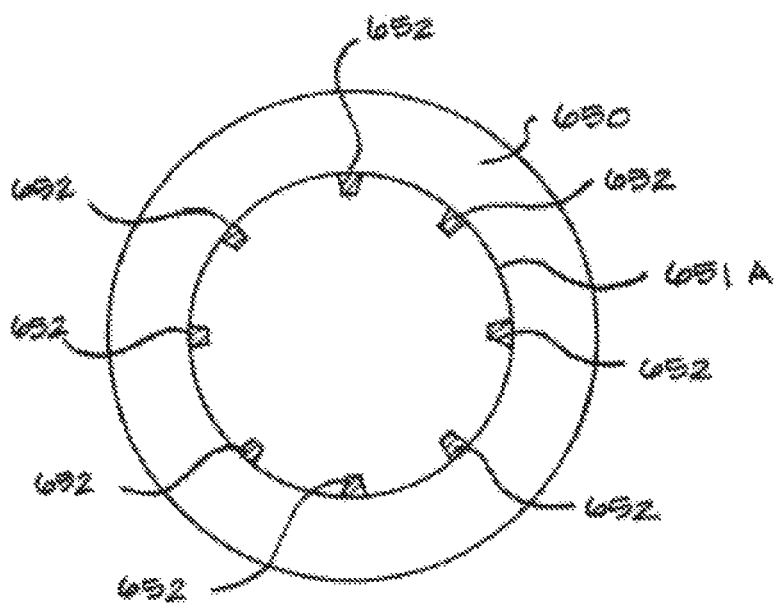
FIG. 35B is a cross sectional view of the body lumen of FIG. 35A following a dilation procedure and the implantation of a stent.

As illustrated in FIG. 35B, angioplasty and the implantation of a stent structure 652, results in the restoration of blood flow by acutely establishing an increased post-procedure lumen 651A. Angioplasty and stent implantation its a well-established means for treating arterial stenosis, however, restenosis or the treated lumen frequently occurs as a byproduct of a biological cascade that may develop in response to the angioplasty procedure.

Restenosis involves the growth of new tissue within the arterial wall caused by a biological cascade mechanism of platelets, polymorphonuclear leucocytes, and macrophage aggregation leading to the migration of smooth muscle cells from the media to the intima coupled with smooth muscle cell proliferation at the intimal layer. The acute onset of in-stent restenosis begins with relocation of plaque and reorganization of thrombus, in conjunction with an acute inflammatory response to injury of the endothelium that promotes fibrin and platelet deposition. Leucocytes gather in and around the injury caused by balloon dilation and stent implantation. As the biological cascade continues, leucocyte recruitment is further sustained. As the in-stent restenosis process continues, smooth muscle cells in the medial layer modify and migrate from the medial layer to the intimal layer before further proliferating as neointimal tissue. The volume of stenotic neointimal tissue is increased by smooth muscle cell synthesis of extracellular matrix predominantly comprised of proteoglycans and collagens.

FIGS. 35C, 49A, 50A, and 51A illustrate how in-stent restenosis may result in a subsequent reduction of the treated lumen. As a result of the biological process described above, the post-procedure lumen diameter 651A is reduced to lumen diameter 651B. Although stent structure 652 remains intact, the proliferation of cells in luminal wall 650 completely surrounds stent structure 652 rendering it ineffective in maintaining luminal patency. The combination of restenosis and the presence of an implanted stent provides several challenge to effective treatment. Reperforming angioplasty is unlikely to be effective because the restenosis may be the result of localized trauma caused by the original angioplasty procedure. Moreover, there is risk that the implanted stent structure 652 may be damaged during a second, in-stent angioplasty procedure. Mechanical ablation procedures are an alternative to angioplasty for treatment of in-stent restenosis, however, mechanical ablation may often result in further tissue trauma and also present the potential for causing damage to stent structure 652. Thermal ablation is an additional alternative to angioplasty, however, the high temperatures associated with ablative removal of tissue may also result in tissue damage and the eventual restenosis of the lumen as a result of the thermal trauma in tissue adjacent to the ablation site. Therefore, a means and procedure to thermally debulking the in-stent restenosis that avoids traumatic thermal damage to adjacent tissues in the luminal wall 650, and that avoids damage to stent structure 652, presents an advancement over the treatment means presently available.

Figure 35C:
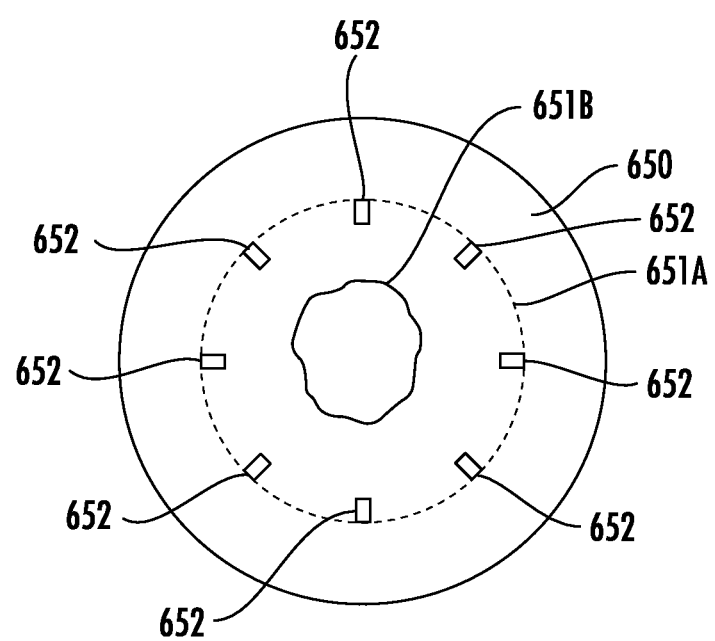
FIG. 35C is a cross sectional view of the body lumen of FIGS. 35A-35B with the subsequent development of in-stent restenosis.
Figure 35D:
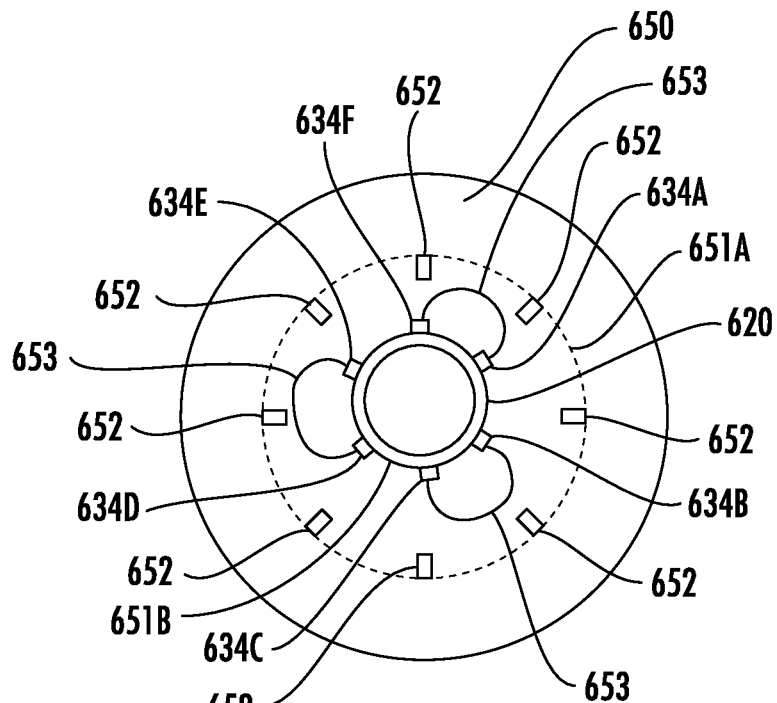
FIG. 35D-35F are cross sectional schematic representation of the system of FIG. 33 positioned for use in, and treatment of, the body lumen of FIG. 35C.
Figure 35E:
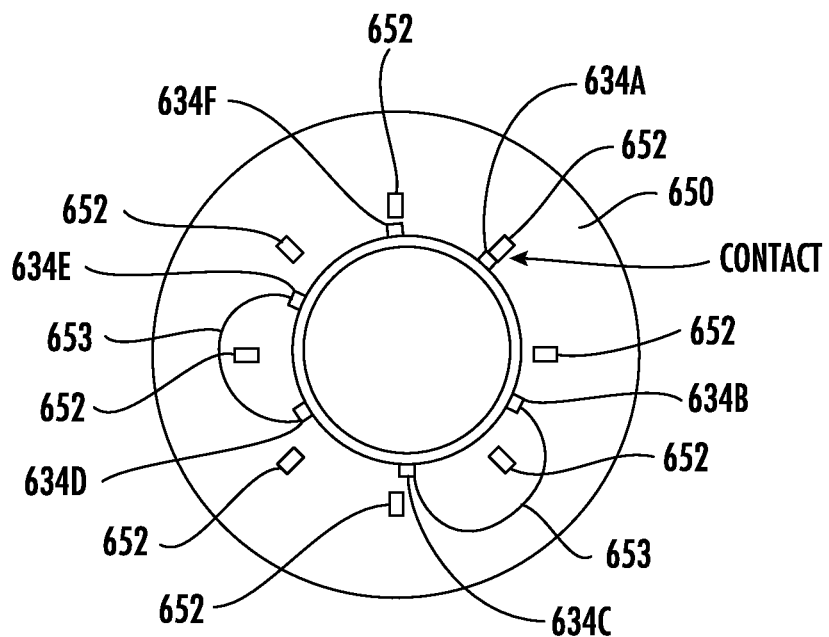
Figure 35F:
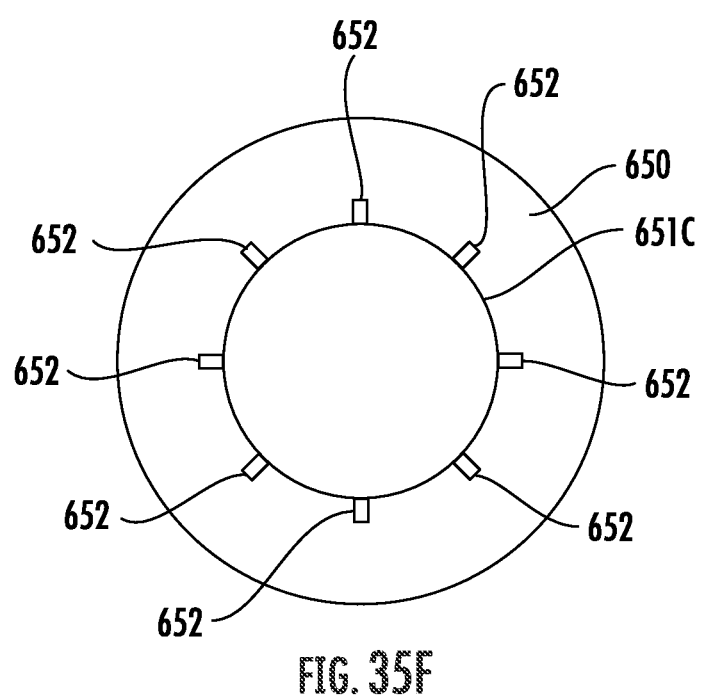
Figure 37:
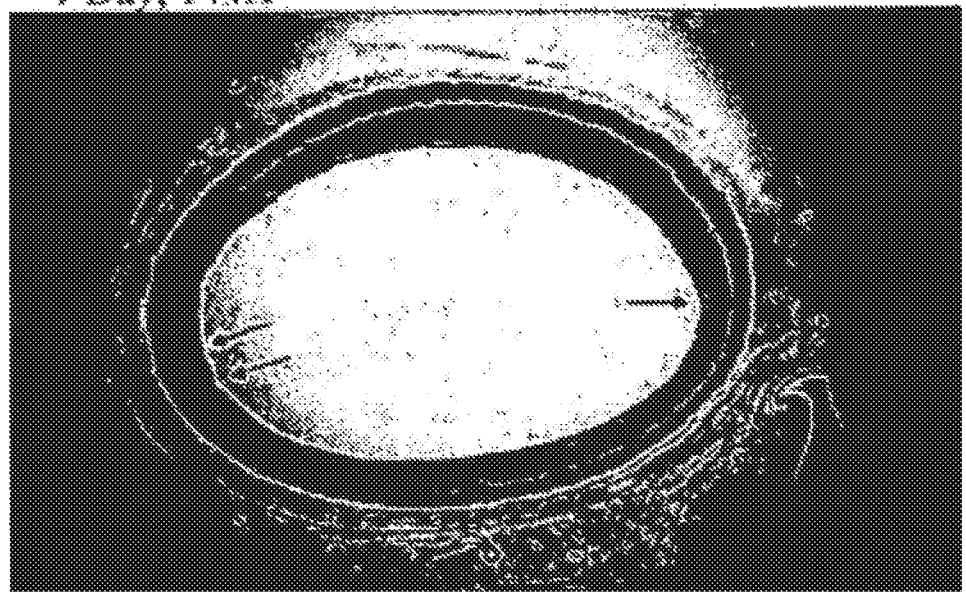
FIG. 37 shows histological results for the application of 1 Watt for 8 seconds at seven days.
Figure 38:
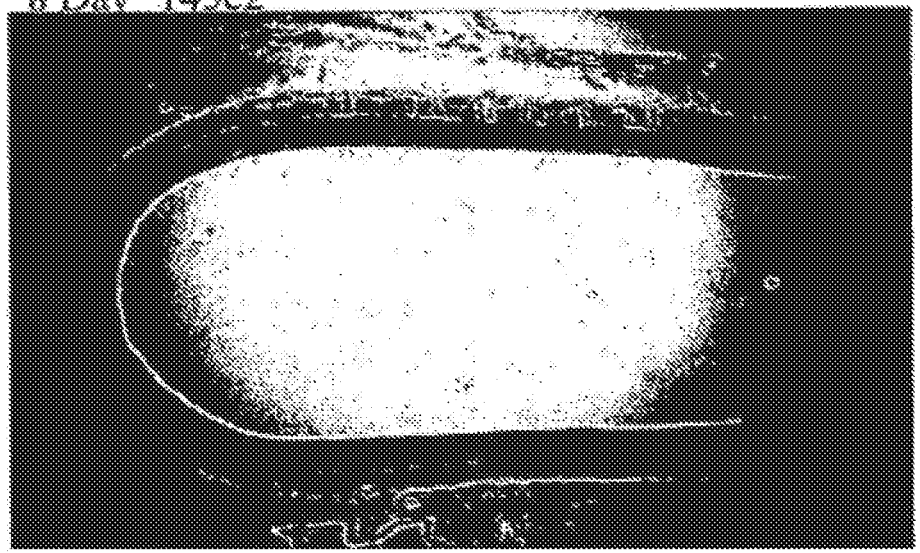
FIG. 38 shows histological results for the application of 2 Watts for 2 seconds at eight days.
Figure 39A:
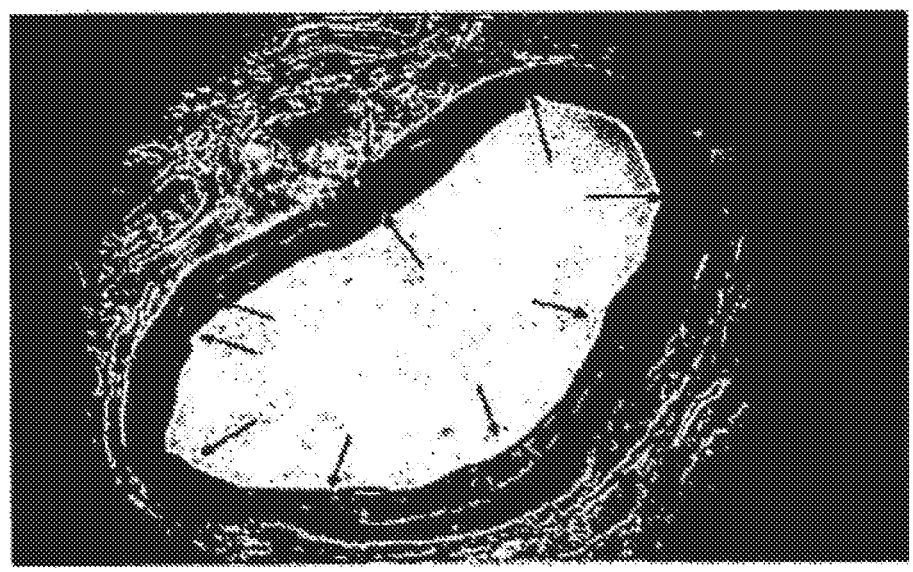
FIGS. 39A and 39B show histological results for the application of 4 Watts for 1 second at seven days.
Figure 39B:
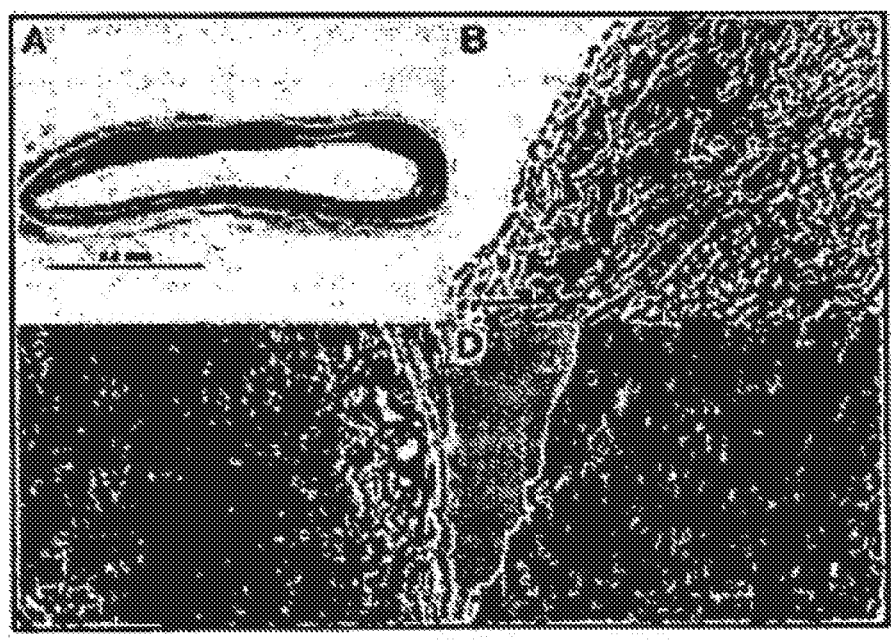
Figure 39C:
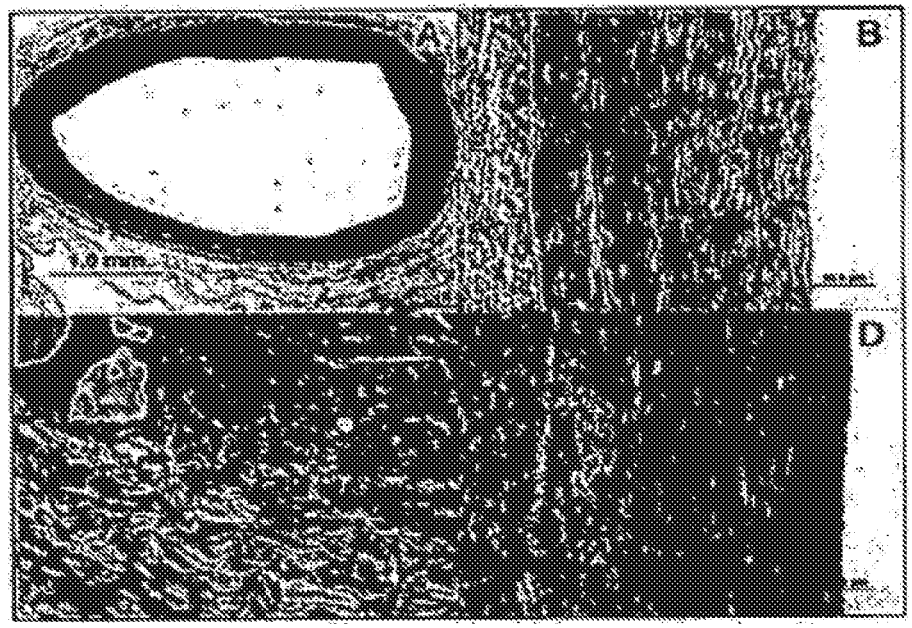
FIG. 39C shows histological results for the application of 4 Watt for 1 second at thirty days.
Figure 40A:
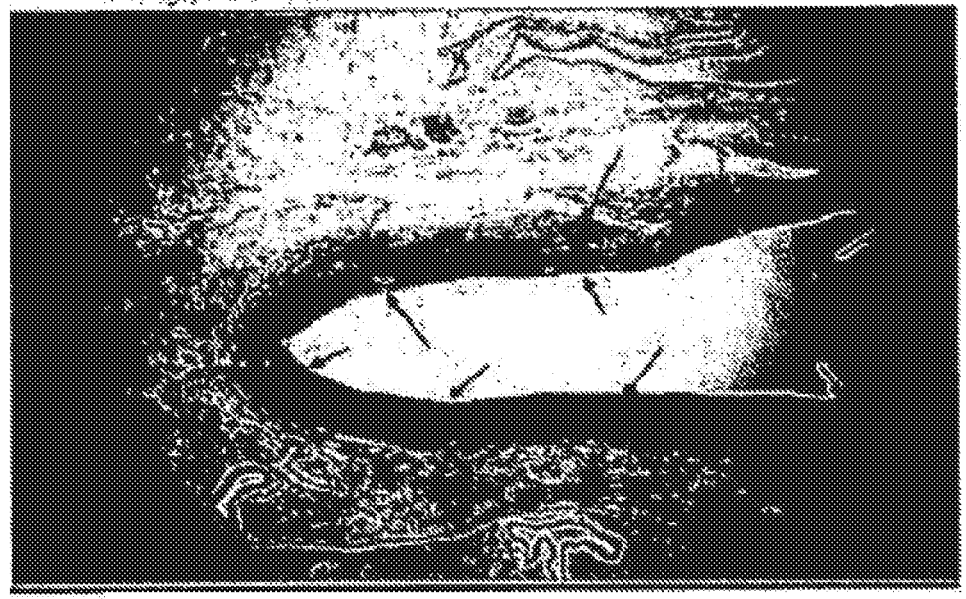
FIGS. 40A and 40B show histological results for the application of 2 Watts for 4 seconds at seven days.
Figure 40B:
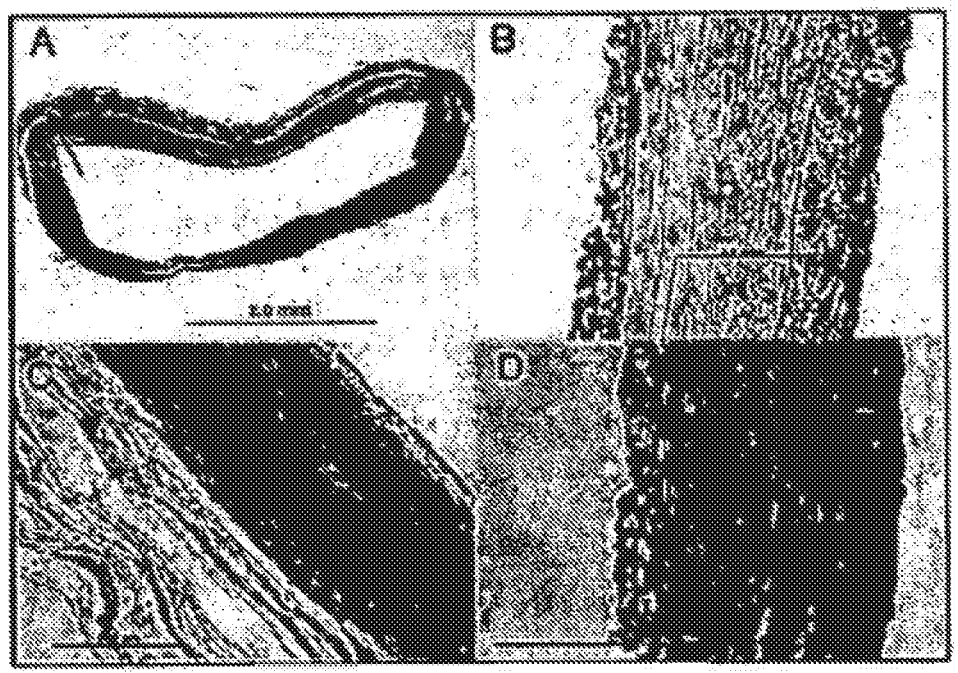
Figure 40C:
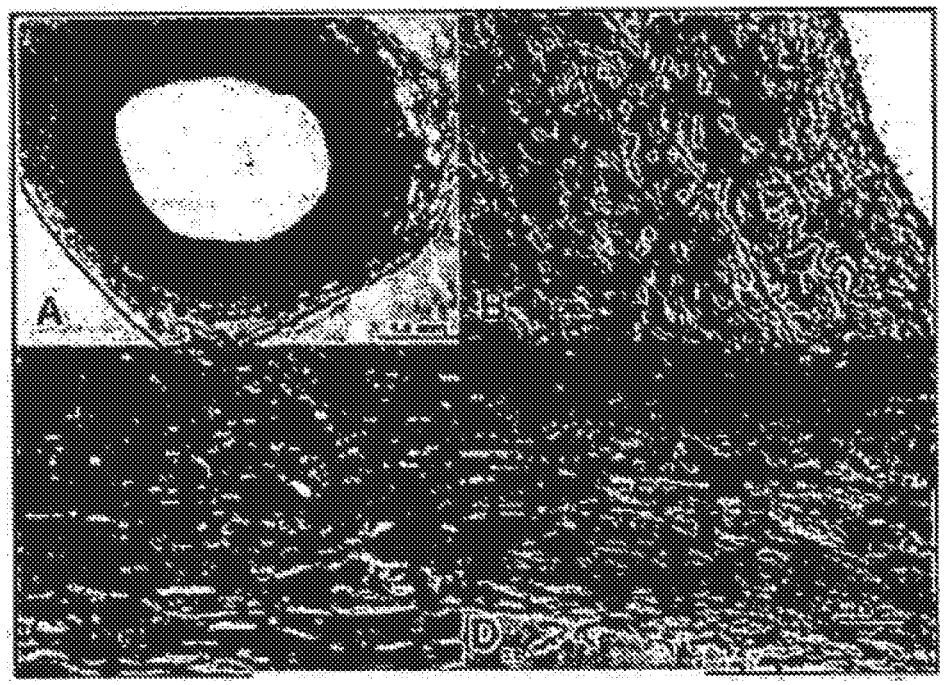
FIG. 40C shows histological results for the application of 2 Watt for 4 seconds at thirty days.
Figure 41A:
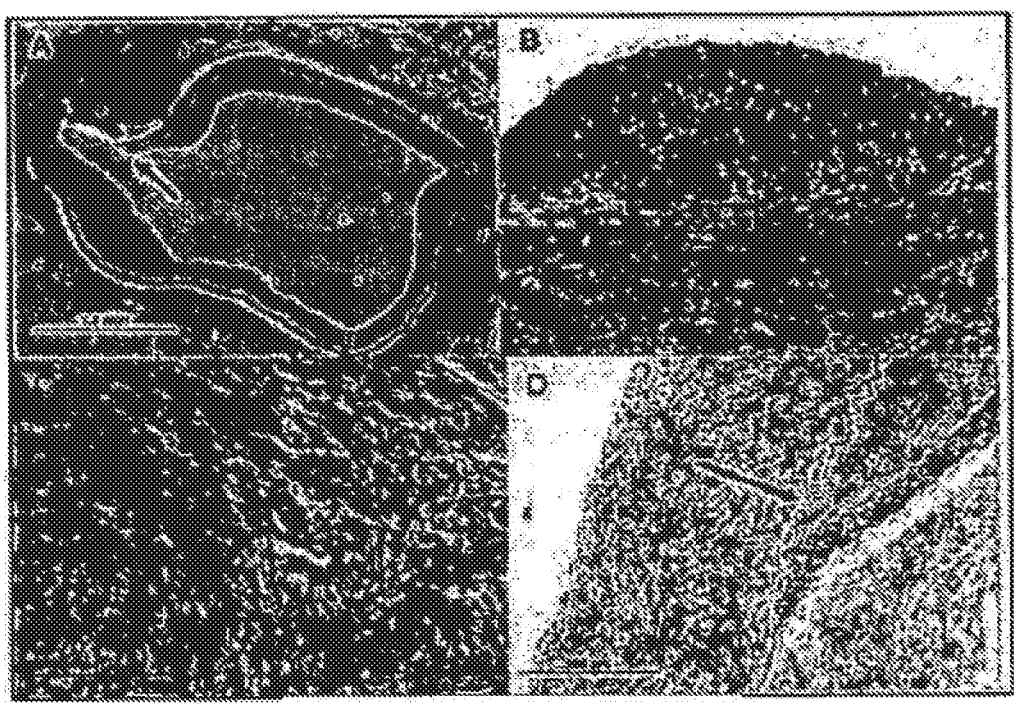
FIG. 41A shows histological results for the application of 3 Watt for 2 seconds at seven days.
Figure 41B:
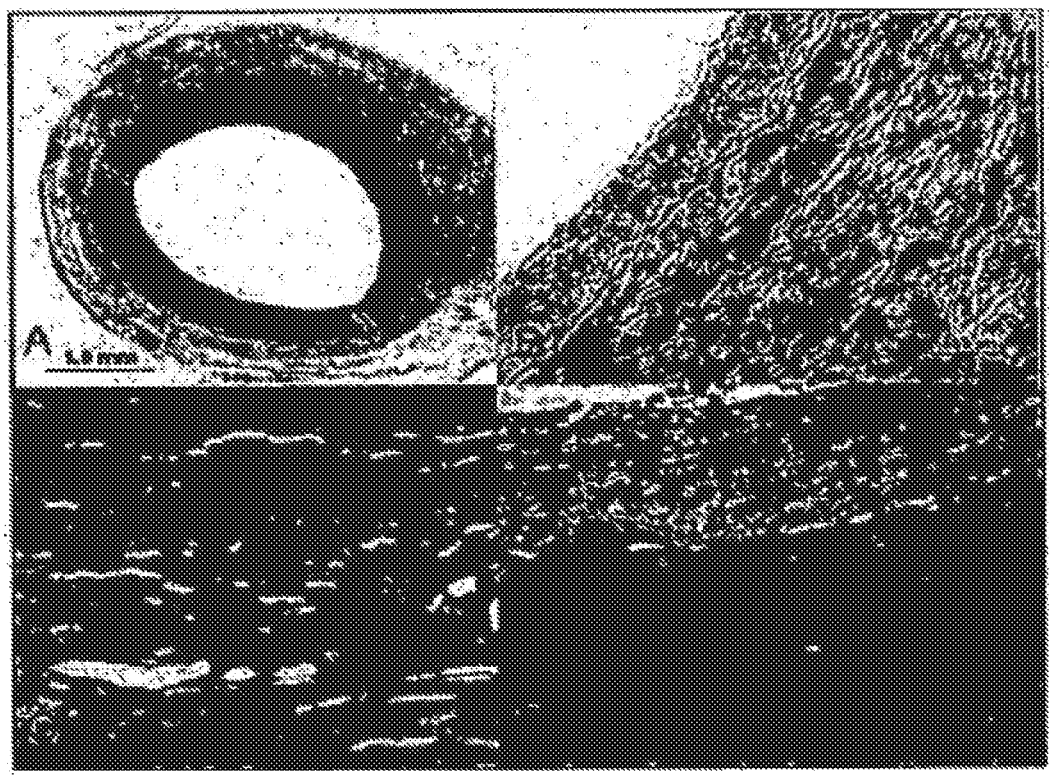
FIG. 41B shows histological results for the application of 3 Watt for 2 seconds at thirty days.

Referring now to FIG. 35D, balloon 620 of the catheter system 10 in FIG. 33 is shown in a state of inflated contact with luminal wall 650 at a diameter approximate to restenosed diameter 651B (FIG. 35C). The balloon pressure is sufficient to provide electrical contact between electrodes 634A-634F and luminal wall 650 such that an energy path 653 may be established between the various electrodes 634A-634F, as may be desired. A first analysis of tissue may be made by applying energy through energy paths 653 using bursts of energy in a range of frequencies to measure impedance, by using other imaging modalities such as IVUS or the like as described herein, or by using impedance analysis and imaging in combination. For illustrative purposes, balloon 620 is shown with a plurality of electrodes 634A-634F, however, any number of electrodes may be distributed about the circumference of balloon 620. Additionally, energy paths 653 are for illustrative purposes shown between specific electrodes but may also be formed between any electrodes forming a pair using monopolar configurations, bipolar configurations, and bipolar configurations with electrode multiplexing. This arrangement creates an energy path 653 through the tissue that delivers energy or heat ("tissue remodeling energy") in particular treatment zones or segments of tissue between the electrode pairs 634A-634F ("remodeling zones" or "treatment zones") having a volume between the electrode pairs at a specific depth. Using different combinations of electrode pairs may reduce or eliminate gaps between the remodeling zones by using overlapping pairs.

By using pairs of electrodes 634A-634F in a bipolar system, tissue remodeling energy will go through one or more of non-target tissue, target tissue, or a combination of both non-target and target tissues between the electrode pairs in the remodeling zones. Any number of electrode pairs may be used in different patterns or arrays to create a number of remodeling zones. The controller 49 (FIGS. 2 and 33) may apply either constant power, constant current, constant voltage, or regulate to a constant temperature whichever has the most advantage. A therapeutic dose of energy may be applied to luminal wall 650 to cause shrinkage and remodeling of the in-stent restenosis using the heating and control methods described herein such that the target tissue may be debulked through the application of energy while the heating of a non-target tissue is avoided to a degree that may result in tissue trauma and further subsequent luminal stenosis.

Referring now to FIG. 35E, the thermal treatment of the in-stent restenosis is shown in-progress. Balloon 620 may be further increased in diameter to maintain tissue contact with luminal wall 650 but pressure in balloon 620 is not used as the means of luminal dilation. As the electrodes 634 of balloon 620 continue to deliver therapeutic energy along paths 653, the previously occlusive tissue of luminal wall 650 shrinks, resulting in a restoration of luminal patency. As patency is restored, the stent structure 652 may begin to be exposed. Because electrodes 634A-634F may be selectively energized, certain specific electrodes may either cease to be energized or may not be selected for energizing depending on the degree of proximity or actual contact between an electrode 634 and stent structure 652. As illustrated, electrode pair 634F and 634A, have ceased to be energized because of the point of CONTACT between electrode 634A and stent structure 652. As an alternate example, electrode 634E and 634F may be selected to be energized until actual contact between electrode 634F and stent structure 652 occurs, or may cease to be energized because electrode 634F is sufficiently proximate to stent structure 652. Electrode pair 634D and 634E and electrode pair 634B and 634C may continue to be energized until reaching actual contact or sufficient proximity to stent structure 652. The change in impedance in the electrical circuit formed by electrode pairs along energy paths 653 may be used to determine the proximity of stent structure 652 to an electrode 634 and may be used to selectively energize electrodes 634A-634F based on tissue characterization prior to and/or during treatment.

Referring now to FIG. 35F, the resultant luminal diameter 651C following the thermal treatment for the pervious in-stent restenosis by luminal wall 650 is increased front the previous diameter 651B (FIG. 35C). For the purposes of illustration, lumen 651C is shown to be roughly equivalent to the inner diameter of stent structure 652. The final diameter of the lumen may be any preferred diameter based on energy delivery, tissue temperature control, physician selected requirement, and the like.

The method for treatment of in-stent restenosis may further be comprised to include the treatment of lesions beyond the stented portions, or between stented portions, of a blood vessel using the same energy delivery and tissue treatment devices and methods described herein. This may be of particular advantage in the case of diffuse arterial disease where it may be common to have sections of an artery with in-stent stenosis, stenosis between stents, and/or stenosis along a significant portion of the arterial length.

In one preferred example of thermal treatment of in-stent restenosis using the physical embodiments of the present invention, a balloon is inflated to a pressure sufficient to cause electrical contact between luminal tissue and electrodes. Balloon pressure may be about 20 atmospheres or less, more preferably about 10 atmospheres or less, and most preferably about 6 atmospheres or less. Using the illustrative electrode arrangement of FIG. 35D, the electrode pairs 634F and 634A, 634B and 634C, 634D and 634E are energized with about 4 Watts of power for about 2 seconds. An alternate electrode pairing of 634A and 634B, 634C and 634D, 634E and 634F are subsequently selected and energized at about 4 Watts of power for about 1 second. The target tissue is provided a therapeutic remodeling energy of about 65° C. or less.

The controller 49 (FIGS. 2 and 33) may energize the electrodes with about 0.25 to 5 Watts average power for 1 to 180 seconds. Higher energy treatments may be performed at lower powers and longer duration, such as 0.5 Watts for 90 seconds or 0.25 Watts for 180 seconds. Using a wider electrode spacing, it would be appropriate to scale up the power and duration of the treatment, in which case the average power could be higher than 5 Watts, and the total energy could exceed 45 Joules. Likewise, using a shorter or smaller electrode pair would require scaling the average power down, and the total energy could be less than 4 Joules. The power and duration are calibrated to be less than enough to cause severe damage, and particularly less than enough to ablate diseased tissue 48 within a blood vessel. Suitable methods and devices for adaptation and/or use in the present system may also be described in U.S. Pat. Nos. 5,098,431; 5,749,914; 5,454,809; 4,682,596; and 6,582,423, among other references; the full disclosure of each of these references is incorporated herein by reference.

Different tissue types have different characteristic electrical impedances that cause the tissue to absorb energy of certain frequencies or frequency ranges more readily than others. By applying energy at the specific frequency or range of frequencies that the tissue is more conductive, energy penetrates the tissue more readily. Frequency targeting seeks to deliver more energy to the targeted tissue by determining the frequency or range of frequencies at which the impedance of the targeted tissue is equal to or greater than that of non-target tissue, such as by operation at or below a threshold frequency. For example, energy delivered at a specified frequency or range of frequencies may cause more heat to be dissipated in a collateral tissue than energy delivered outside of those specific frequencies.

Figure 25:
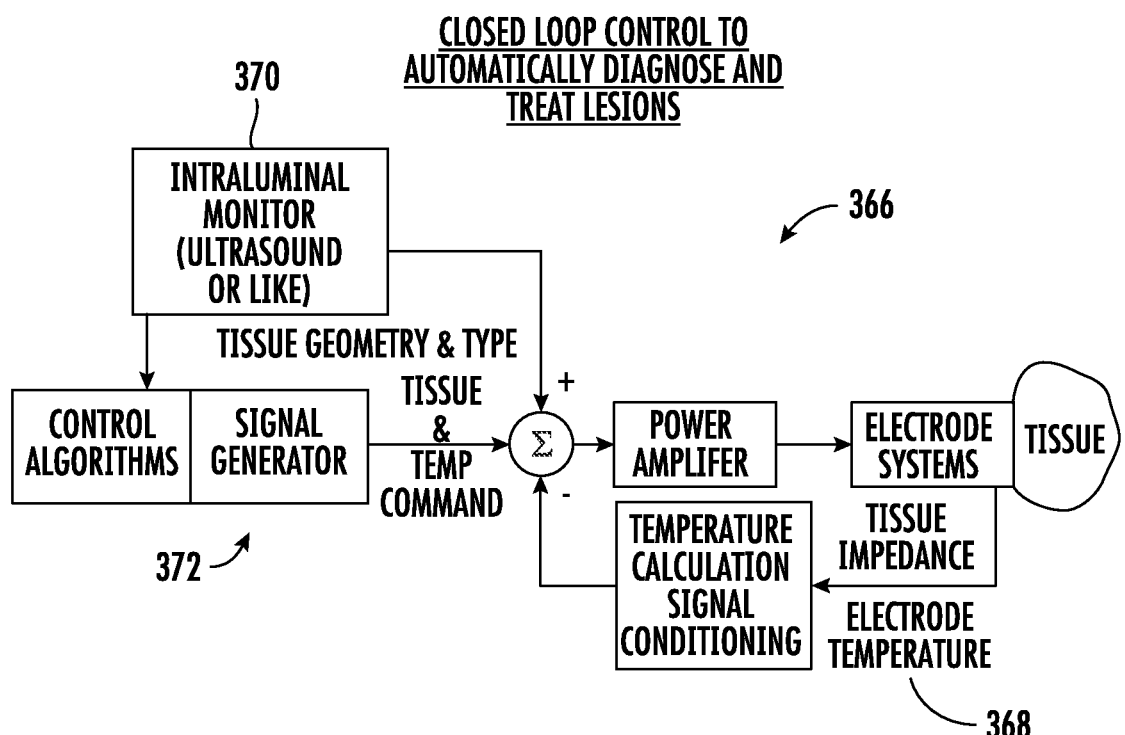
FIG. 25 illustrates one embodiment of a closed loop control system to automatically diagnose and treat lesions within a vessel utilizing tissue information from an external source such as IVUS.

Closed loop control can be understood with reference to FIG. 25. Impedance measurements over frequency ranges and across multiple electrodes may be utilized to verify electrode location relative to tissue landmarks, optionally be correlation to companion intraluminal measurement devices such as IVUS prior to and during therapy. Data about the condition of the tissue, optionally including temperature change, electrode to tissue interface impedance, tissue impedance, electrode to tissue or blood contact, and intraluminal geometry and tissue type from ultrasound or other sources, can be utilized by a controller as inputs to a closed loop control system 366.

Figure 42:
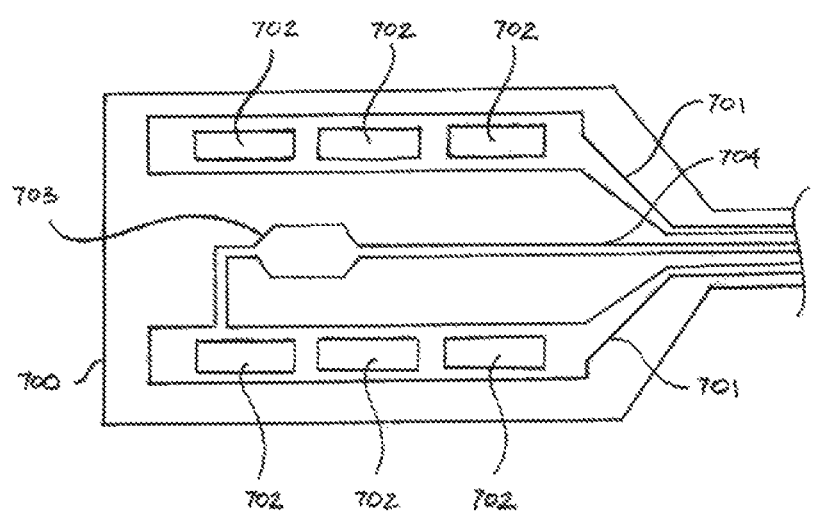
FIG. 42 is a schematic view of an electrode configuration with temperature sensing means.
Figure 43A:
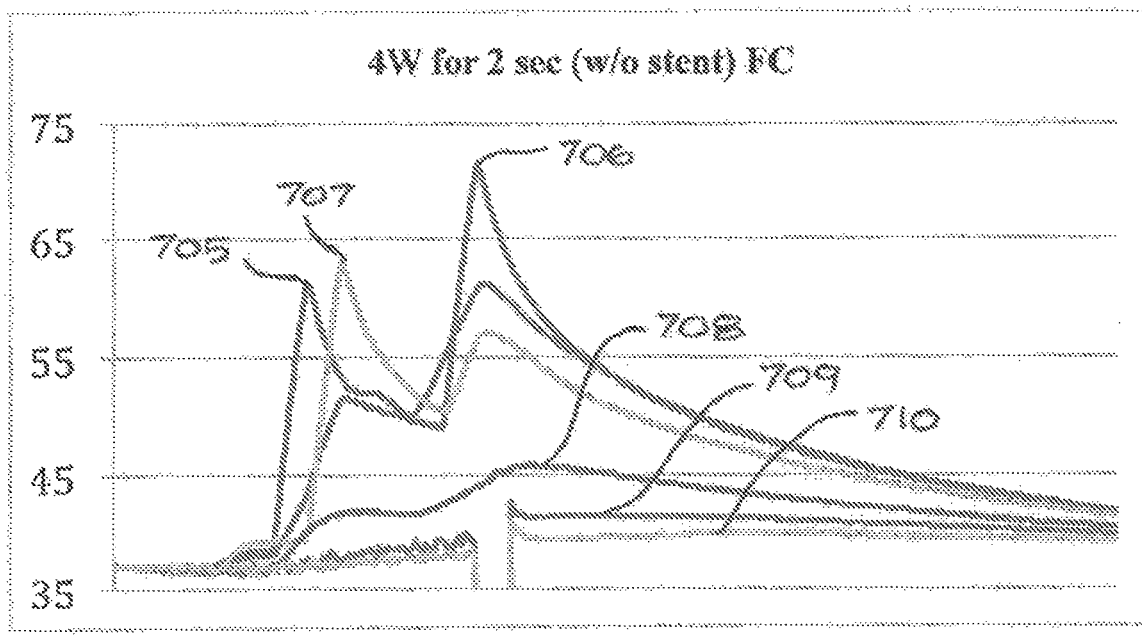
FIGS. 43A and 43B are temperature plots for full-circumferential energy delivery of 4 Watts for 2 seconds, without and with an implanted stent, respectively.
Figure 43B:
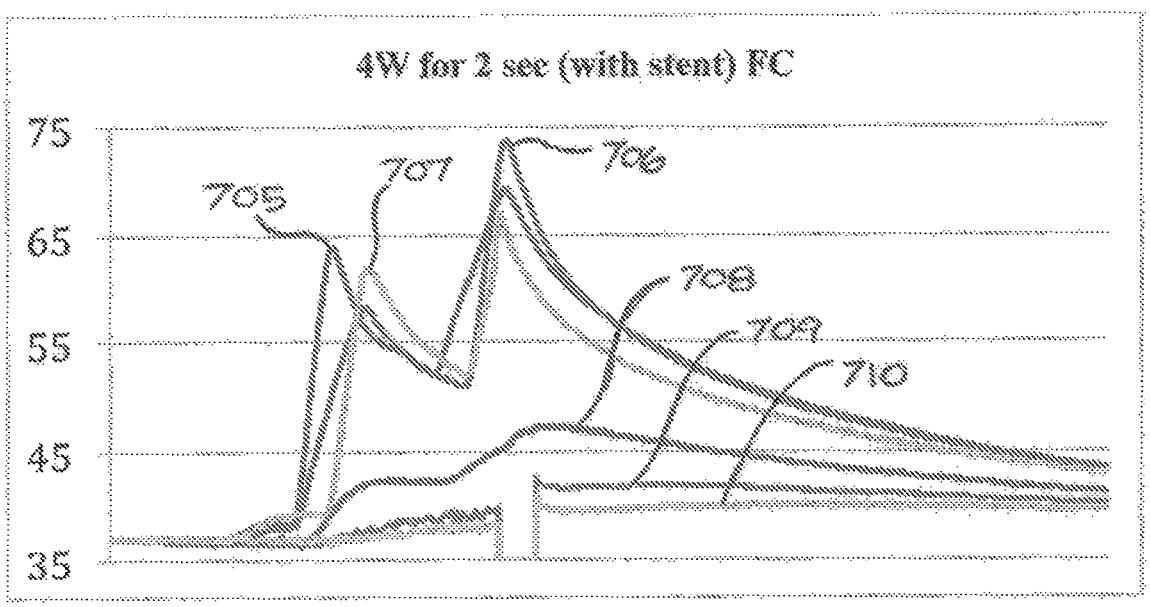
Figure 44A:
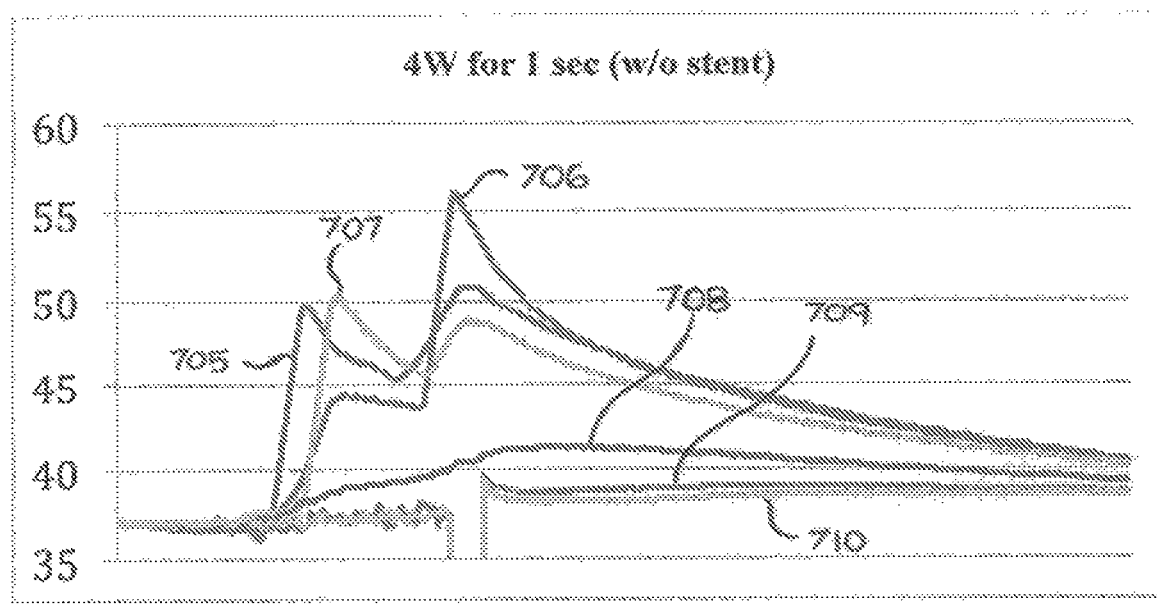
FIGS. 44A and 44B are temperature plots for full-circumferential energy delivery of 4 Watts for 1 second, without and with an implanted stent, respectively.
Figure 44B:
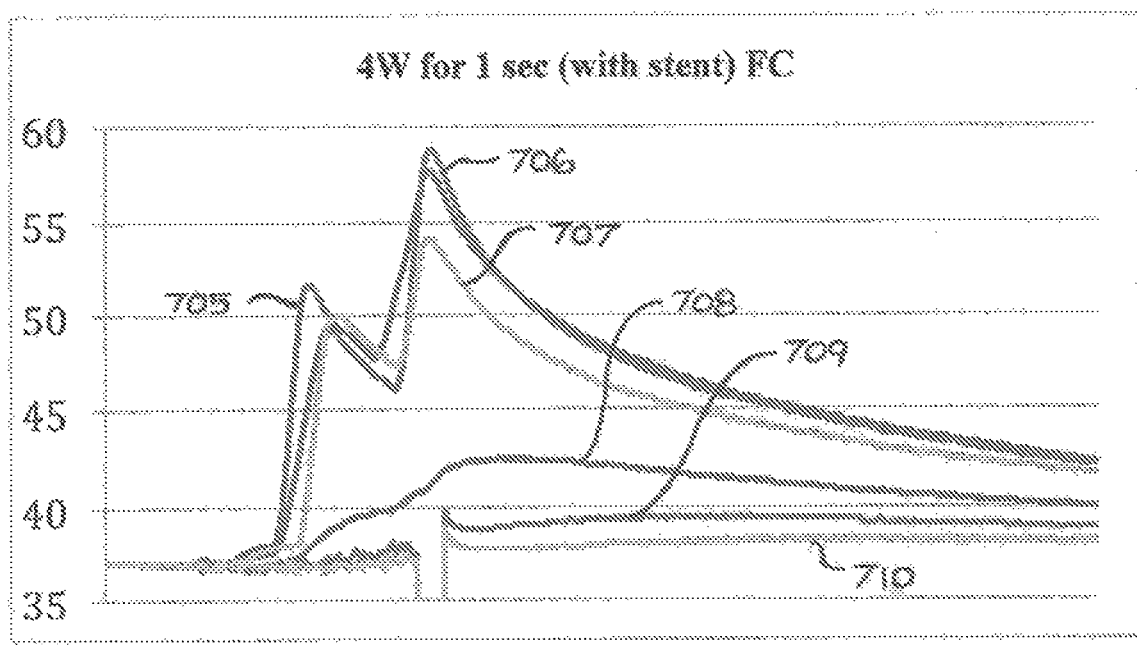
Figure 45A:
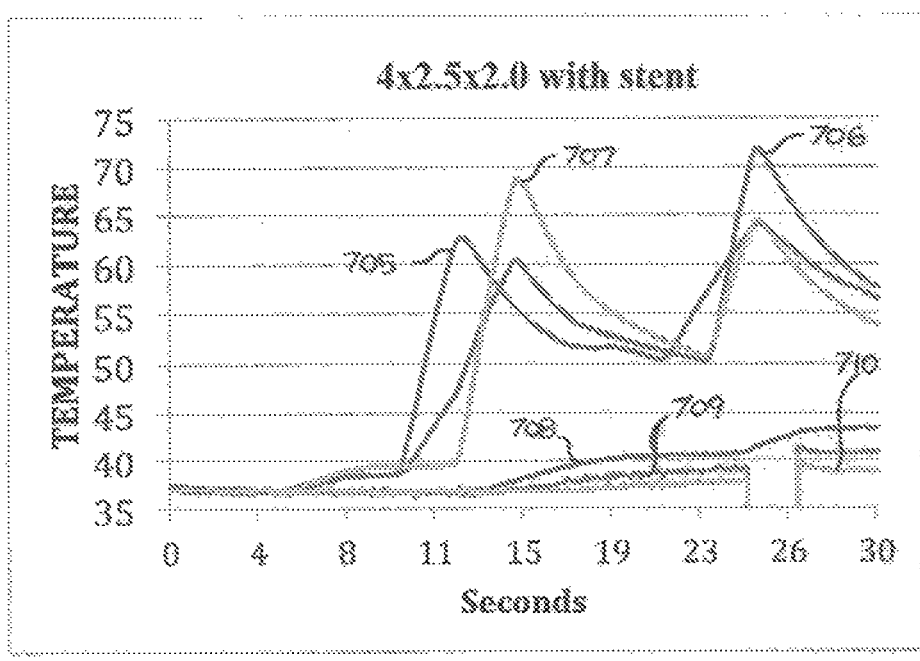
FIGS. 45A and 45B are time-temperature plots for energy delivery of 4 Watts for 2.5 seconds followed by 4 Watts for 1.5 seconds, without and with an implanted stent, respectively.
Figure 45B:
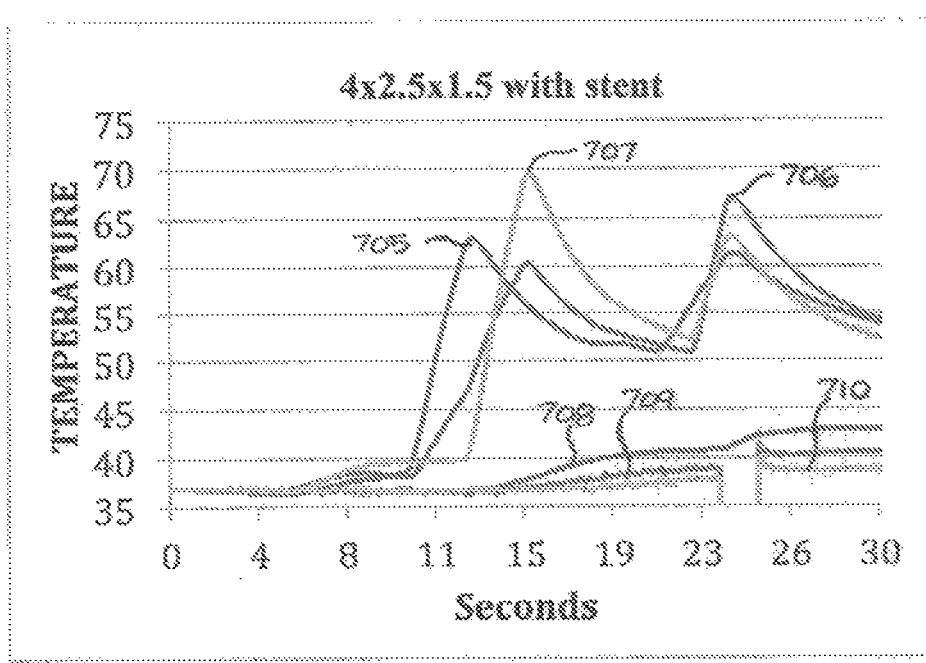
Figure 46:
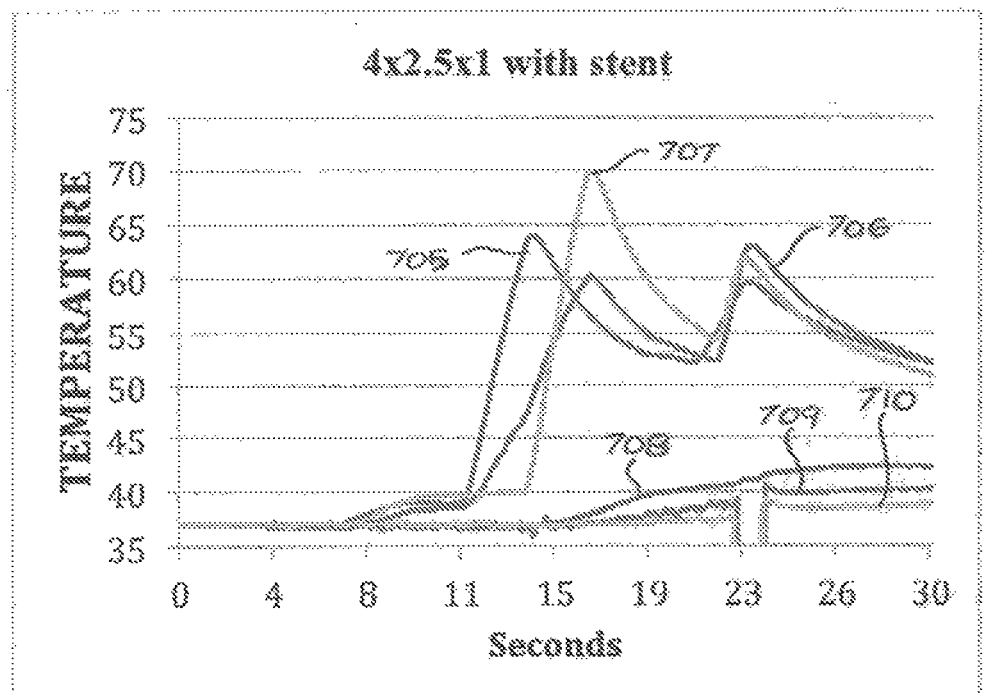
FIG. 46 is a time-temperature plot for energy delivery of 4 Watts for 2.5 seconds followed by 4 Watts for 1 second with an implanted stent.
Figure 47:
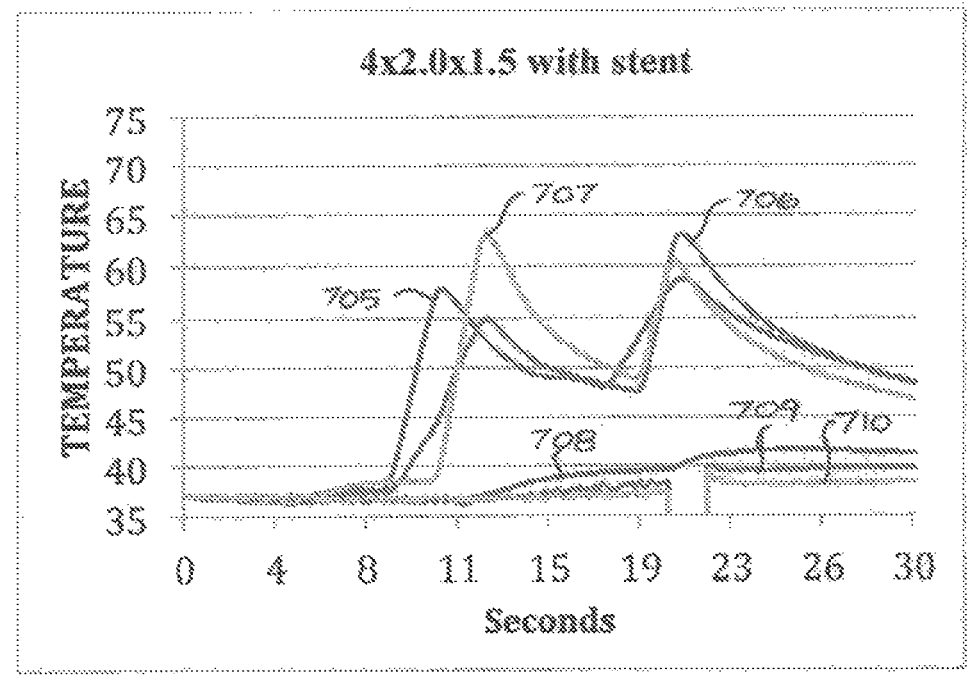
FIG. 47 is a time-temperature plot for energy delivery of 4 Watts for 2.5 seconds followed by 4 Watts for 1.5 seconds with an implanted stent.
Figure 48:
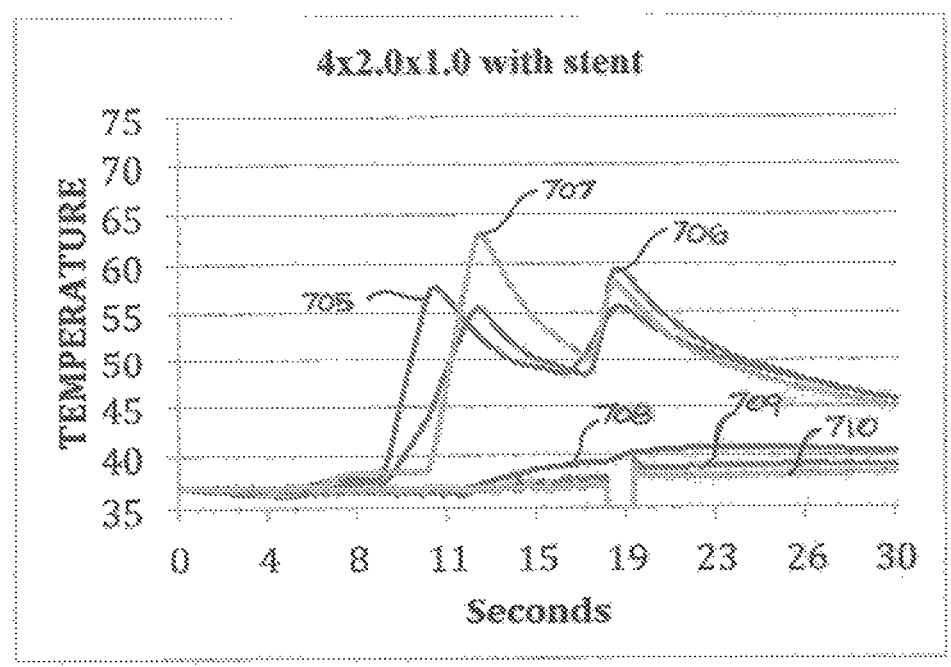
FIG. 48 is a time-temperature plot for energy delivery of 4 Watts for 2 seconds followed by 4 Watts for 1 second with an implanted stent.

Referring to FIGS. 33-35F, energy delivery may be controlled through the use of closed loop control by controller 49 (FIGS. 3, 33) used to regulate energizing of electrodes 634, Most typically the power generator 642 may be controlled to vary voltage such that constant power output is achieved; alternately current may be varied. Further, control loop variable may be selected from one or more of the variables power, impedance, impedance phase angle, and temperature.

Where power is used as a regulated parameter, voltage and current may be measured and voltage may be modulated to achieve a relatively constant power output within a tolerance according to a preset or defined power set point. Optionally the phase angle difference between voltage and current may be included in the power calculation to make power factor corrections based on the phase angle difference. Where impedance is used as a regulated parameter, measured changes in impedance based on changes in tissue temperature and/or tissue state may be used to define a threshold at which power may be halted or allowed to continue where power is modulated to maintain the defined impedance within a tolerance for a period of time.

Where temperature is used as a regulated parameter, an optional temperature sensor 670 or 703 (as shown by FIG. 33A and FIG. 42 respectively) comprised of a thermocouple, thermistor, infrared sensor, or the like, may be used to measure temperature where a defined temperature or temperature range may be used in conjunction with power modulation to maintain temperature in proximity to the sensor 670 or 703 within a temperature range. In one electrode embodiment of the present invention, shown in FIG. 42, one or more of electrode 700 may be mounted to a balloon, such as that of balloon 620 (FIG. 33A), wherein electrodes 700 are comprised of flex circuits further comprised to include electrode conductors 701, a plurality of energy delivery surfaces 702, and a temperature sensing means 703 with conductor 704. Temperature sensing means 703 may be comprised of a thermistor, thermocouple, infrared sensor or the like and may send measurement information to a power control loop through conductor 704. The electrode 700 may be comprised to include radiopaque material, with one preferred approach being a conductive radiopaque material such as gold, platinum, or the like being used to comprise one or more of the plurality of energy delivery surfaces 702. The number and pattern of distribution for electrodes 700 about balloon 620 may be any pattern that provides for a sufficiently uniform means to deliver energy to the tissue treatment zones while avoiding substantial thermal damage to collateral tissue. To aid in the flexibility of the circuit and to aid in minimizing the unexpanded balloon profile, conductors 701 and 704 may be comprised of a substrate that has a thickness as low as about 0.0005 inches with a conductive layer as thin as 0.5 ounces per square foot. One or more surfaces of electrode 700 may be comprised of a polymer for the purpose of adhesion to balloon 620 and/or to provide a barrier between conductors 701, 704 and tissue.

One or more of voltage, current, impedance, and temperature may be used as closed loop control parameters. For example, current may be a closed loop control parameter where power is delivered in the proximity of highly conductive materials, such as metallic stents. In this case it may be prudent to limit current, such as by stopping power delivery when the impedance is at or below a certain/predetermined/predefined level. Or, in the case of a power-limited control algorithm (which will increase current when impedance drops) one may additionally limit the maximum current that is delivered at or below a certain/preset impedance level. This method has the effect of reducing power as impedance falls below a certain/preset threshold. Optionally, one or both of pulse width modulation of energy, and amplitude modulation of energy may be comprised within the means of control. In some instances, the impedance of a stent may vary enough by the nature of its composition (e.g. cobalt chromium versus nickel titanium, polymer, polymer coating, etc.) so as to provide for a range of impedances that may indicate contact with, or proximity to a stent. In some embodiments, impedance may be used to identify the nature of the implanted stent and/or tailor energy delivery accordingly by comparing the known baseline electrical characteristics of unstented neointimal stenotic tissue and comparing those characteristics to that of in-stent stenotic tissue such that measured differences may be attributable to the nature of the implanted stent, whereby the processor and generator may apply control parameters accordingly by taking into account the presence of the stent. In some embodiments, a table of known electrical characteristics of known stent types may be incorporated into energy delivery control algorithms such that an energy delivery profile may either be automatically selected by tissue analysis, or by operator selection. In embodiments where energy delivery may expressly compensate for the nature of an implanted stent, energy delivery may be controlled to avoid thermal damage to stents having temperature-sensitive attributes such as materials of composition, coatings, and the like.

Referring to FIG. 25, impedance measurements using a closed loop treatment controller 366 making use of hardware and/or software of the system processor may facilitate treatment control. Such control over frequency ranges and across multiple electrodes may be utilized to monitor and to verify physical changes such as tissue shrinkage or denaturing of tissue in the application area. This data may be utilized to verify physical changes observed by other intraluminal observation techniques such as ultrasound. Data from impedance measurements 368 combined with inputs from intraluminal measurement devices 370 such as ultrasound can be used to determine electrode selection from a predetermined set of rules of a controller or processor module 372. This type of control system may also be utilized in an automatic mode to diagnose and treat diseased intraluminal tissue, in-stent restenosis, or other such targeted tissue, or to identify and direct energy to a target tissue proximate to a lumen.

Figure 26A:
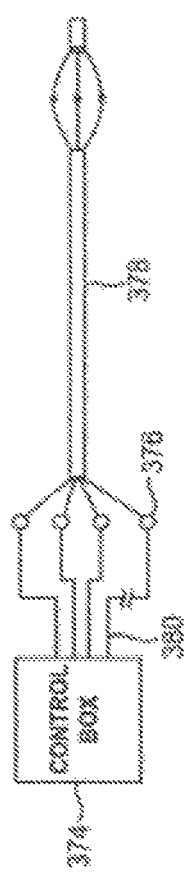
FIG. 26A illustrates the switching mechanism in an external control box.
Figure 26B:
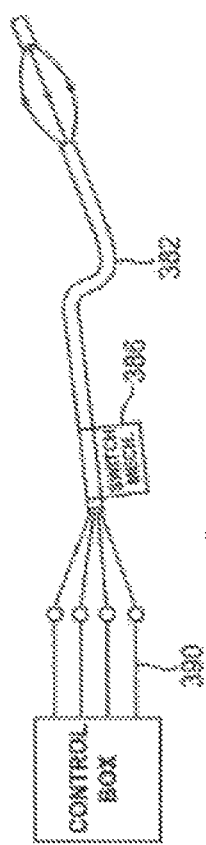
FIG. 26B illustrates the switching mechanism at the distal end of the catheter.
Figure 26C:
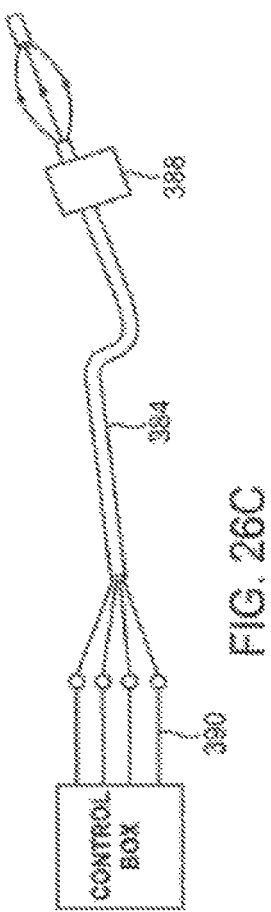
FIG. 26C illustrates the switching mechanism at the proximal end of the catheter.

Implementation of electrode switching may employ any of a wide variety of selective energizing electrode circuits, switch types, switch locations, and the like, some of which are schematically illustrated in FIGS. 26A-26C. Electrode switches can be located in an external instrument or external control box 374, so that one external connector point 376 is provided for each electrode of catheter 378, with one wire per electrode 380 extending to, in and/or along the body of the catheter. Alternatively, electrode switch mechanisms 386, 388 may be embedded in a catheter 382, 384, respectively, either near the proximal end of the catheter for external switching or near the distal end of the catheter for internal switching. A limited number (e.g., 4) wires 390 may run proximally of the switching mechanism, while one wire per electrode may extend distally of the switching mechanism. Connection of discrete electrodes to radiofrequency generator or impedance measuring device can be accomplished by either electromechanical or solid state means.

Switching mechanisms disposed at distal end of catheter may have advantages. If located on the catheter, the switching mechanism can be located at the distal end to decrease the number of wires in the body of the catheter or at the proximal end. In embodiments of switching mechanism located at distal end of catheter the external control circuit optionally communicates with the switching mechanism via the same wires used for impedance measurements. Switching mechanism at the proximal end or other location on catheter may also be employed. The switching mechanism can be located at proximal end or any other location on the catheter if it provides advantage in performance or cost.

Where energy is delivered to a plurality of electrodes 634 (FIGS. 34, 35D) at the same time, electrodes 634 may be powered and controlled either by separate, independent circuits having their own control loops, or by firing one or more electrodes 634 sequentially in time, using the same circuit, in which case the control loop is also closed sequentially.

FIGS. 13-17B show histological results of testing done in animal studies. FIG. 13 shows the application of 1 Watt for 8 seconds post-operatively at seven days, which had a maximum surface temperature of 50° C. in bench top testing, showing mild shortening of smooth muscle at the sites of inserted arrows. FIG. 14 shows the application of 2 Watts for 2 seconds post-operatively at eight days, which also had a maximum surface temperature of 50° C. in bench top testing. FIGS. 15A, 15B show the application of 4 Watts for 1 second at seven days and FIG. 15C post-operatively at thirty days. There are obvious thermal applications corresponding to each electrode (black arrows). There also appears to be thermal alterations to some of the collagenous areas of the vessel wall. This suggests bulk tissue temperatures just slightly over 60° C. FIGS. 16A, 16B show the application of 2 Watts for 4 seconds post-operatively at seven days, and FIG. 16C at thirty days. The slide shows heat therapy at each electrode-tissue interface (black arrow show edges of treatment zones). There is also a corresponding thermal effect deep into the collagenous areas, and gross observations of tissue shrinkage. The figures also show some thermal diffusion into the tissue in between treatment zones that also resulted in collagen denaturing. This indicates that the local areas of heat deposition under the electrodes may have reached 70° C. or higher. Of course, there is a temperature gradient that slopes off in between electrodes and radially away from the electrodes, and deeper into the vessel and surrounding tissue. FIG. 17A shows the application of 3 Watts for 2 seconds post-operatively at seven days and FIG. 17B at thirty days.

In one aspect of the present invention, catheter system 10 may be used to treat luminal target tissues additional to or different than in-stent restenosis as may be understood by referring to FIGS. 7A through 7E. For the purposes of description, the target tissue in the following discussion will be atherosclerosis not located in the stented portion of a body lumen, however, the method of treatment can be understood to represent the method for delivering a therapeutic dose of energy to any target tissue proximate to a luminal wall. In some instances it may be desirable to treat stenotic locations along a lumen where some are in-stent and others are external to the stent, as it is common for diffuse artery disease to not be localized to a stented location. Additionally, the FIGS. 7A-7E show a basket for illustrative purposes; however, the expandable structure may be any of those encompassed by the present invention. As seen in FIG. 7A, accessing of a treatment site will often involve advancing a guidewire GW within a blood vessel V at, and more often distally beyond a target region of atherosclerotic material AM. A wide variety of guidewires may be used. For accessing a vessel having a total occlusion, guidewire GW may comprise any commercially available guidewire suitable for crossing such a total occlusion, including the Safe-Cross™ radiofrequency system guidewire having forward-looking optical coherence reflectometry and radiofrequency ablation. Where atherosclerotic material AM does not result in total occlusion of the lumen, such capabilities need not be provided in guidewire GW, although other advantageous features may be provided. For example, guidewire GW may include a distal balloon to hold the guidewire in place and further inhibit movement of ablation debris and the like. Guidewire GW may be positioned under fluoroscopic (or other) imaging.

Catheter 12 is advanced distally over guidewire GW and positioned adjacent to atherosclerotic material AM, often toward a distal portion of the occlusion as can be understood with reference to FIGS. 7A and 7B. Expandable structure 26 expands radially within the lumen of the blood vessel so that electrodes 50 radially engage atherosclerotic material AM. Expandable structure 26 may be expanded by, for example, pulling a pullwire extending through catheter body 14 to the coupled (directly or indirectly) to distal portion 62 of expandable body 26 (see FIG. 4). Alternatively, an inner catheter body 58 may be moved proximally relative to outer catheter body 14, with the inner catheter again being coupled to the distal portion of the expandable body. Still further alternatives are possible, including withdrawing a sheath from around the expandable body and allowing the expandable body, basket 26 (FIG. 2) to flex radially outwardly, or, by inflating balloon 620 (FIG. 33). In at least some embodiments, whether actuated from the proximal end of catheter 12 or simply by releasing the expandable body, the structural members defining the expandable body may comprise elastic or superelastic materials treated to expand radially outwardly, such as by heat-setting a superelastic Nitinol™ metal, polyimide, or the like. In some embodiments, guidewire GW may be removed after the ablation catheter is positioned and/or the expandable body is expanded. As atherosclerotic material AM is distributed eccentrically about catheter 12, some of electrodes 50 directly engage a luminal wall W, as can be understood with reference to FIGS. 7B and 7C.

Imaging catheter 34 is positioned within a lumen of catheter 12 so that detector 42 extends to adjacent atherosclerotic material AM. The imaging catheter operates within and/or through catheter 12 so as to measure a thickness of atherosclerotic material concentrically about catheter 12 as illustrated in FIG. 7C with measurements often being taken at a plurality of axial locations so as to measure axial variation of the atherosclerotic material AM within the blood vessel, such measurements often progressing proximally. In many cases, atherosclerotic material AM will be distributed eccentrically within the vessel wall as shown in FIG. 7C. It should be noted that no portion of the vessel wall need be completely uncovered by atherosclerotic material for the measurement distribution to indicate that the obstruction is eccentric, as a relatively thin layer of atheroma along one portion or side of the blood vessel may be much different in thickness than a very thick layer of atherosclerotic material on an opposite side of the blood vessel V. In some methods, remodeling and/or ablation of all atheroma along one side may result in electrode/vessel wall engagement only after treatment begins.

In some cases, imaging catheter 34 may allow identification and/or characterization of in-stent restenosis, atherosclerotic materials, plaques, tissues, lesions, and the like from within a blood vessel. For example, imaging catheter 34 may determine an axial and/or circumferential localization of a stenosis for treatment. Where treatments are intended for full or partial stenosis of the lumen, so as to enhance blood flow through the lumen, the treatment may be tailored to provide short term and/or long-term increases in lumen diameter and blood flow. Catheter 34 may be used to provide information similar to that available through histology so as to indicate a composition of a target tissue (by identifying and location of, for example, a stent, smooth muscle cells, a lipid pool, calcifications, etc.) Intravascular ultrasound, optical coherence tomography, intravascular MRI antennas, and other catheter-based imaging systems, or non-invasive imaging modalities such as MRI systems, may be used.

Suitable imaging catheters for use in the present catheter system are commercially available from a wide variety of manufacturers. Suitable technology and/or catheters may, for example, be commercially available from SciMed Life Systems and Jomed-Volcano Therapeutics (providers of intravascular ultrasound catheters), Light Labυ Imaging (developing and commercializing optical coherence tomography catheters for intravascular imaging), Medtronic CardioRhythm, and the like. Still further alternative technologies may be used, including ultra fast magnetic resonance imaging (MRI), and electrical impedance atheroma depth measurements, optical coherence reflectrometry.

The systems, devices, and methods described herein may optionally make use of imaging techniques and/or tissue detector devices which are at least in part (optionally being entirely) disposed outside of the body lumen, optionally being disposed outside of the patient body. Non-invasive imaging modalities which may be employed include S-ray of fluoroscopy systems, MRI systems, external ultrasound transducers, and the like. Optionally, external and/or intravascular tissue detectors may also be used to provide temperature information. For example, a system having an MRI antenna may detect tissue temperatures such that a graphical indication of treatment penetration may be presented on the system display. Tissue temperature information may also be available from ultrasound and/or optical coherence tomography systems, and the temperature information may be used as feedback for directing ongoing treatments, for selecting tissues for treatment (for example, by identifying a hot or vulnerable plaque). Additionally, as shown in FIG. 33A and FIG. 42, one or more temperature sensors 670 or 703 may be mounted on the expandable structure 620 proximate to energy delivery surfaces 634 or 702 to provide tissue temperature sensing during the delivery of therapeutic energy dosages to the targeted tissue area proximate to a lumen.

As with positioning of guidewire GW and advancement of catheter 12, positioning of sensor 30 of imaging catheter 34 may be facilitated by fluoroscopic or other imaging modalities. Location of sensor 36 relative to expandable structure 26 may be facilitated by radiopaque markers of catheter 34 adjacent sensor 36, and by the radiopaque structure (or corresponding radiopaque markers placed on or near) expandable structure 26, and/or by the use of electrodes comprised to include radiopaque material. By way of example gold and platinum are tow common radiopaque materials that may be desirable choices because they are also conductive, however, any biocompatible radiopaque material may be used.

By expanding expandable structure 26 within blood vessel V, optional proximal and distal barriers 66, 68 (FIG. 4) may form an at least partially, and preferably a substantially isolated environment within the blood vessel. That environment may be adapted to improve subsequent remodeling and/or ablation by aspirating blood from a port of aspiration lumen 22 disposed between proximal and distal barriers 66, 68, and by irrigating the isolated environment with a desired fluid, as described above. When provided, aspiration and/or irrigation may be performed, optionally simultaneously, so as to generate a flow within the controlled environment for removal of any vaporization gases, ablation debris, and the like.

Figure 7D:
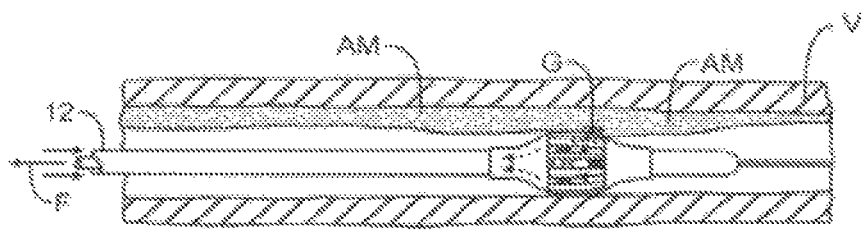

Referring now to FIGS. 7C and 7D, circumferential imaging often indicates that treatment energy should be targeted to an eccentric portion or region R of the vessel wall W. To aid in registering the electrodes with the circumferential target tissue distribution, one strut of expandable structure 26 has an identifiable image, allowing the strut to serve as a rotational alignment key. Alternately, a radiopaque marker may be used for an expandable structure comprising a balloon. Registering the electrodes may be achieved using intravascular imaging such as intravascular ultrasound (IVUS), optical coherence tomography ("OCT"), or intravascular MRI, optionally using external imaging such as fluoroscopy, magnetic resonance imaging ("MRI"), etc. Electronic registration may also be used. In response to this information, radiofrequency energy is directed to electrodes within region R. There actively energized electrodes define a subset of the overall array of electrodes, and selection of this subset of electrodes may be implemented using a controller as described herein.

Figure 7E:
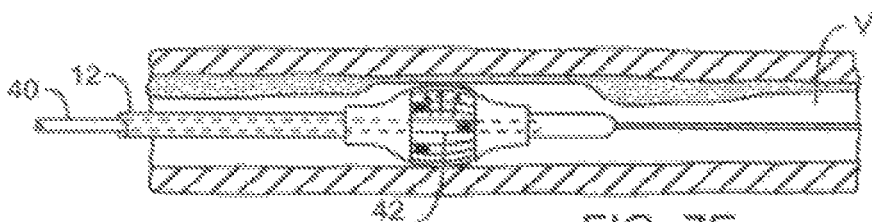

Referring now to FIG. 7E, as described above, it may not be necessary to completely remove all stenotic material from within the blood vessel. Providing an open lumen having an effective diameter of as much as 80% or more of a nominal native lumen diameter may be sufficient. Remodeling treatments may provide acute effective open diameters in a range from about 30% to about 50%. In some embodiments, thermal treatment caused to the target tissue with the energized electrodes or other energy directing surfaces may result in subsequent resorption of the target tissue so as to provide further opening of the vessel after termination of treatment through the healing process, as the data in Table 3 indicates.

In some embodiments, the expandable structure may remain expanded against the lumen wall W while the catheter 12 moves within the lumen (a blood vessel for example), the catheter often being drawn proximally during or between energy treatments. Alternatively, the expandable structure may be repeatedly contracted, axial movement of the catheter 12 employed to reposition the expandable structure, with subsequent expansion of the structure at each of a plurality of treatment locations along the targeted area proximate to the luminal wall. Repeated intravascular imaging or other measurements circumferentially about catheter 12 may be employed, with the energy often being halted temporarily so as to allow an image to be acquired intermittently during a procedure. A final image may be taken to verify energy treatment has been successful.

Figure 10:
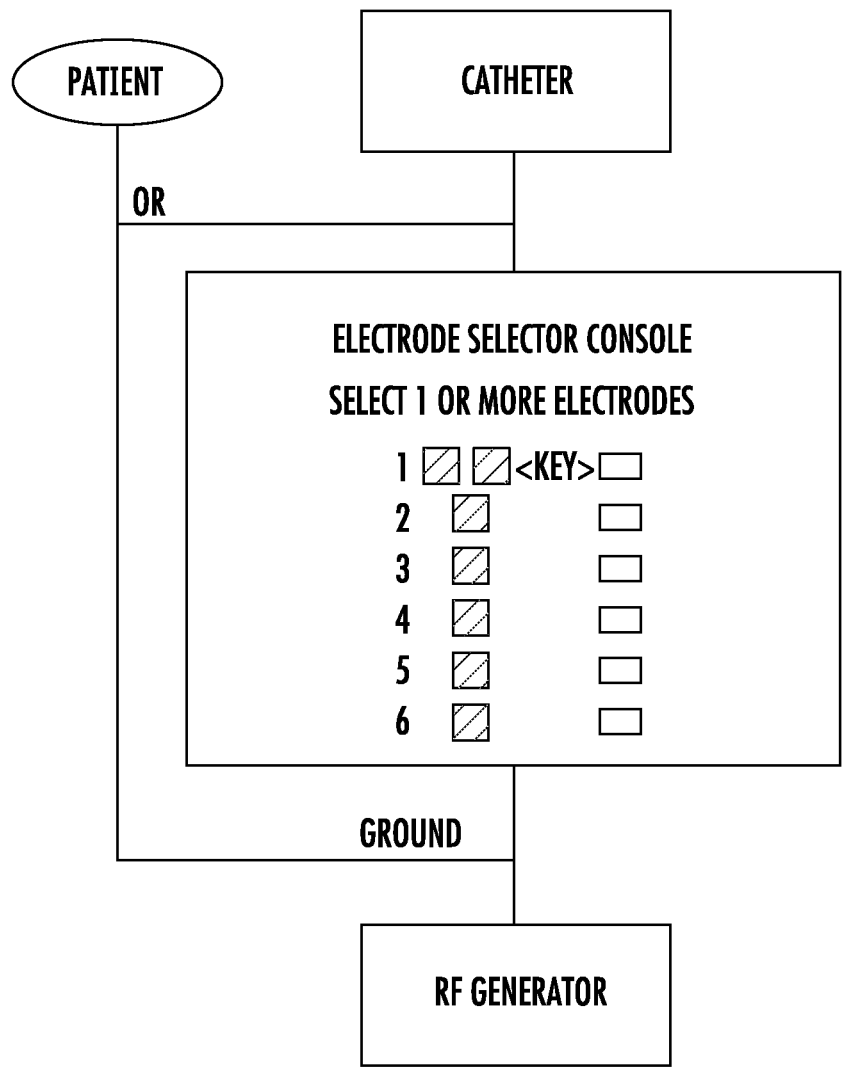
Figure 11:
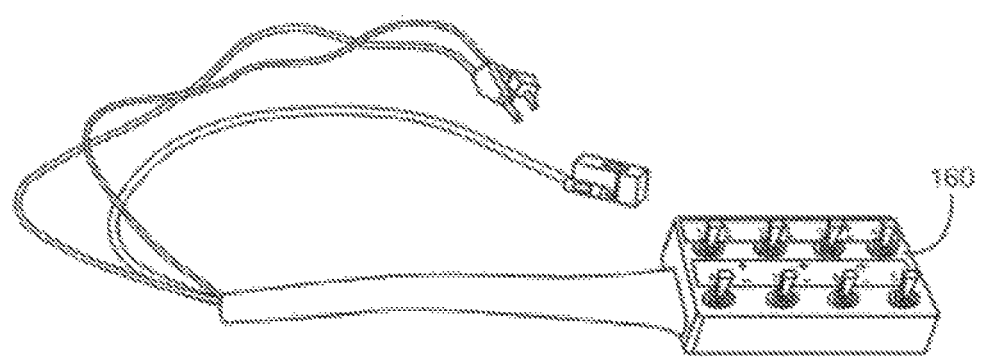
FIG. 11 illustrates an alternative controller for selectively energizing electrodes in the system of FIG. 2.

Referring now to FIGS. 8 and 9, alternative controllers 92a, 92b selectively energize electrodes of catheter 12 with radiofrequency power supplied from a radiofrequency generator 94. A wide range of radiofrequency energy types may be employed, including burst of 500 Khz, different types of waveforms, and the like. In controller 92a, a simple dial 96 is turned to point to a desired electrode pair to be energized. Optionally, a "key" electrode may be registered with the intravascular imaging system, either electronically or by providing an electrode, electrode support member, or attached marker that presents a distinct image on the intravascular imaging display. This simplifies selection of one or more eccentric electrode pair along a targeted area. Advantageously, catheter 12 need not be rotated into a proper orientation to accurately deliver therapeutic energy eccentrically to tissues proximate to the circumference of a lumen wall. Controller 92b includes similar capabilities, but allows the operator to select multiple electrodes for driving bipolar radiofrequency energy therebetween, providing greater flexibility in allowing multiple electrodes to be simultaneously energized. Monopole control arrangements similar to those of FIGS. 8 and 9 may also be employed, as can be understood with reference to FIG. 10. Patient grounding may be effected by a patient grounding plate, a ring electrode 2 to 5 cm proximal to basket 26, or the like. Once again, no catheter rotation is required to orient an active side of the catheter adjacent to the targeted tissue since various eccentric orientations can be selected through the electrode selection controller.

Figure 12A:
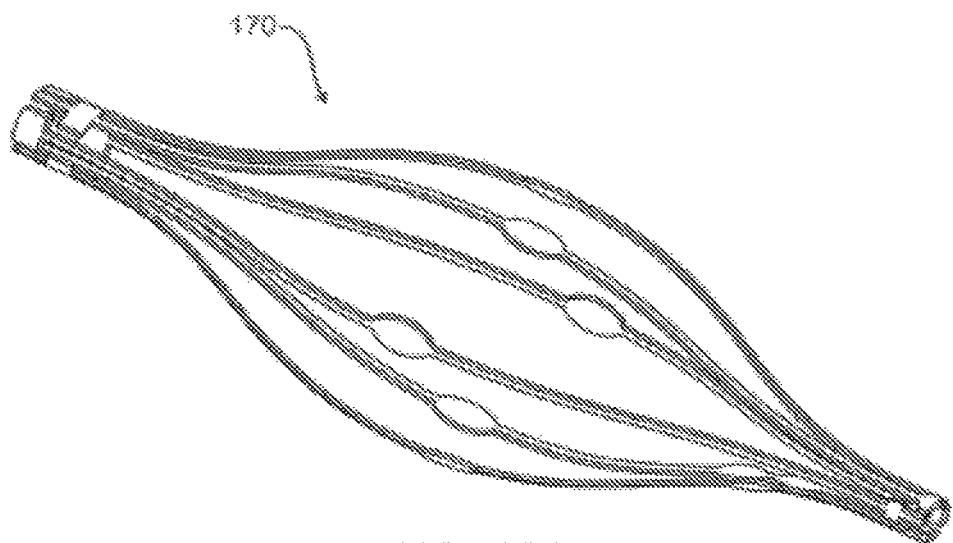
FIGS. 12A-H illustrate an alternative basket structure formed with independent struts having a localized enhanced width for use as an electrode surface, along with components thereof.
Figure 12B:
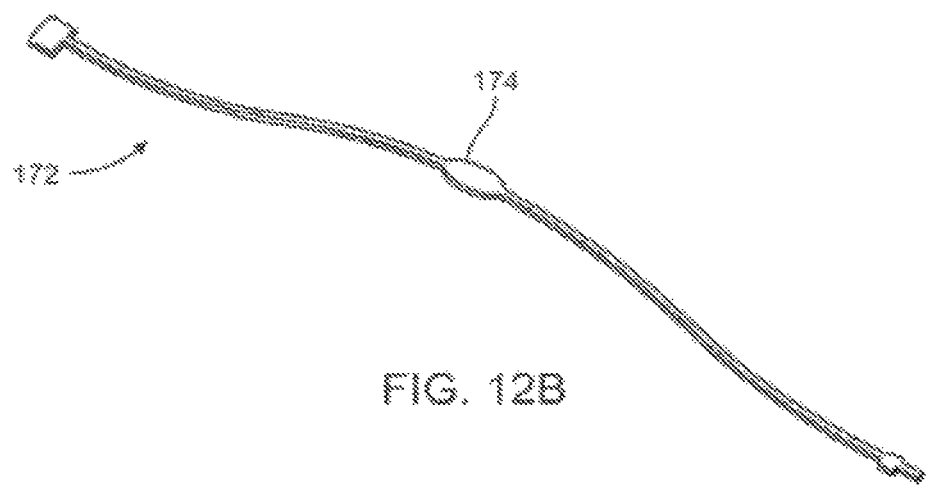
Figure 12C:
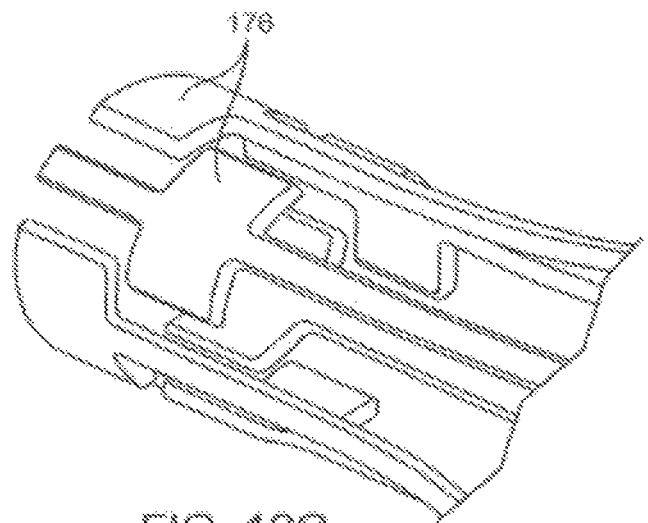
Figure 12D:
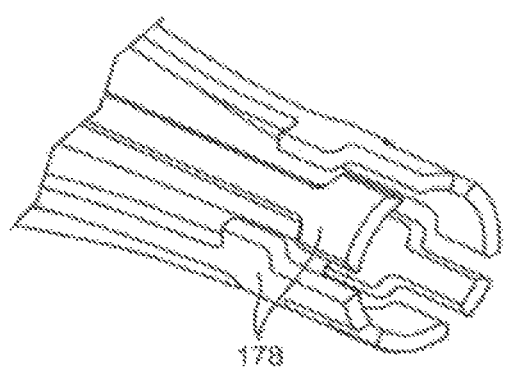
Figure 12E:
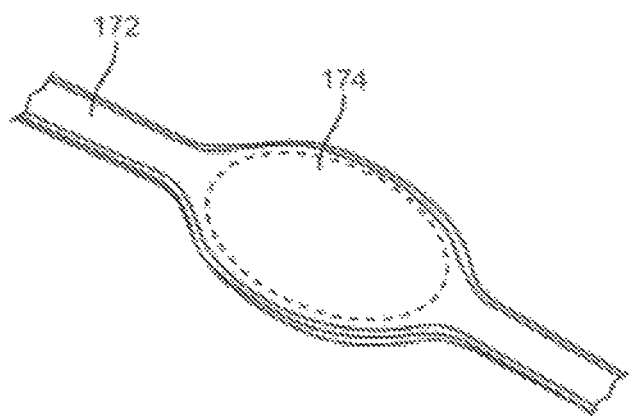

An exemplary self-expandable basket is illustrated in FIGS. 12A-12H. As can be understood from these drawings, electrodes may be fabricated as part of the struts 172 from which the basket is formed, for example, using a radially outwardly oriented surface of a localized widening 174 of each strut disposed in axially central portion of the strut, as can be seen in FIGS. 12B and 12E. Each arm may be formed from one piece of material, optionally comprising a Nitinol™ nickel-titanium shaped memory alloy, with the struts optionally being laser cut from a Nitinol™ tube. The electrode/basket may be, for example, coated with a high temperature polymer such as a polyimide. Electrodes 174 may be formed by inhibiting coating or removing coating from the desired portion of the associated strut 172 (as illustrated in FIG. 12E) so that the electrode surface is exposed for contact with tissue. At least the active electrode surfaces may be coated with a highly conductive metal such as gold, silver, an alloy of copper, or the like, and the coating will preferably maintain and withstand flexibility of the basket structure, with coating materials optionally being rolled or the like. By limiting the conductive electrode to a properly configured (often radially outwardly oriented), electrical coupling between the electrode and blood or other conductive fluids within the lumen may be limited. The struts may be separated from each other and structurally supported with an insulated material such as ultraviolet ("UV") cure or heat shrink sleeve, a polyethylene, Nylon™ to form basket 170. Many imaging modalities (including intravascular ultrasound, optical coherence tomography, intravascular MRI, and the like) may be at least in part blocked or degraded by positioning the image detecting structure within a metallic structure such as a basket formed of Nitinol™. Hence, there may be advantages in producing alternative expandable structures such as baskets comprising plastics or a polymer. Further, in light of the heat generated by the electrodes of the systems described herein, it may be advantageous for such polymer basket structures to comprise a high temperature polymer such as a polyimide. Alternative basket structures may comprise HDPE, PET, Nylon™, PEBAX™, and the like; the basket may be formed by cutting struts from a tube of the polymer material.

Figure 14E:
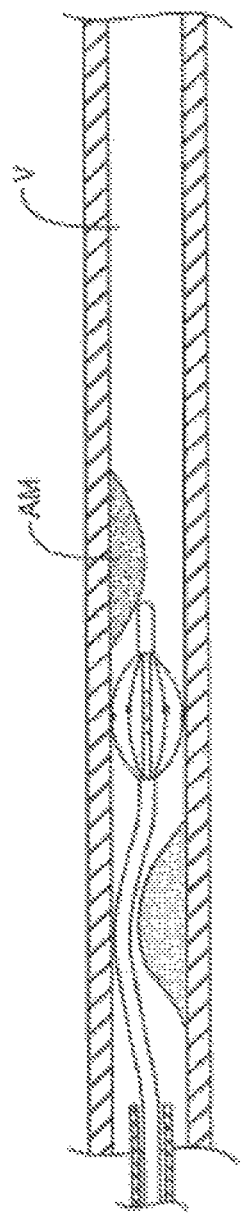

Exemplary treatment methods are illustrated in FIGS. 14A-14H. In FIG. 14A, the catheter system 260 includes a basket covering sheath 262 over an atherosclerotic material detecting and treating catheter 264 as described above. In this embodiment, outer basket sheath 262 radially restrains the basket 266, which is biased to expand radially when released from the outer sheath, as illustrated in FIG. 14B. In some embodiments, the basket may be expanded after the outer sleeve is retracted, such as by pulling pullwires, rotating one portion of the catheter relative to the other, or the like. Regardless, as the basket expands within the vessel V, electrodes 50 of the basket engage the surrounding vessel wall. An imaging transducer near basket 266 of an imaging catheter disposed in a lumen of the treatment catheter evaluates the vessel V, and the detection/treatment catheter system 264 is pulled proximally along the artery or vessel V.

Figure 12F:
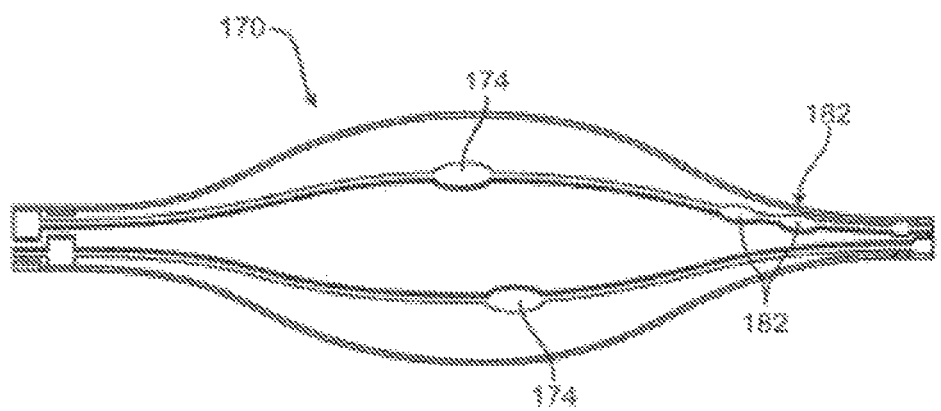
Figure 12G:
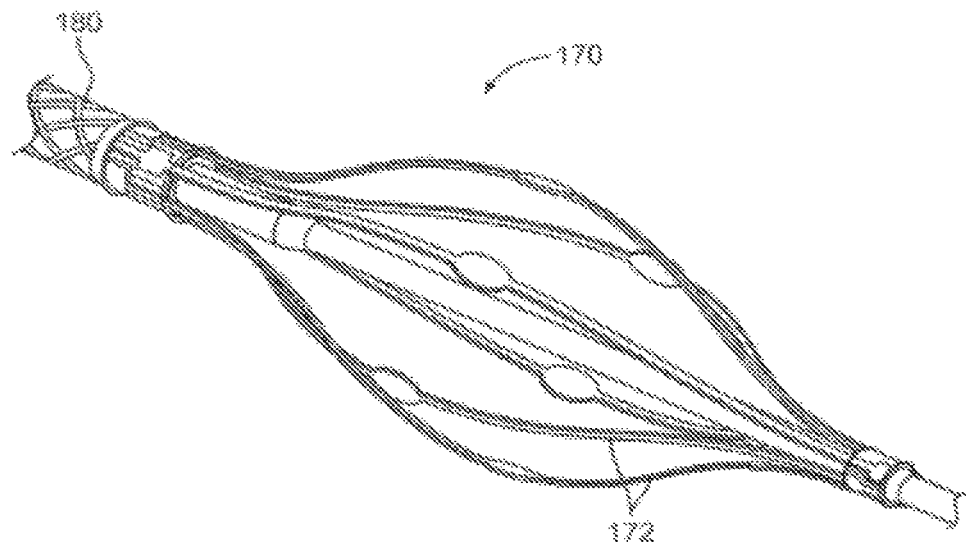

Each strut 172 may be used to conduct energy between electrode surface 174 and an electrical conductor extending proximally from the strut toward a controller. Proximal pads for connecting such conductors are illustrated in FIG. 12C, while distal structural pads 178 are illustrated in FIG. 12D. Adjacent electrodes 174 may be axially offset or staggered as can be seen in FIG. 12F. Insulating coating along each strut 172 may be inhibited or removed from an inner surface of proximal pads 176 so as to facilitate connecting of an associated conductive wire, such as by spot welding or other attaching means. Alternative polymer or non-polymer insulating materials may also be used, including parylene coatings, while alternative methods or attaching struts 172 to a catheter body may be employed, including adhesive bonding using insulating UV cure, embedding the pad structures in polyethylene or other polymers. Exemplary structures for fixing struts 172 of basket 170 to a catheter body 180 are illustrated in FIG. 12G.

Figure 12H:
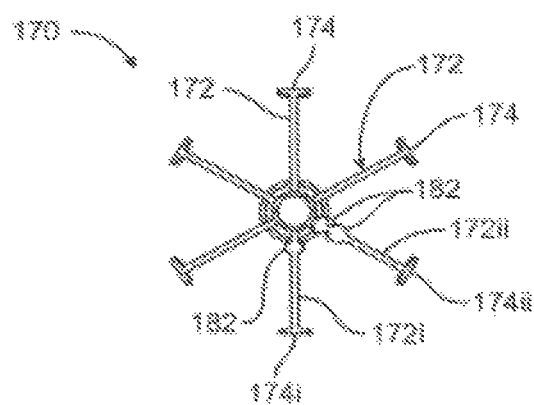

Referring now to FIGS. 12F and 12H, an alternative indicia providing a distinguishable image for rotationally registering selected electrodes 174 of basket 170 to images or other tissue material measurements can be understood. In this embodiment, an electrode 174i referenced as electrode 1 may have a radiopaque marker 182 disposed on the associated strut 172i. A strut 172ii supporting an associated second electrode 174*ii* may have two radiopaque markers 182 provide a circumferentially asymmetric count indicator allowing all electrodes to be referenced without ambiguity. The shape of electrodes 50 may vary, for example, electrodes 174 may be wider than other portions of struts 172 as illustrated in FIGS. 12A-G.

In some embodiments, remodelling may be performed using irrigation and/or aspiration flows. In many such embodiments, an irrigation port directs fluid, such as a saline solution, from an irrigation lumen to an interior of the basket. An aspiration port may provide fluid communication between an aspiration lumen and an interior of the basket. One or both of these fluid flows may be driven continuously, or may alternatively pulsate before, during, and/or after treatment. In some embodiments, aspiration and/or irrigation flow may occur acutely or concurrently so as to circulate between the irrigation port and the aspiration port. Optionally, the flow may carry debris to the aspiration port, where the debris may be evacuated through the aspiration lumen. There may be coordination between the irrigation system and the aspiration system such that the irrigation fluid may remain confined in an area closely adjacent the basket so as to inhibit embolization of debris when the basket is expanded within the blood vessel. Such coordination, for example, may inhibit distal movement of debris, and/or may obviate any need for a distal and/or proximal barrier or membrane. In some embodiments, the circulation of fluid between an irrigation port and as aspiration port may create an effectively bloodless environment adjacent the electrodes to facilitate treatment, imaging of tissue, or other aspects of therapy.

Figure 14F:
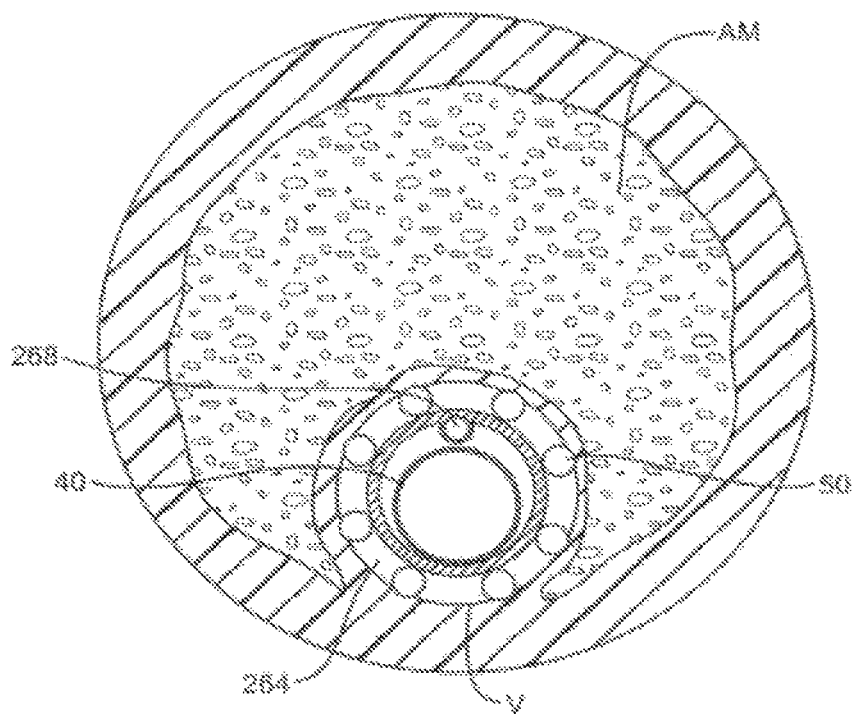
FIGS. 14F-H are cross sectional views taken across a body lumen and treatment device to show additional aspects of the eccentric treatment methods and devices.
Figure 14G:
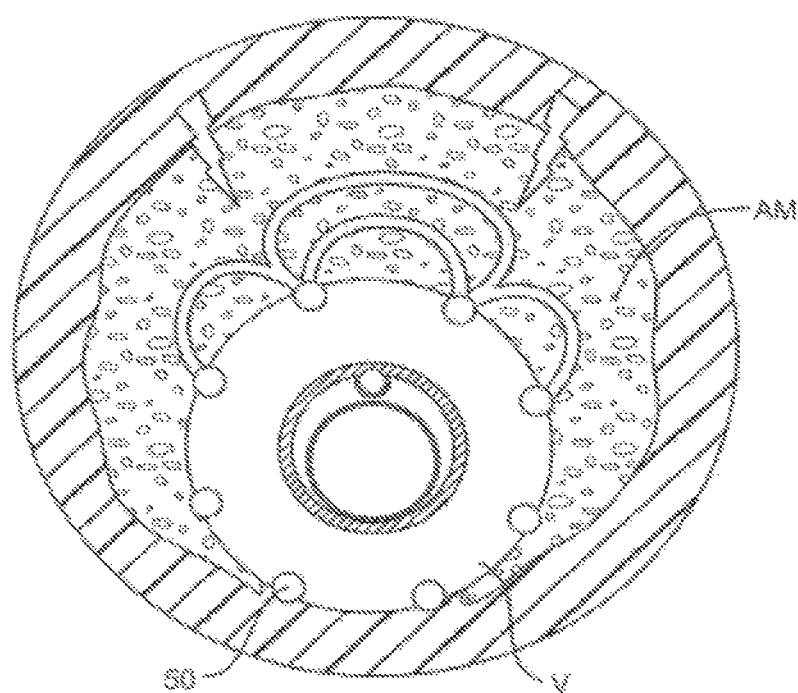
Figure 14H:
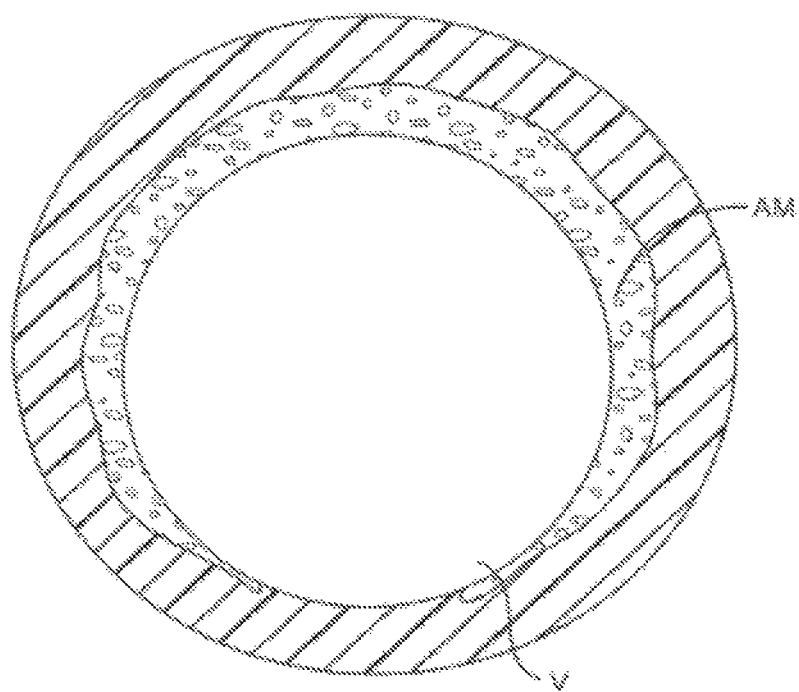

When the imaging catheter detects atherosclerotic material AM as illustrated in FIG. 14C, an appropriate subset (possibly including only a single electrode 50) is activated to remodel the atherosclerotic material AM, as illustrated in FIG. 14D, and the open vessel lumen size increases moderately during treatment. The catheter is pulled proximally to the next atheroma, which is again detected and treated. A cross section of the limited open lumen prior to treatment is schematically illustrated in FIG. 14F, which also illustrates a saline flush or irrigation lumen 268 of the catheter 264. Treatment energy and the moderate increase in the open lumen diameter of the vessel V are schematically illustrated in the cross section of FIG. 14G. After a healing response gradually increases the open lumen diameter, the longer term open lumen results schematically illustrated in FIG. 14H may then be provided.

Figure 15A:
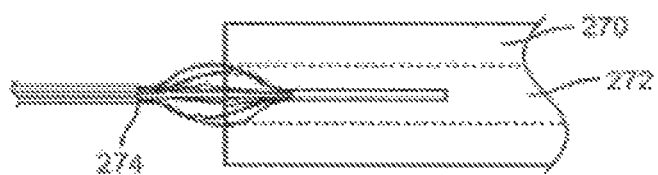
FIGS. 15A and 15B illustrate an eccentric treatment device and method in a gelatin artery model.
Figure 15B:
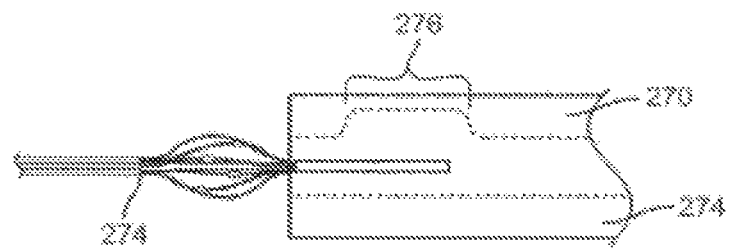

Referring now to FIGS. 15A and B, eccentric material removal in a gelatin artery model 270 are presented. Prior to the test, the artery model includes a consistent lumen 272 as seen in FIG. 15A. A test eccentric treatments catheter 274 having an expandable basket supporting a circumferential array of electrodes is introduced into lumen 272, with the expandable basket supporting the electrodes in engagement with the luminal wall. Selected electrodes of test catheter 274 were energized so as to eccentrically treat the gelatin artery model 274, thereby effecting eccentric remodeling of the gelatin model, in this case by removing and eccentric volume 276 from along one side of lumen 272. The orientation and amount of the material removed was controlled by selectively energizing electrodes of test catheter 274.

Still further alternatives are available. For example, another way to employ radiofrequency energy to tissue proximate to a lumen may be to energize a plurality of the adjacent electrodes with differing radiofrequency signals so as to employ the adjacent electrodes as a phase arrays. A phase array may direct or steer an electromagnetic signal in a desired direction using constructive and destructive interferences between signals of adjacent elements of the array. By controlling phases of the adjacent signals, a phase array of electrodes may provide a focused and/or steerable radiofrequency signal.

Along with controlling steering and directionality, adjusting phases of adjacent radiofrequency electrodes may allow focusing of some or most of the radiofrequency energy at a desired depth D inside the treatment zone while inhibiting radiofrequency energy delivery between the electrode surfaces and depth D using constructive and destructive interference between the signals. For example, such a system may be employed to preserve the cap of a plaque so as to reduce restenosis. Inhibiting heating or the cup while focusing energy toward an internal portion of the plaque may lower an immune response to heat that could otherwise lead to restenosis. Hence, inhibiting heating of the cap may reduce restenosis. Alternatively, an effective dose of energy may be directed to tissues at a depth D that is targeted at a distance from the luminal wall.

Figure 17A:
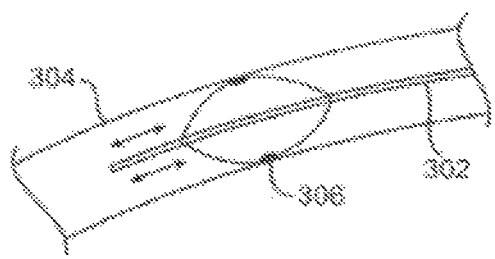
FIG. 17A illustrates physical targeting within vessel by longitudinal movement.
Figure 17B:
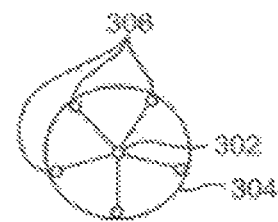
FIG. 17B illustrates physical targeting within vessel by radial electrode activation.
Figure 17C:
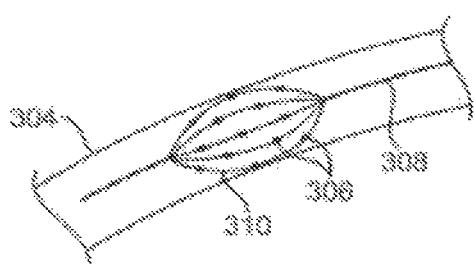
FIG. 17C illustrates physical targeting by activation of radial and longitudinal electrode combinations.

As can be understood with reference to FIG. 17A-17C, physical targeting of tissue can be accomplished by positioning of electrodes by moving longitudinally in vessel until positioned in the vicinity of targeted tissue. As schematically illustrated in FIG. 17A, axial movement of a distal end of probe in the form of a catheter 302 within a body lumen 304 allows different axial portions of the lumen wall to be targeted for analysis and treatment. An additional method to physically target eccentric disease in a radial manner is to apply bipolar energy selectively to specific electrodes 306 so as to direct energy through the targeted tissue, as can be understood with reference to FIG. 17B. In some embodiments, radial and longitudinal physical targeting may be effected by selective activation of electrodes distributed both radially and longitudinally on an expandable body 310, as illustrated in FIG. 17C.

Figure 18:
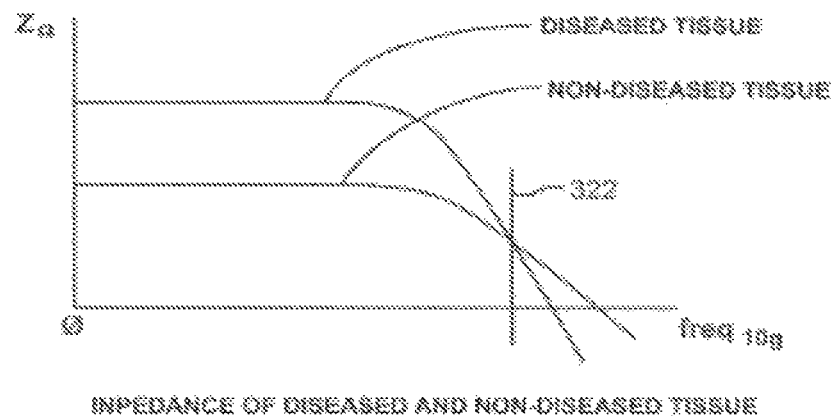
FIG. 18 illustrates electrical impedance versus frequency characteristic of diseased and non-diseased tissue.
Figure 19:
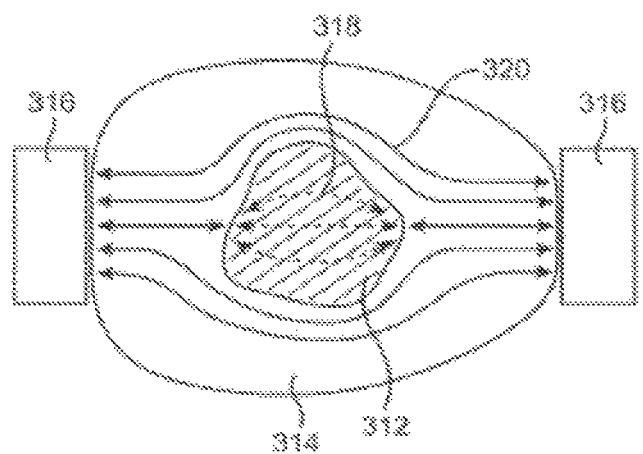
FIG. 19 illustrates shielding of high impedance tissue from electrical current by surrounding lower impedance tissue.

Frequency targeting of tissues is illustrated in FIGS. 18 and 19. As graphically illustrated in FIG. 18, different tissue types have different characteristic electrical impedances that cause the tissue to absorb energy of certain frequencies or frequency ranges more readily than others. By applying energy at the specific frequency or range of frequencies that the tissue is more conductive, energy penetrates the tissue more readily. In general, it has been shown that samples of diseased tissue exhibit higher impedance characteristics than samples of healthy tissue. As illustrated in FIG. 19, in the case where a diseased area of tissue 312 is surrounded by relatively healthy tissue 314, the healthy tissue is likely to shield the diseased tissue from electrical current flow due to the lower impedance of the healthy tissue. Hence, minimal (or less than the desired) current flow 318 may pass through diseased tissue 312, and heavier current flow 320 may be seen in low impedance healthy tissue 314 when bipolar current is transmitted between electrodes 316. Typically, the frequency ranges in which tissue impedance varies to a useful degree occur between 100 kilohertz and 10 Megahertz.

Frequency targeting seeks to deliver more energy to the diseased tissue by determining the frequency or range of frequencies at which the impedance of the diseased tissue is equal to or less than that of the healthy tissue, such as by operation at or above a threshold frequency 322 as illustrated in FIG. 18. Energy delivered at the specified frequency or range of frequencies may cause more heat to be dissipated in the diseased tissue than energy delivered outside of those specific frequencies.

Figure 20:
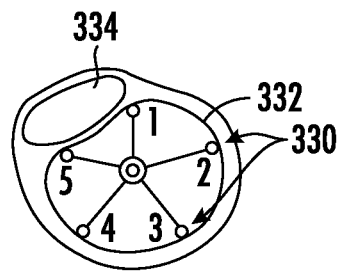
FIG. 20 illustrates electrical impedance measurement utilizing multiple radically spaced electrodes.

The use of impedance measurements to determine a location and/or state of tissue may be generally understood with reference to FIG. 20. First, impedance measurements utilizing an array of radially spaced electrodes 330 within lumen 332 may be used to analyze diseased tissue 334. Impedance measurements between the electrodes of the array, and particularly impedance measurements between pairs of adjacent electrodes (and/or between pairs of separated electrodes), may differ when the current path passes through diseased tissue 334, and when it passes through healthy tissues of the luminal wall. Hence, impedance measurements between the electrodes on either side of diseased tissue 334 may indicate a lesion, while measurements between other pairs of adjacent electrodes may indicate healthy tissue.

The state of a tissue can be affected/changed by temperature, for instance, lipids start denaturing at 85° C. and turn into a new state, fatty acids, which may be 90% more compact in volume than the original lipids. Alternatively, impedance may be used to identify and target amongst tissue types with or without disease, for example, a target tissue may be identified and treated based on differing characteristics from adjacent tissues. If one knows the temperatures of state change for a tissue, and the impedance of the different states of the tissue, then by measuring the tissue impedance, it is possible to detect a state change, and/or to estimate what the temperature is, thereby allowing one to monitor the progress of the therapy. E.g.: if impedance of lipids were 100 Ohms, and impedance of fatty acids were 90 Ohms (here using hypothetical values), and knowing that lipids turn into fatty acids at around 85° C., then detecting a change in impedance from 100 Ohms to 90 Ohms indicates that the lipids turned into fatty acids and therefore that the temperature should be around 85° C. Analysis of tissues proximate to a lumen may use specific frequencies to verify a type and condition of tissue based on electrical impedance measurement. Normal use will include the discovery and characterization of diseased tissue using intraluminal ultrasound or other methods. Measurement of tissue electrical impedances over radially spaced electrodes may allow for verification of the existence of tissue states or types and provide knowledge of the location of the electrodes relative to specific tissue. As a further alternate, FIGS. 35D, 35E depict how the location and relative proximity of an implant structure 652 as it relates to an electrode 634A-634F may be sensed and used to aid in controlling the delivery 653. As is shown in FIG. 35E at the point of CONTACT or near CONTACT, energy 653 may cease to be delivered as electrodes 634F and 634A come into contact or near contact with implant structure 652 as system 10 (FIG. 33) is used to treat in-stent restenosis.

Figure 21:
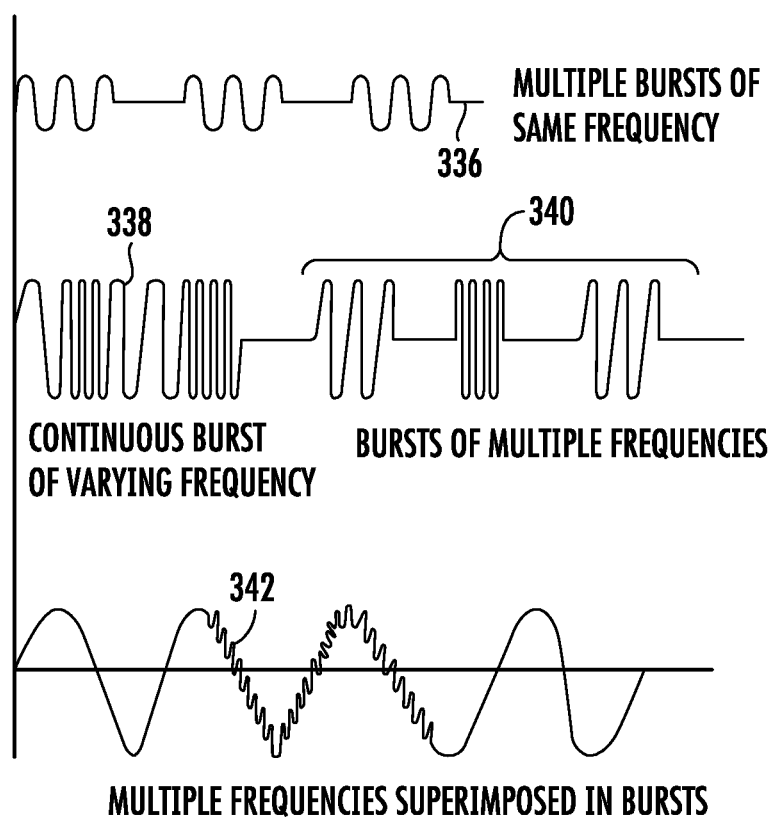
FIG. 21 illustrates variations of multiple frequency therapy.

Multiple frequency therapies and signals are schematically illustrated in FIG. 21. Therapy may consist of the application of electrical energy at a single frequency or at multiple frequencies. Depending on the composition of the target tissue and surrounding tissue, the optimum treatment may consist of a single frequency to target a single tissue type, multiple frequencies to target multiple tissue types, or multiple frequencies applied to a single tissue type. Multiple bursts of the same frequency 336, varying frequencies, such as a continuous burst of varying frequency 338, bursts of multiple frequencies 340, and multiple frequencies superimposed (optionally in bursts 342) may be employed.

Multiple frequencies can be applied in any sequence from any combination of electrodes in contact with the target tissue or surrounding tissue. Multiple frequencies can be applied as discrete frequencies or can be applied as a frequency sweep across a range in a linear, logarithmic, or other manner.

Figure 22:
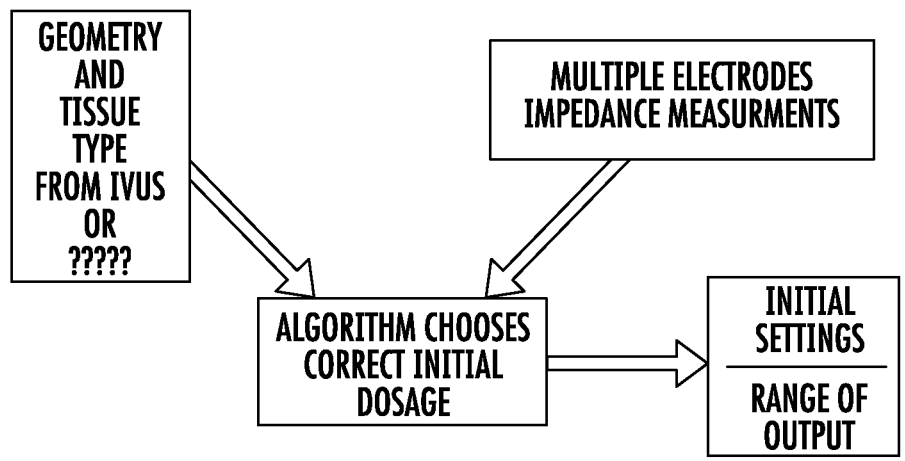
FIG. 22 illustrates use of physical tissue characteristics from external sources combined with electrical impedance measurements to determine a desired or optimum energy setting.

An energy control arrangement is schematically illustrated in FIG. 22. In general, impedance and physical tissue characteristics may be utilized to set the output or treatment parameters. Geometry and tissue type may be determined as described herein using IVUS or other similar detector techniques. Electrode impedance measurements from multiple electrodes may be taken. An algorithm of the system processor may choose a correct initial dosage, and initial settings and/or range output.

Regarding setting up the correct initial dosage, the location and type of target tissue to be treated may also be generally diagnosed and characterized by ultrasonic, optical or other types of intraluminal sensing devices. Using the multi-electrode approach, electrical impedance measurements may be used to understand the electrical characteristics of target tissue of varying geometries and types previously diagnosed. Using that data, the initial therapy dosage setting can be optimized.

Regarding determination of proper dosage during therapy, the pattern of energy delivery can be a single pulse or multiple pulses of varying duration separated by resting periods of varying duration. The measurement of electrical impedance of the tissue, and of the electrode to tissue interface during energy delivery, and between energy pulses may be used to determine the optimum durations of energy delivery and resting periods. Pre-treatment bursts of radiofrequency energy can be applied to condition the target tissue. Conditioning may be utilized to activate HSP's in healthy tissue or non-target tissue prior to treatment to get better protection of such tissue. Post-treatment bursts of radiofrequency energy can be applied to control the cool down time of the tissue. Interim treatment bursts of radiofrequency energy can be applied to control the temperature of the target and surrounding tissue between multiple therapy bursts. Energy can be delivered in any combination of amplitude and frequency from any combination of electrodes. Some examples of energy bursts and pulse width modulations are shown in FIG. 21.

Impedance and/or impedance phase angle measurement on multiple electrodes may also be employed. When a multi-electrode design is used it is possible that some of the electrodes will be in contact with the lumen wall and others will be suspended in the blood or other existing fluid or thrombus, or existing stents, or foreign material of the like. The measurement of impedance at various radial locations allows the determination of which electrodes are in contact with the lumen wall and which ones are in contact with fluid such as blood. Phase angle may be indicative of increased capacitance and decreased conductance as electrodes come into sufficient contact with tissue, as blood may have less capacitance and greater conductance than tissue where a greater impedance phase angle may be an indicator of an increase of capacitance relative to conductance. By way of example, this information may be displayed to the user, such as on a screen of a power generator or user interface, to communicate whether sufficient contact is present to enable tissue treatment. This contact determination may be further used in combination with an intraluminal viewing device such as ultrasound to determine the physical orientation of electrodes.

Utilizing the impedance measurements between multiple electrodes, the determination of the contact status of each electrode with tissue or blood may be utilized to determine if the electrode carrying mechanism (catheter) is in the proper location for therapy. Impedance measurements between multiple electrodes may be used to determine contact quality of electrodes to tissue. Poor contact quality can cause excessive or unwanted localized heating or can otherwise prevent optimum treatment. Determination of contact quality may be utilized to minimize this type of problem.

In some situations the choice of electrode may be determined by a combination of position and quality of contact. Impedance measurements between multiple electrodes may be utilized to better understand which electrodes are in better contact or a better position to treat a specific area or lesion. The determination of energy level and frequency to be applied to the target may be based on quality of contact. Impedance measurements between multiple electrodes may be utilized to determine the optimum energy level and frequency. Energy may be applied to a single pair of electrodes, between multiple pairs of electrodes or from a single electrode to multiple electrodes or any combination thereof. Impedance measurements between multiple electrodes may be utilized to determine the optimum pattern.

Figure 23:
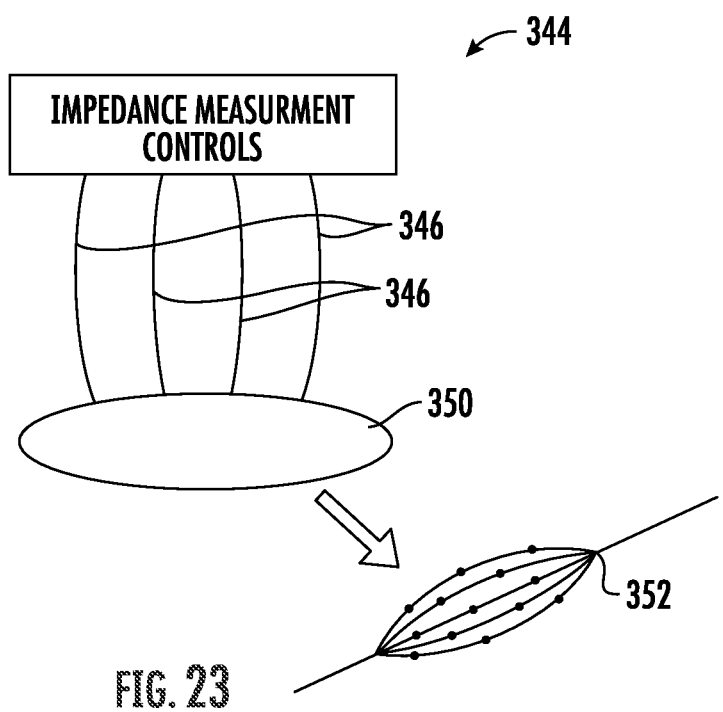
FIG. 23 illustrates four-electrode measurement system distributed across multiple electrodes to measure contact and tissue impedance.

Different embodiments may employ impedance measurement using two vs four electrodes, as can be understood with reference to FIG. 23. Four-electrode systems have been used for the measurement of electrical impedance in many applications. Four-electrode systems are inherently more accurate than two electrode systems due to inaccuracies created in the two-electrode systems by excessive contact impedance and electrical polarization reactions created in the contact area, however, electrode arrays of any suitable number may be used for a specific sensing and energy delivery application. In the four-electrode system 344, energy is delivered to the target by two energy delivery electrodes 346 and an impedance measurement is taken between the other two high impedance electrodes 348 shown schematically in contact with the tissue 350 in the energy path. In this multiple-electrode application any two electrodes can be utilized to deliver energy while any other two electrodes can be utilized for impedance measurement, thus forming a four-electrode measurement system. A probe or catheter 35 may include a circumferential and/or longitudinally distributed array of electrodes may be used to contact the tissue, and any four electrodes of the catheter can be configured for energy delivery or impedance measurement. Thus, the electrode array can be utilized as a two or four electrode system.

In many applications it is helpful to know how much energy is being delivered to the target tissue and how much is being dissipated in the interface between the electrodes and tissue. By taking measurements as a two-electrode system and then as a four-electrode system the electrode to tissue interface may be characterized and that data may be utilized to determine how much energy is being dissipated in the electrode to tissue interface and how much is actually delivered to the target tissue. Measurement of the electrical impedance in a plurality of electrode configurations, including the two or four electrode configurations, may be performed statically utilizing small excitation signals or can be measured dynamically during the application of energy at the normal therapy levels. Using this technique, tissue electrical impedance may be measured dynamically during the application of energy to determine the state of the melted tissue and surrounding tissue. For controlling the energy delivery dosage, the electrical impedance characteristics of tissues vary due to temperature variations and the molecular state of a tissue. Dynamic measurement of electrical impedance of the tissue during application of energy can be used to monitor the changes in the tissue and the progress of the therapy. A four-electrode implementation of the electrode system would allow for measurement of the electrical impedance of the electrode to tissue interface and therefore, measurement of the change in temperature of the tissue at the contact surface and that of the contact tissue.

Impedance measurement may optionally be performed in monopolar configuration. It is possible to utilize multiple electrode systems in a monopolar configuration where the return electrode is an electrically conducive pad applied to the external surface of the patient or the like. In this configuration impedance measurements can be performed between any one of the internally applied electrodes and the external return pad in the two-electrode mode or any one of the internally applied electrodes can apply energy that flows to the external return pad while any other two internally applied electrodes is used to measure impedance.

Regarding temperature measurements, impedance measurements taken prior to therapy may optionally be utilized to calculate a normalized value to be used in further calculations to determine the change in temperature from that initial value. Dynamic monitoring of the electrical impedance of target and surrounding tissue during therapy may be utilized to calculate the change in temperature of tissue. In some embodiments, dynamic monitoring or the electrical impedance of the interface between electrodes and tissue may be utilized, for example, to prevent tissue charring or coagulation of blood at the interface.

Temperature change during therapy may be utilized to determine the effectiveness of energy delivery settings and to determine the condition of the tissue being treated. In addition to direct temperature measurement by using sensors, measurement may be performed by intraluminal ultrasound or other mechanism and verified by data derived from impedance measurements.

Figure 24:
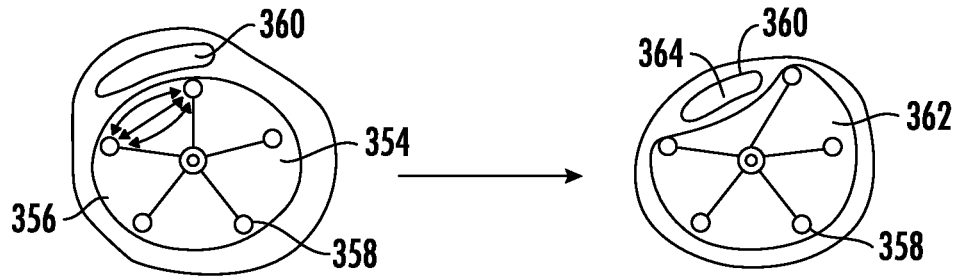
FIG. 24 illustrates flooding of vessel with non-ionic fluid to direct energy to vessel wall and surrounding tissue, reducing losses in native fluid.

Use of the systems described herein with ionic and non-ionic fluid can be understood with reference to FIG. 24. When electrical current flows in an ionic fluid such as blood filling a lumen 356, at least a portion of the current may pass through the blood when electrodes 358 are energized. Even with electrodes on either side of a target tissue 360, heating of the target tissue may be reduced by the current flow within the blood. When used in a fluid-filled lumen such as an artery, the catheter device can be used in combination with a non-ionic fluid flooding the area 362 to displace or partially displace the native fluid to modify the conductivity of the environment around the electrodes. This action can be desirable in order to direct the energy, in the form of electrical current 364, into lumen walls instead of through the native fluid, there by delivering energy to the tissue of the surrounding walls with minimal dissipation into the fluid filling the lumen. A second purpose of the non-ionic fluid or an ionic fluid may be to provide cooling to the electrodes and to the tissue on the surface and just below the surface of the lumen wall.

Electrical impedance measurements at the electrodes may be utilized to determine the conductivity of the surrounding fluid, thus measuring the concentration of non-ionic fluid in the native fluid. This data may be fed to the control system to allow for adjustment of ionic fluid concentration to optimize delivery of energy to the target tissue and minimize undesired effects to surrounding tissue. Use of blood as contact interface is also an option. Blood is a conductive ionic fluid that may be used as an interface between electrodes and tissue to ensure a good electrode-tissue contact and low contact impedance.

Figure 27:
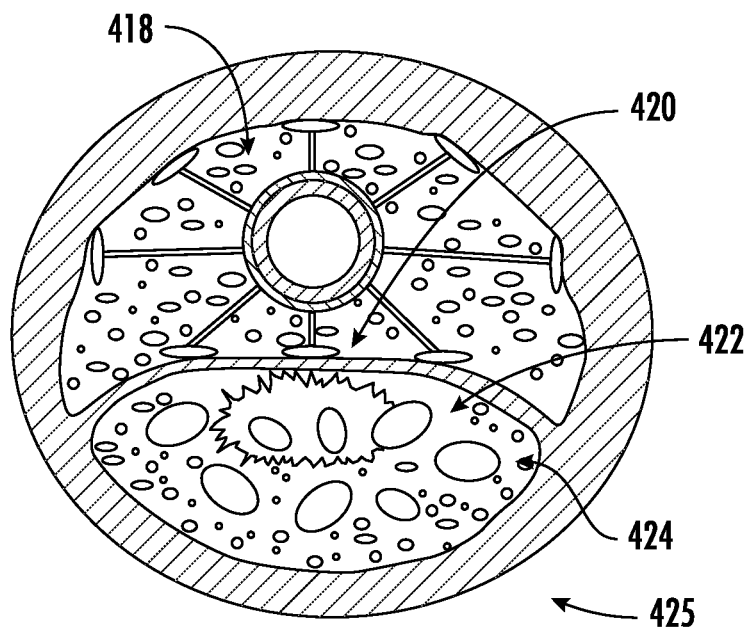
FIG. 27 illustrates selective treatment of plaque.
Figure 27A:
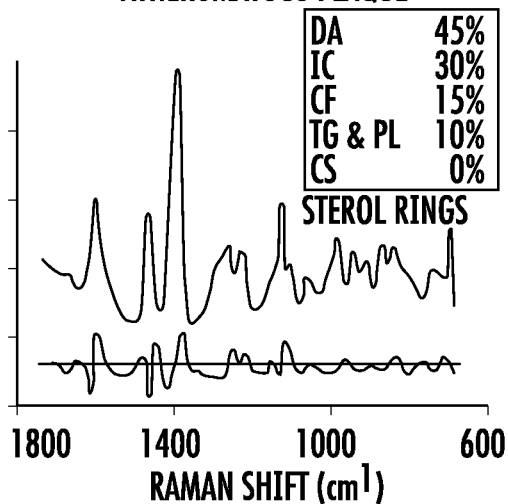
FIGS. 27A-C illustrate spectral correlations of tissues, as may be used to analyze or characterize plaques.
Figure 27B:
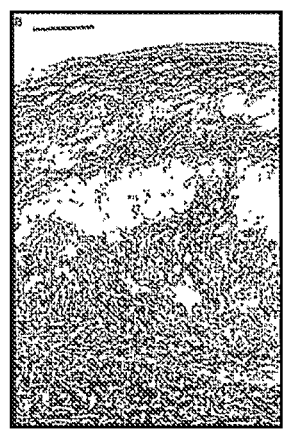
Figure 27C:

Referring now to FIG. 27, the catheter devices 418, systems and methods described herein will often be used to treat plaques having fibrous tissue 420. Fibrous tissue 420 may be heated to a target tissue to a temperature in a range from about 90 to about 95° C., which may provide shrinkage of up to about 50%. Lipids 424 may be heated to target temperatures in a range from about 80-85° C., providing up to about 90% shrinkage. Damage to adventitial layer 426 may be inhibited or the layer protected by limiting heating to below about 62° C. These and other temperatures and shrinkage estimates are further determined by empirical testing or the like, from unpublished and/or published work, or form other sources such as numerical methods. Referring to FIGS. 27A-27C, spectral correlations to diseased tissue may allow tissue characterization using techniques such as those described in an article by Tjeerd J. Romer et al. entitled "Histopathology of Human Coronary Atherosclerosis by Quantifying Its Chemical Composition with Raman Spectroscopy," Circulation 97:878-885 (1998), the entire contents of which are incorporated herein by reference.

Figure 28A:
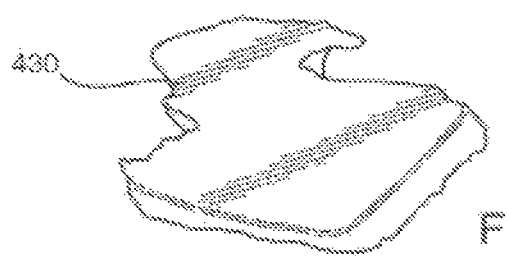
FIGS. 28A-D illustrate bench top remodeling of tissue using an animal fat model treated with an exemplary embodiment of the catheter system.
Figure 28B:
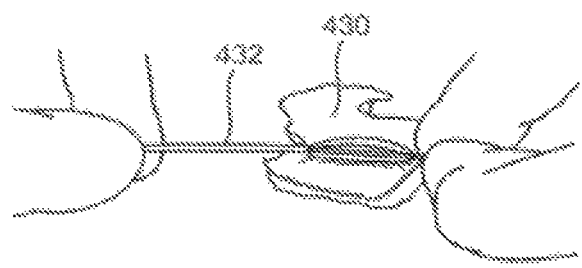
Figure 28C:
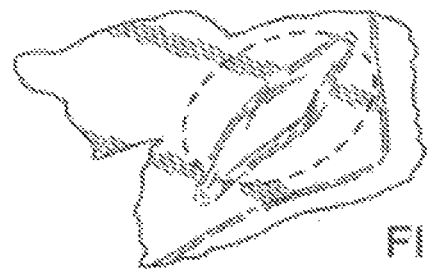
Figure 28D:
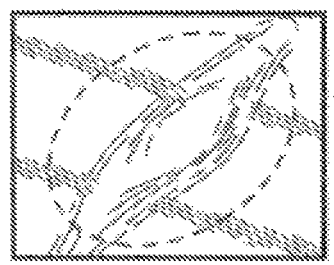
Figure 29A:
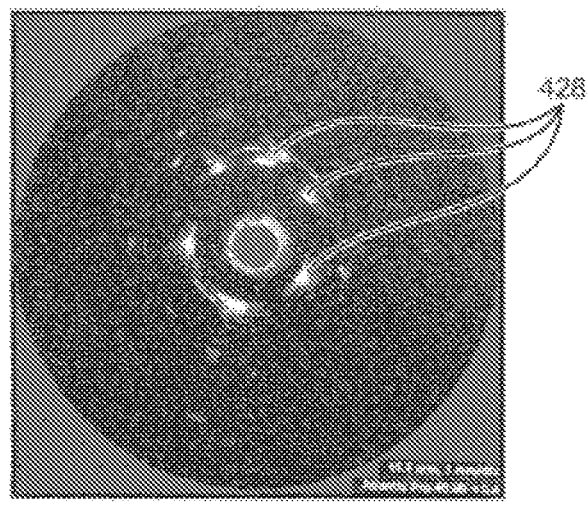
FIGS. 29A and 29B illustrate intravascular imaging and eccentric remodeling with an exemplary embodiment of the catheter system.
Figure 29B:
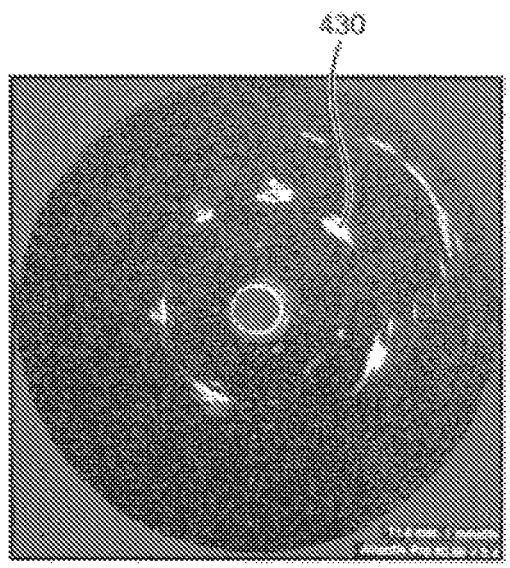

Referring now to FIGS. 28A-28D, feasibility of tissue shrinkage may be seen in a bench top experiment using a catheter system such as those described herein. An animal fat tissue model 430 (shown before the treatment in FIG. 28A) can be treated by manually holding the expandable structure and associated electrodes of the catheter in contact with a surface of the tissue during treatment with tissue remodeling electrosurgical energy (see FIG. 28B). After treatment, as seen in FIG. 28C and the close up of FIG. 28D, visible shrinkage of the tissue can be verified. Feasibility of the use of intravascular imaging with the methods and systems described herein can be verified by images of the six individual electrode-supporting struts 428 of the expandable structure of the catheter in FIG. 29A, as well as by viewing an eccentric void 430 of the expandable structure of the catheter in FIG. 29A, as well as by viewing an eccentric void 430 that is created using a benign guided reshaping energy delivery targeted so as to increase effective artery diameter for better blood flow, as seen in FIG. 29B.

Figure 30:
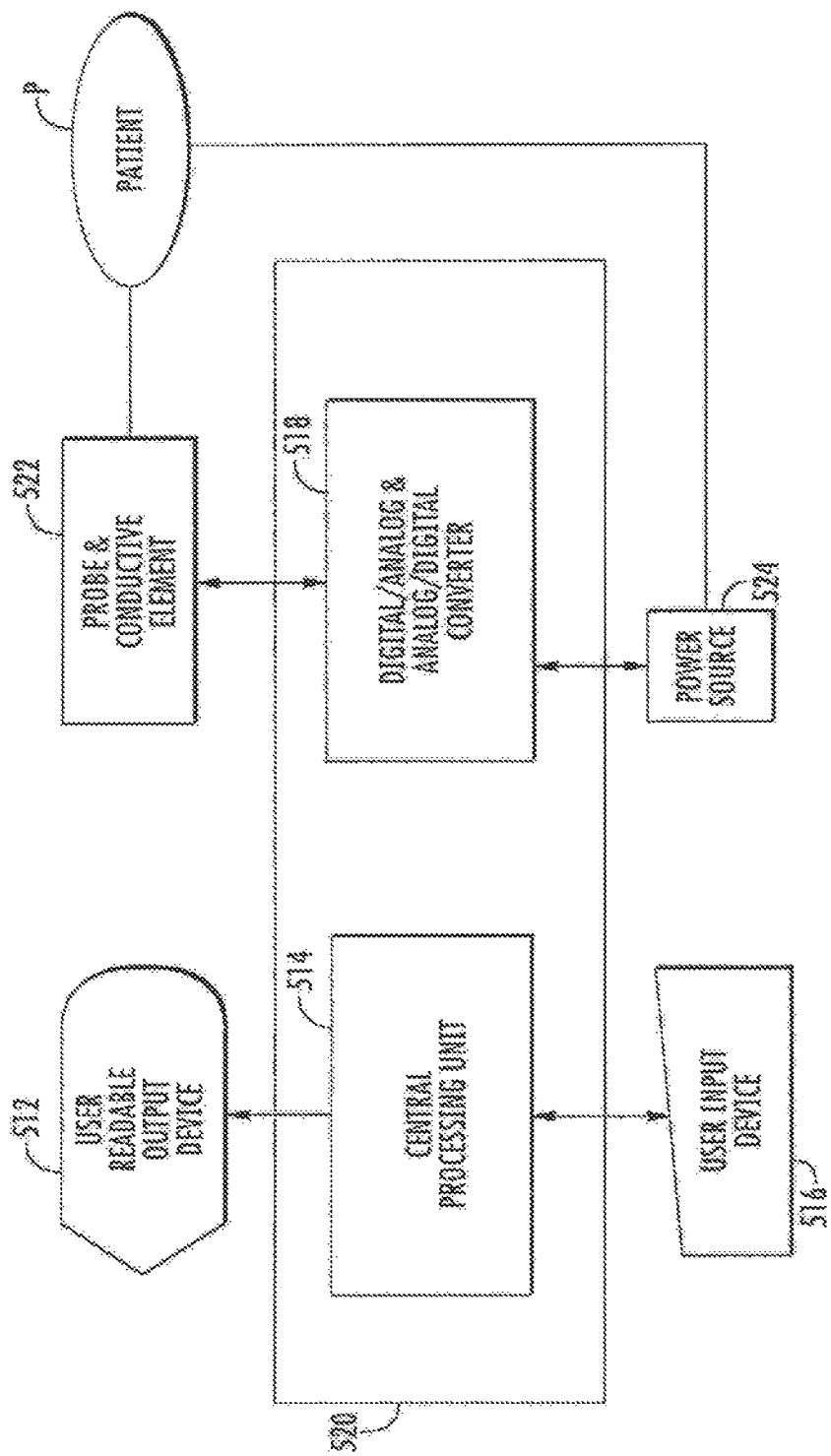
FIG. 30 is a simplified schematic illustrating components of the system of FIG. 2 that cam be used for intraluminal tissue and other material analysis and characterization.
Figure 31A:
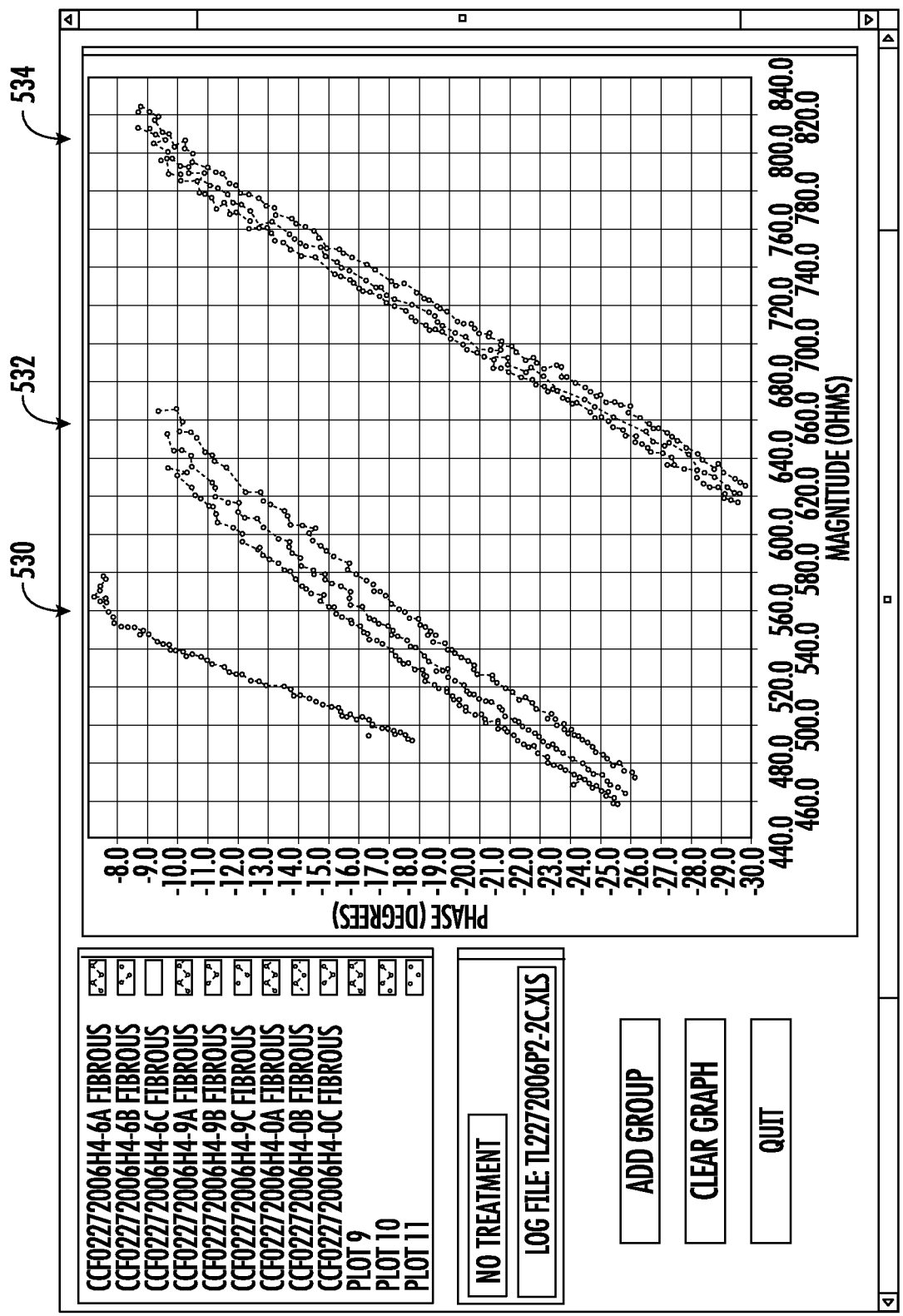
FIGS. 31A-J graphically illustrate relationships between phase angles and impedance in a frequency range as can be used to electrically analyze and characterize materials engaging and disposed between electrodes of the system of FIG. 2.

Referring now to FIGS. 30 and 31A, advantageous embodiments may employ aspects of electrical tissue discrimination techniques and devices described in U.S. Pat. No. 6,760,616 to Hoey et al., entitled "Tissue Discrimination and Applications in Medical Procedures," the full disclosure of which is incorporated herein by reference. As more fully described in that reference, tissue identification system 510 includes a user readable output device 512, a user input device 516, a processor 520, and a probe 522. The processor 520 includes a central processing unit ("CPU") 514, a Digital to Analog converter ("D/A"), and an Analog to Digital converter ("A/D") 518. Processor 520 may be included in processor 49 (see FIGS. 2 and 3), and probe 522 may comprise any of the catheter structures described herein, so that tissue identification system 510 may be, embodied in system 10.

Tissue identification system 510 may apply a sliding or variable frequency electrical signal by energizing the electrode with a variable frequency power source 524. Power source 524, the electrode of probe 522, and the engaged tissue of patient P can thus generally be included in a circuit, and an electrical characteristic of the circuit can be measured at different frequencies. In exemplary embodiments, an impedance (both phase angle and magnitude) of the circuit is measured at a plurality of frequencies within a frequency range of about 4 KHz to about 2 MHz. Each frequency/magnitude/phase angle datapoint may represent a tissue signature measurement, with a series of individual datapoints often being taken under similar conditions (for example, at a given frequency and without moving the electrodes) and averaged for enhanced accuracy. The tissue signature datapoints may be measure at a plurality of frequencies throughout a range of frequencies so as to generate frequency/phase angle/phase magnitude curves representing a tissue signature profile or correlation 530, 532, or 534, which may be used to characterize the tissue of the circuit.

The signals used to derive the tissue signature profiles 530, 532, 543 will often be driven between electrodes of the catheters described herein. Conveniently, the tissue included in the circuit may be controlled by selecting different electrode pairs for testing, with or without repositioning of the electrodes. There may be significant patient-to-patient differences (or even region to region differences within a patient) for individual tissue signature measurements, and these differences may, at least in part, be caused by the different configurations of the electrodes during testing, different distances between electrodes, and the like. Nonetheless, the relationships (and particularly the relative slopes of the profile correlations, the offsets between correlations, and the like will be sufficiently consistent to allow tissue characterization, particularly where a baseline tissue signature profile for the patient or tissue region is obtained using IVUS, OCT, or the like. Where a region of (for example) healthy tissue can be identified using IVUS and used to generate a baseline tissue signature profile for the patient, other nearby tissue signature measurements or profiles can then be normalized to that baseline, compared to the baseline, etc. From the offsets, the differences in slope, and the like, the tissue can be analyzed.

Referring now to FIGS. 31A-31J, the relationships between tissue signature profile curves or correlations can be used to analyze and characterize the tissues engaged by the electrodes of the probe. For example, a correlation 530 associated with fibrous plaque (seen on the left side of the graph of FIG. 31A) has both a slope and a magnitude that differs significantly from that of a calcified plaque 534 (seen in the right side of the plotted data) and from a correlation 532 associated with thrombus (generally between 530 and 534). The offsets between the correlations here encompasses a difference in phase for a given impedance, a difference in impedance for a given phase, or the like. As can be understood with reference to the graphical plots, the relationships between correlations may be determined by fitting curves to the data, by statistical analysis, by lookup tables, or the like. In exemplary embodiments, tissue signature measurements may be taken by (for example) a commercially available vector impedance meter such as a Hewlett-Packard Model No. 4193A, and the correlations may be captured using LabView™ Software and plotted or manipulated using Excel™ spreadsheet software from Microsoft, or the like. Once sufficient benchmarked data has been obtained and repeatability under different probe configurations has been established, electrical circuit measurements tissue characterization without benchmarking of each patient may avoid the expense of IVUS measurements.

Figure 31B:
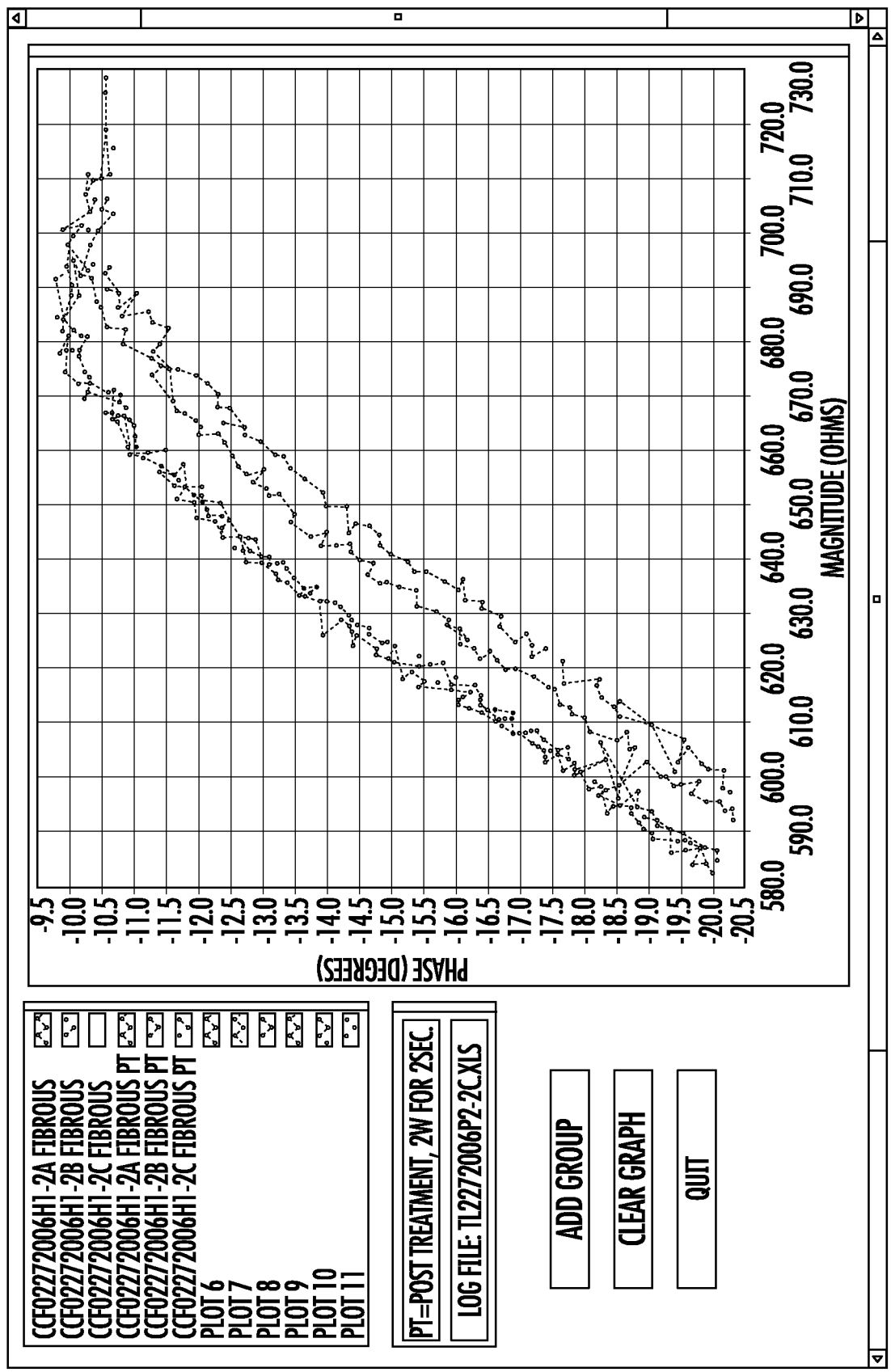

As shown in FIG. 31B, along with characterizing different tissues, the relationships can also be used as feedback on treatments of tissues proximate to luminal walls. For example, a fibrous plaque correlation or profile before treatment (toward the right side of the plot) changes in magnitude during treatment to a post-treatment correlation or profile (toward the left side). The treatment here comprises 2 W of electrosurgical energy for 2 seconds, showing that moderate remodeling or partial treatments can be monitored, verified, and/or controlled using the electrical characteristics of the circuit of tissue identification system 510.

Figure 31C:
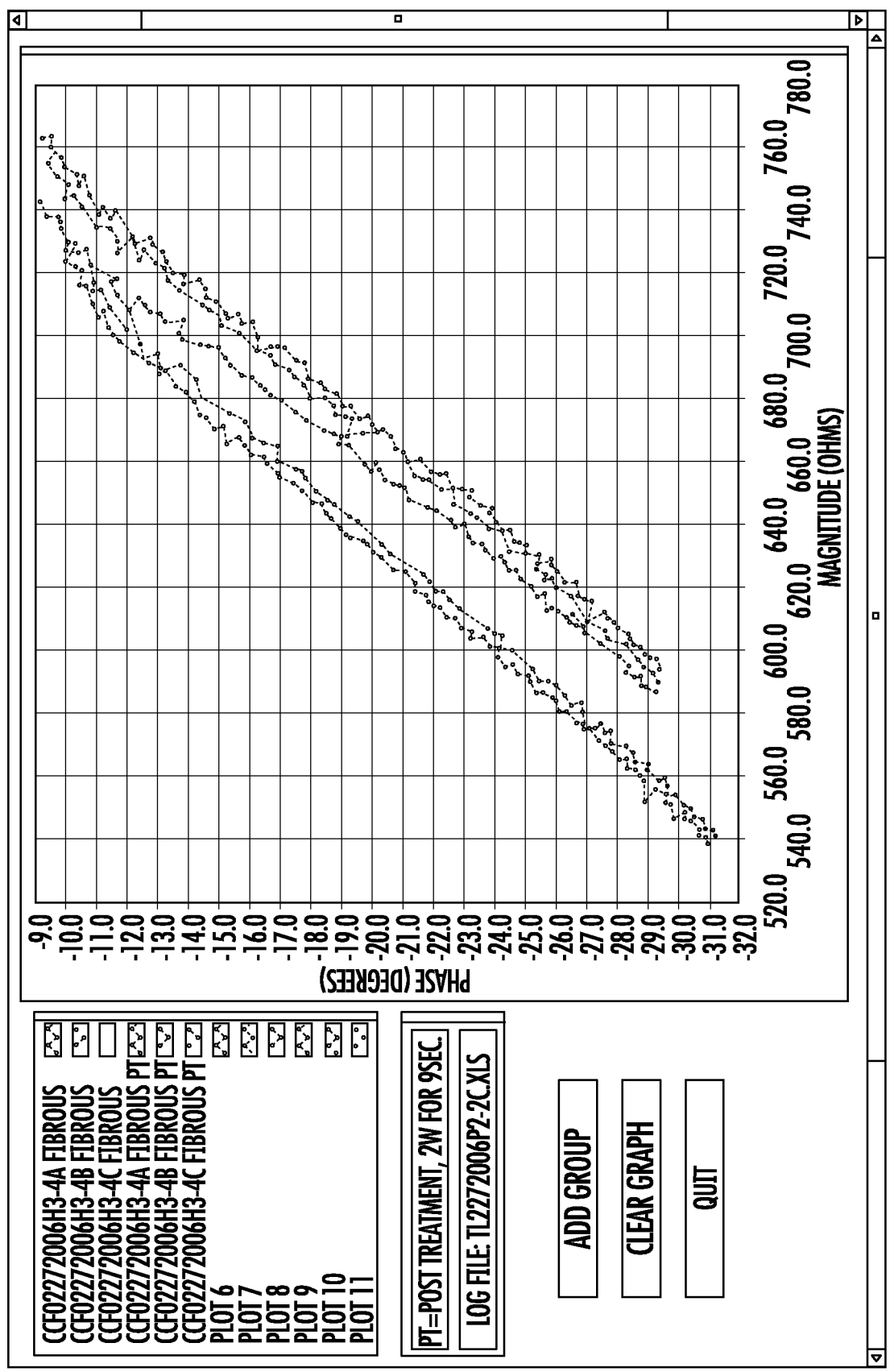
Figure 31D:
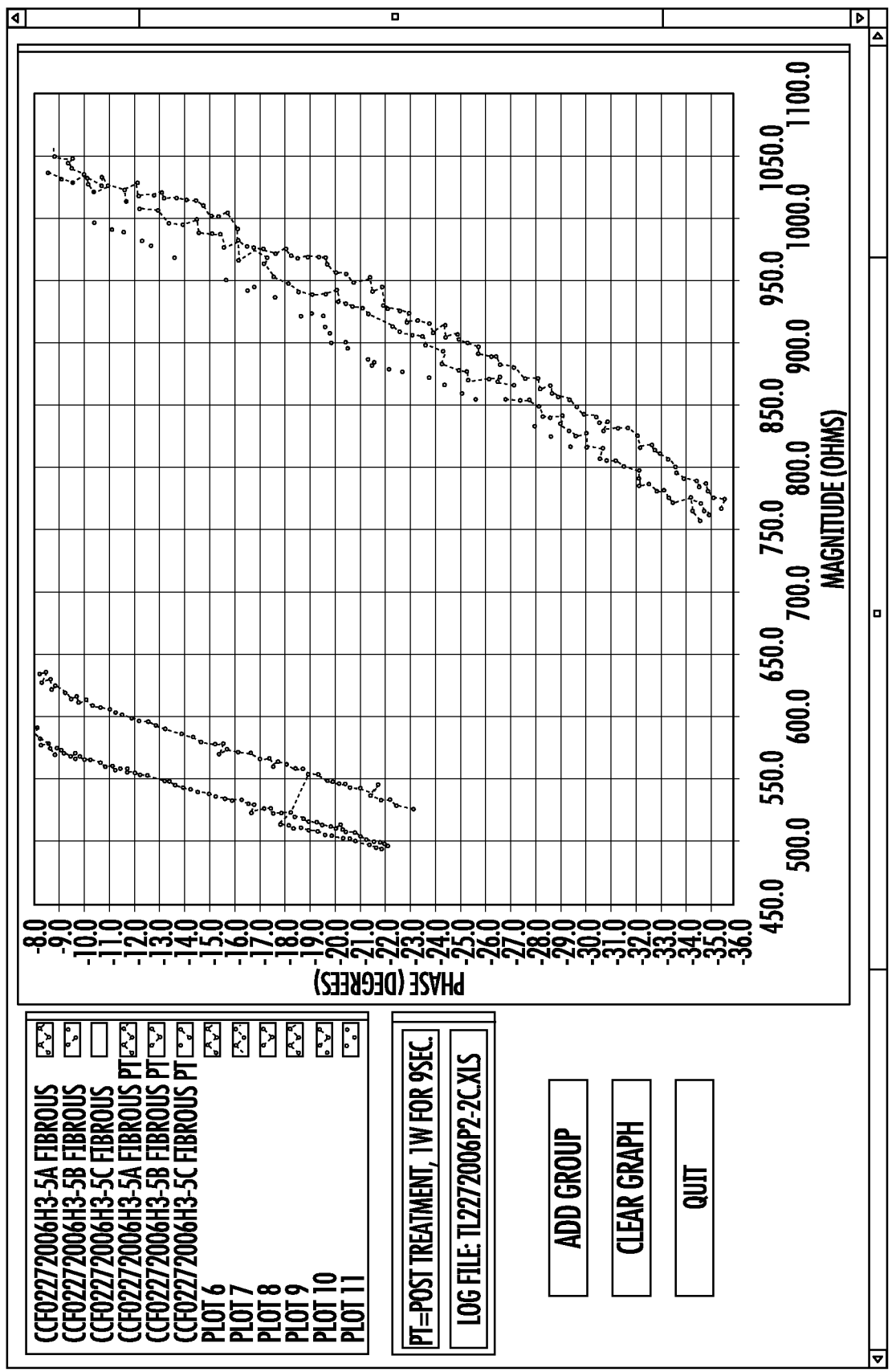

Advantageously, once an appropriate frequency or range of frequencies has been determined, the entire tissue signature profile need not be generated for analysis of ongoing tissue treatments and/or characterization of tissues, as offsets may be readily identified. Such measurements may, for example, allow tissue temperatures to be determined, particularly where the temperature is a treatment temperature that alters an offset of the tissue signatures. The energy of the electrical signals used for tissue analysis may typically be less than the remodeling treatments. A similar plot is shown in FIGS. 31C and 31D, with the post treatment correlation here being after treatment with 2 W for 9 seconds and 1 W for 9 seconds, respectively.

Figure 31E:
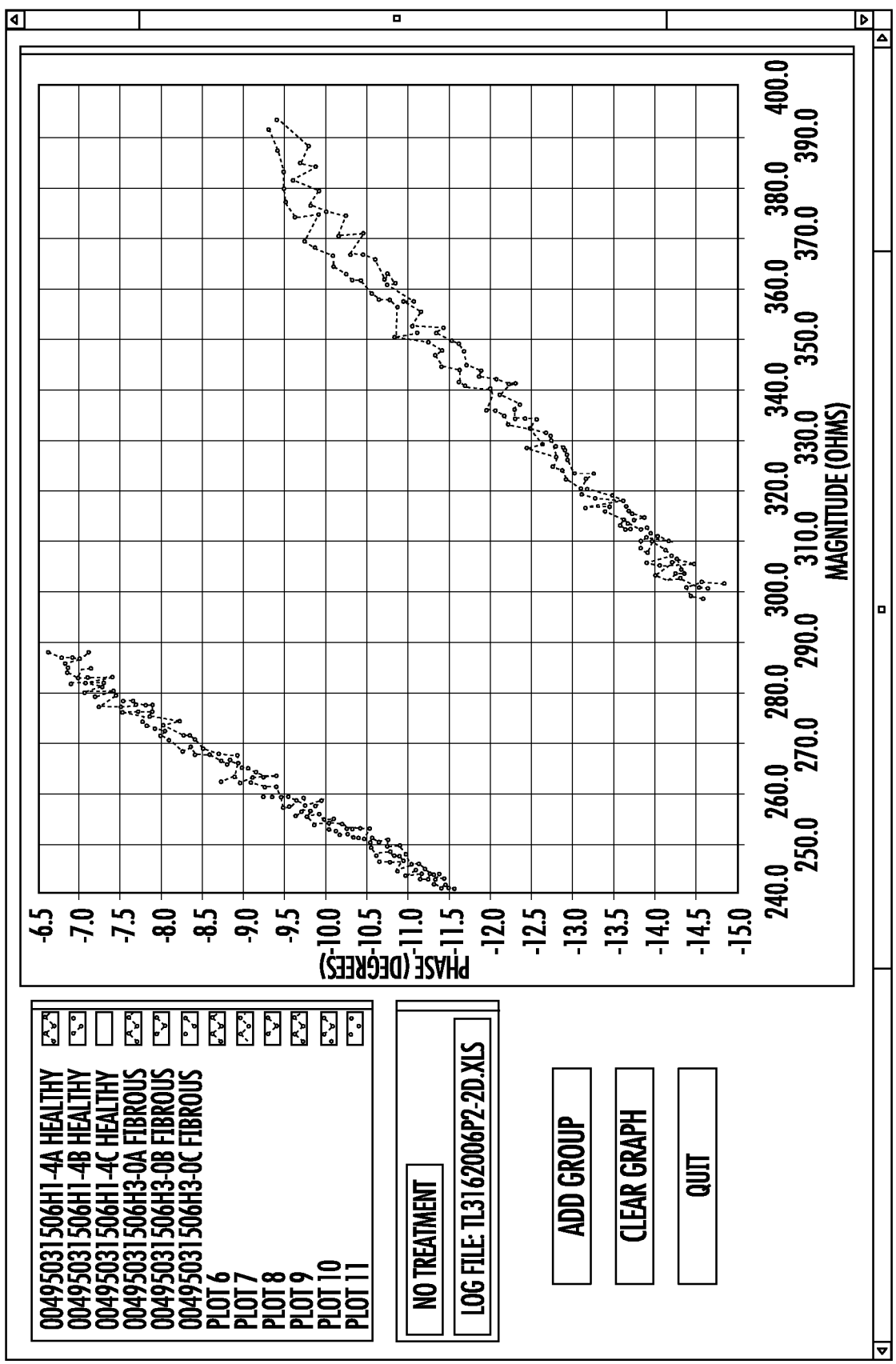
Figure 31F:
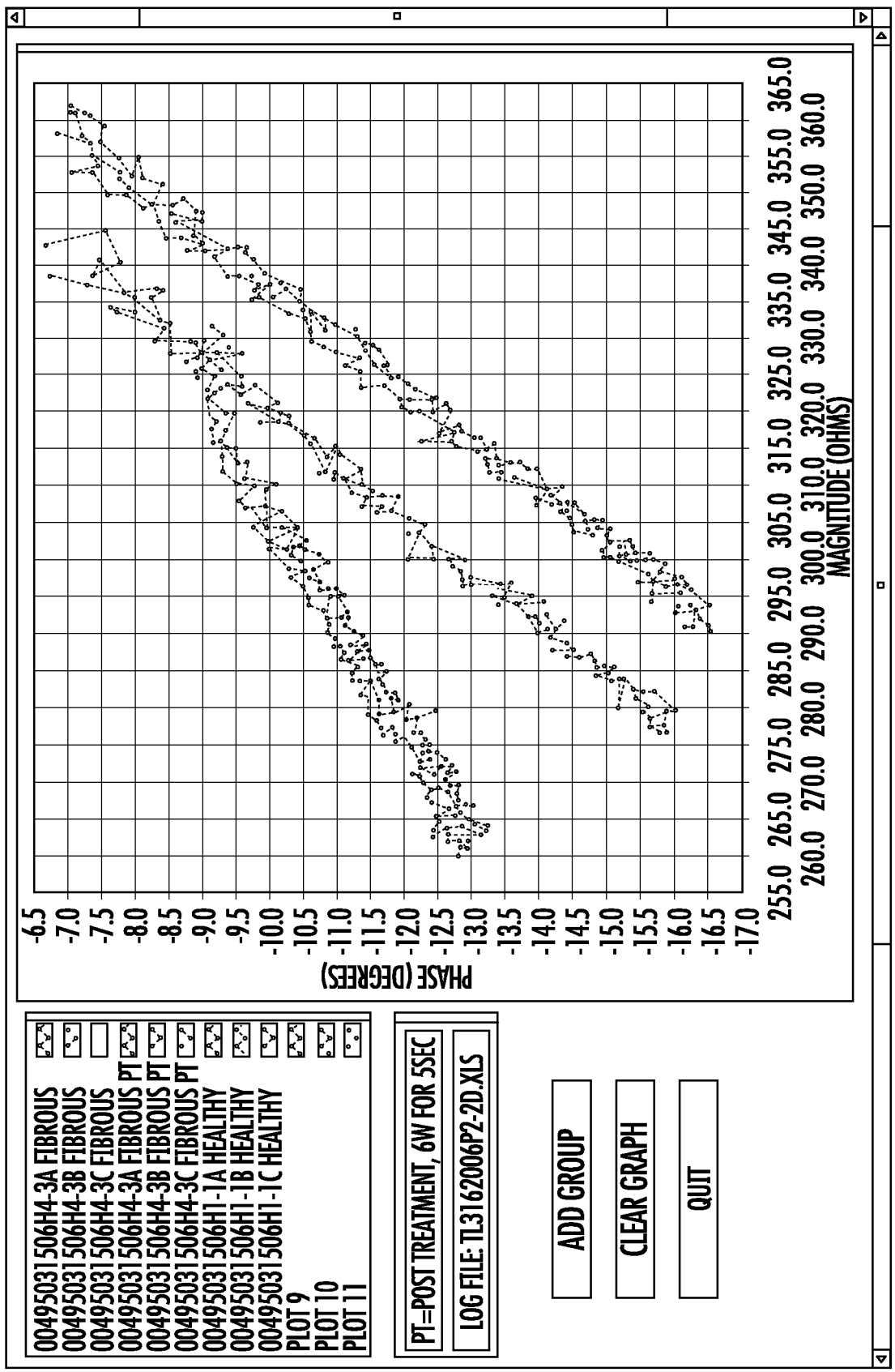
Figure 31G:
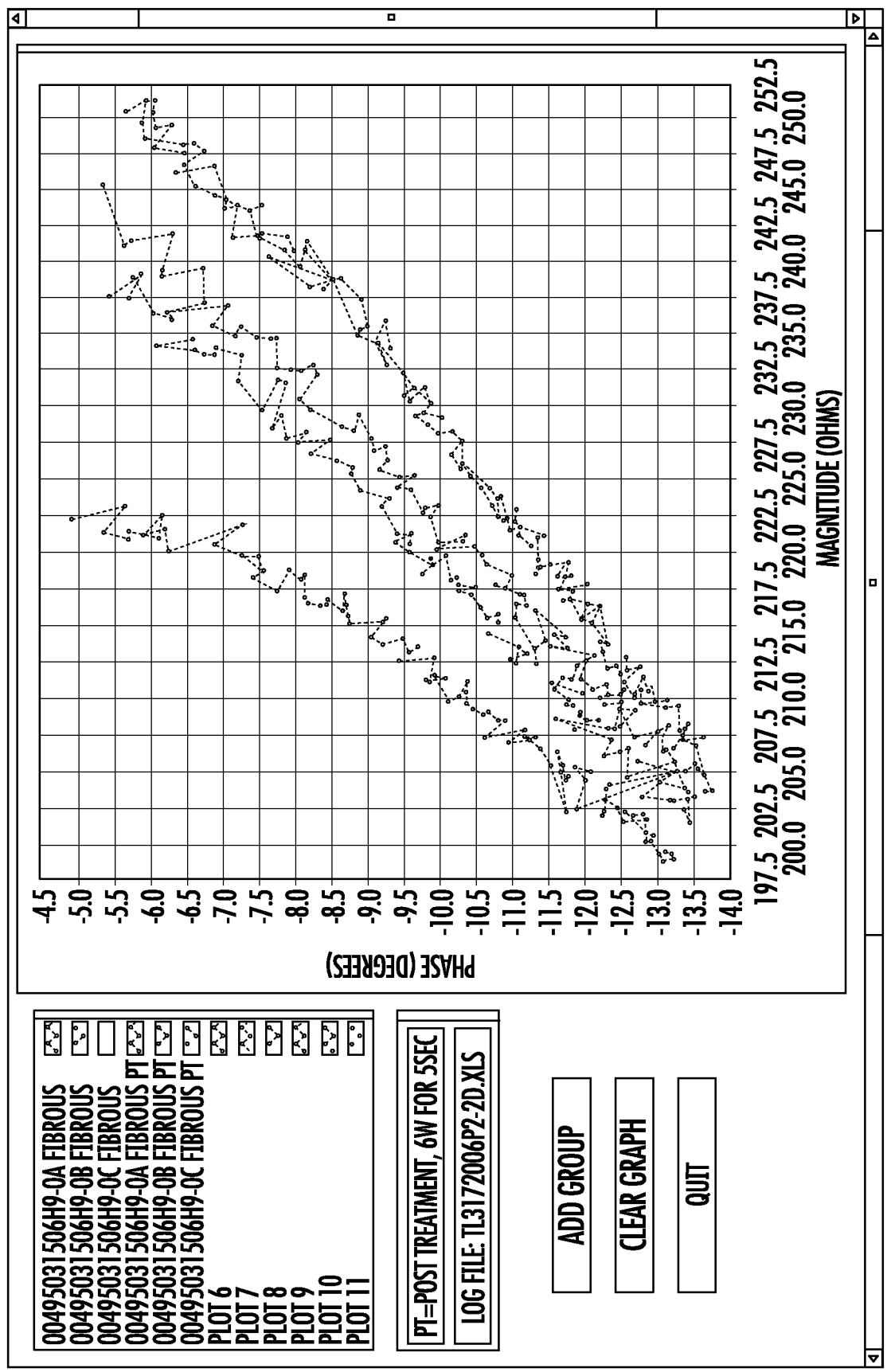
Figure 31I:
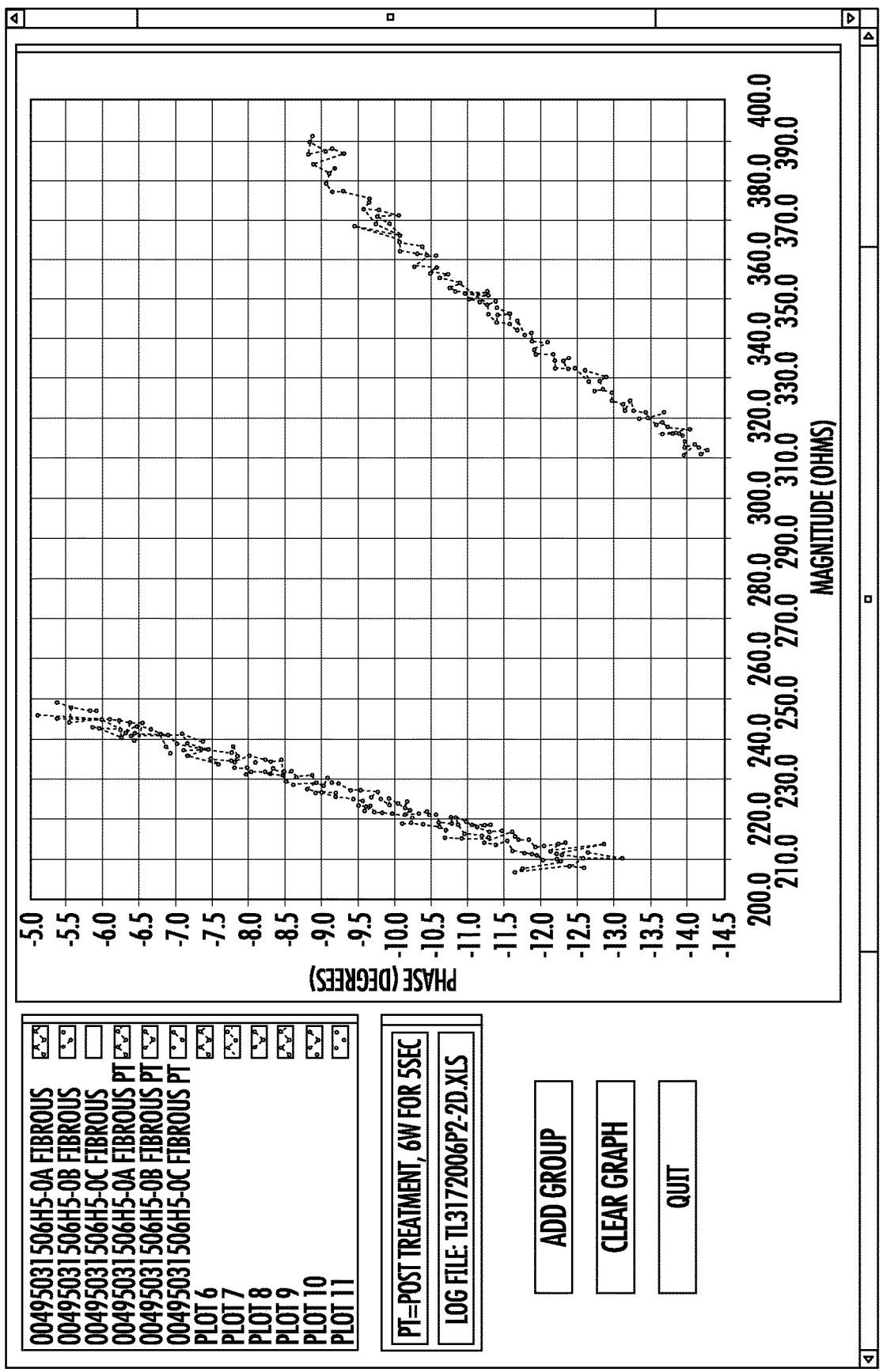
Figure 31U:
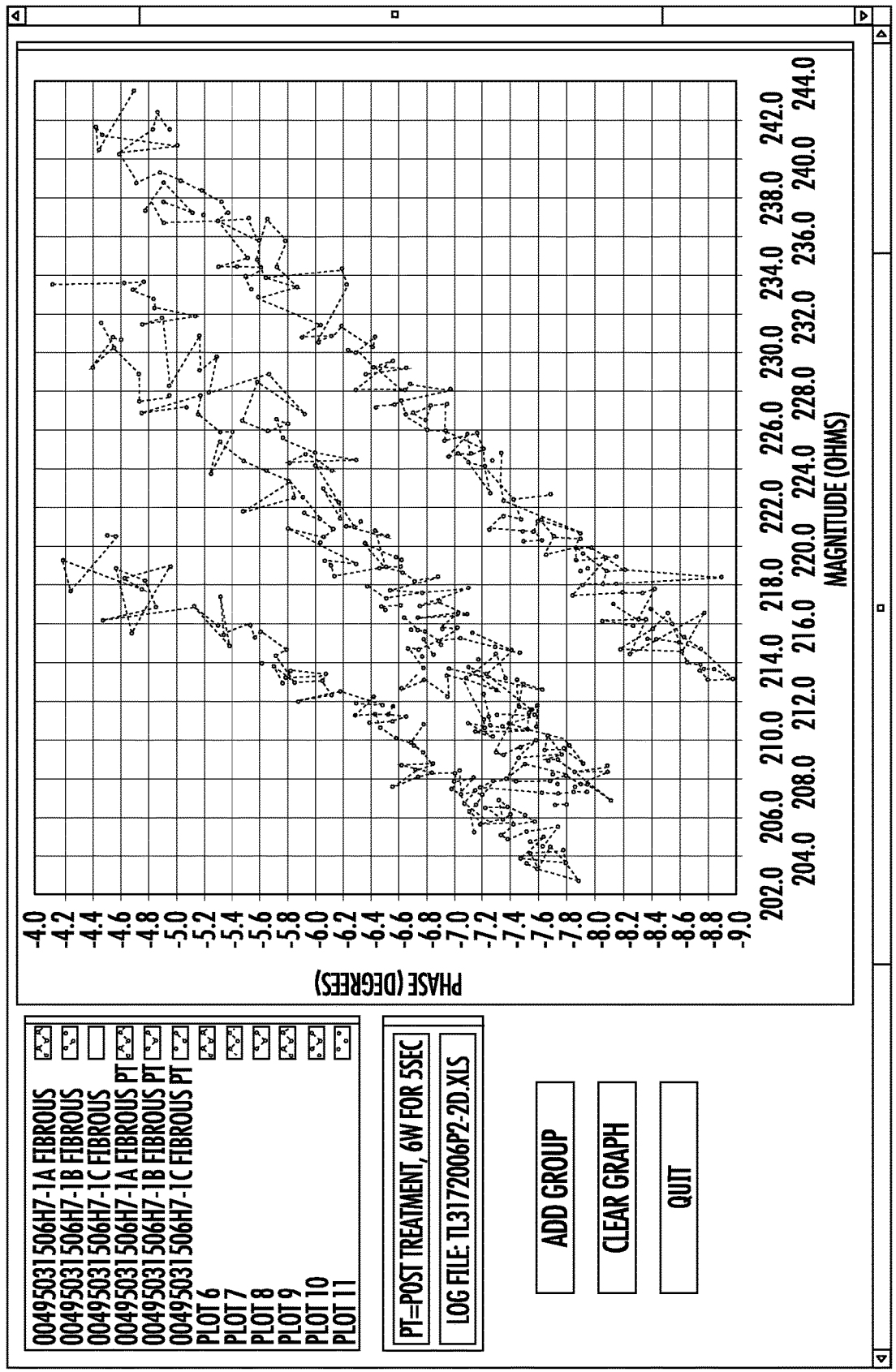

Referring now to FIG. 31E, relationships between healthy tissue (toward the right) and fibrous plaques (toward the left) can be identified from their associated tissue signature profiles or correlations, which differ significantly in both slope and magnitude. FIG. 31F shows relationships between correlations or profiles for fibrous tissue before treatment (left), fibrous tissue after treatment (right), and healthy tissue (center). FIGS. 31G-31J illustrate additional plots of relationships between profiles or correlations associated with fibrous tissues and treated fibrous tissues.

Figure 32:
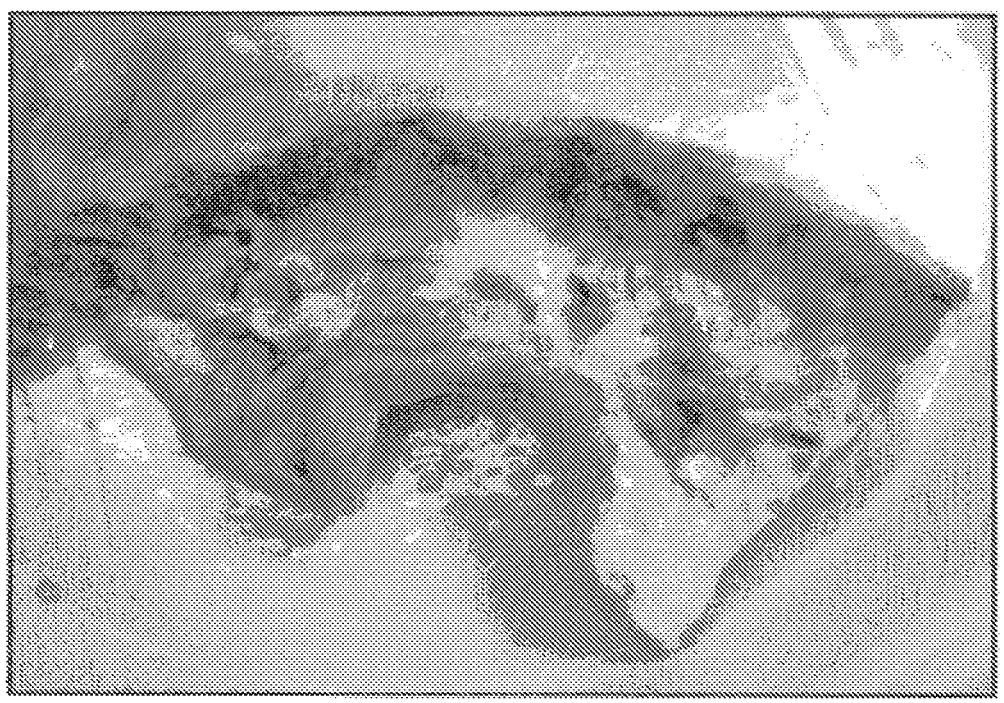
FIG. 32 illustrates a variety of tissues for characterization and selective treatment by the system of FIG. 2.

Referring to FIG. 32 a severely diseased blood vessel with three basic categories of plaque can be seen: lipid right (fatty) plaque, fibrous plaque, and calcified plaque or tissue. All may be present in one sample, and may also be present in the diseased tissue of (or adjacent to) one lesion, making the lesion hard to treat using conventional techniques. Through the tissue analysis techniques described herein, the correct prescription and dosage of energy may be targeted and delivered to effect a safe and appropriate (and often different) remodeling of the different tissue categories or types, at the appropriate locations of the constituent parts that make up each lesion.

Figure 32A:
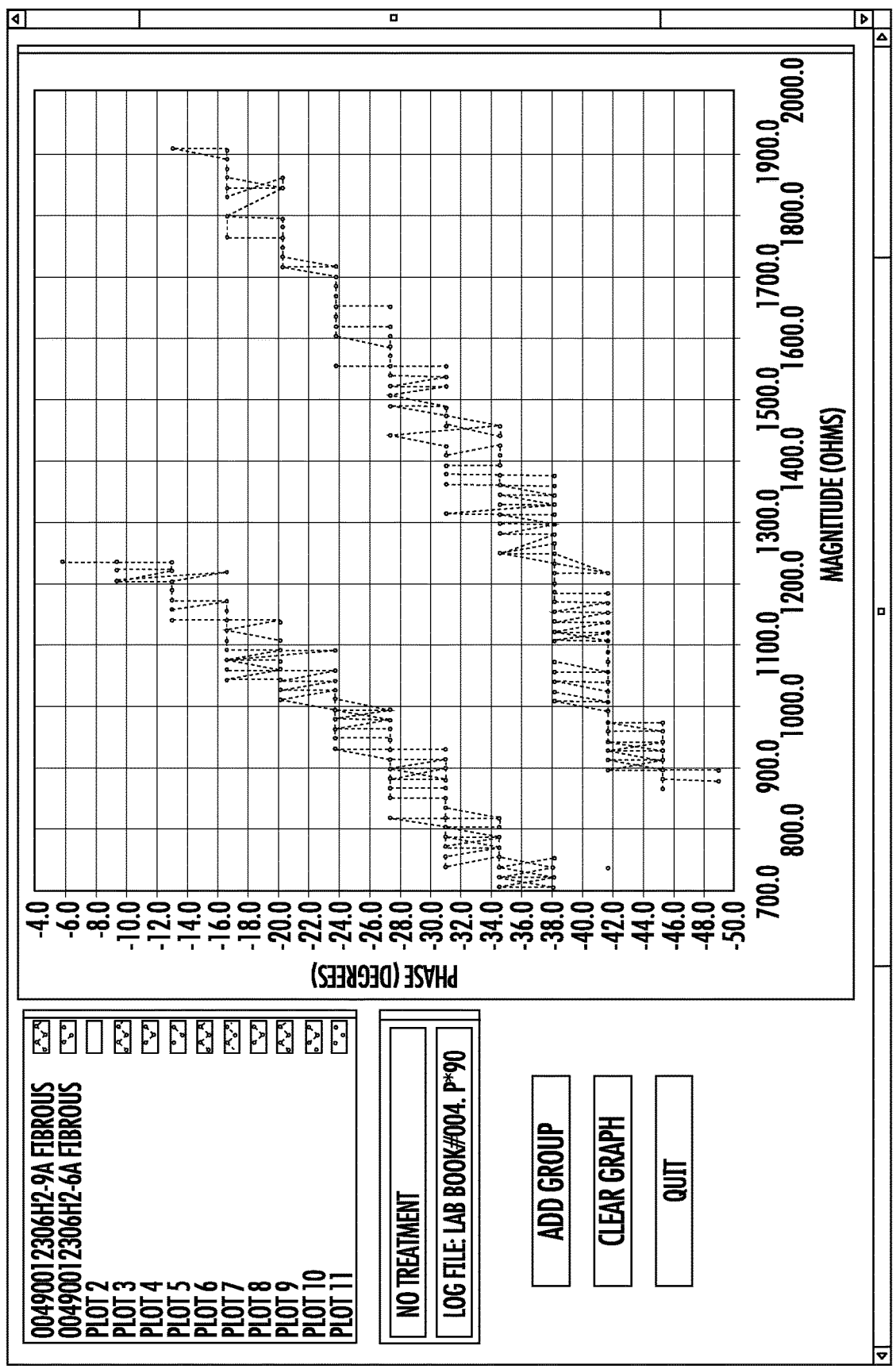
FIGS. 32A-C illustrate changes in a relationship between phase angle and impedance in a frequency range associated with treatment of a tissue, along with histological images of the tissue before and after treatment.
Figure 32B:
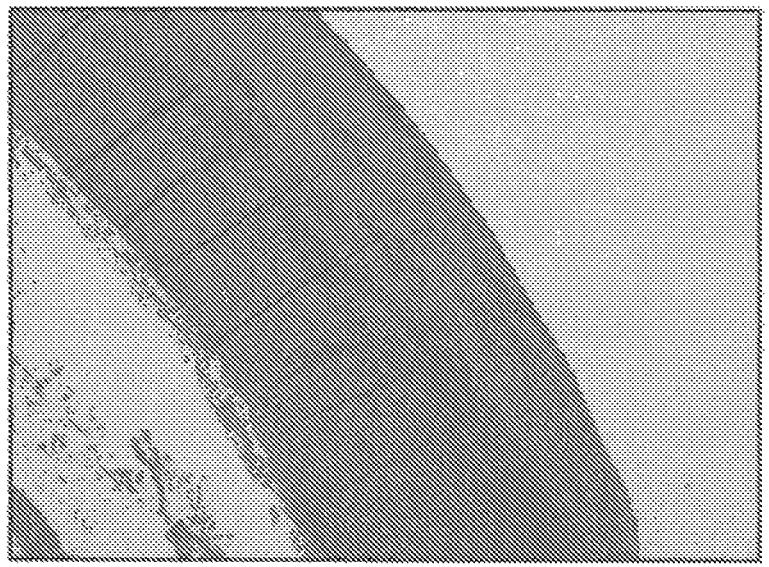
Figure 32C:
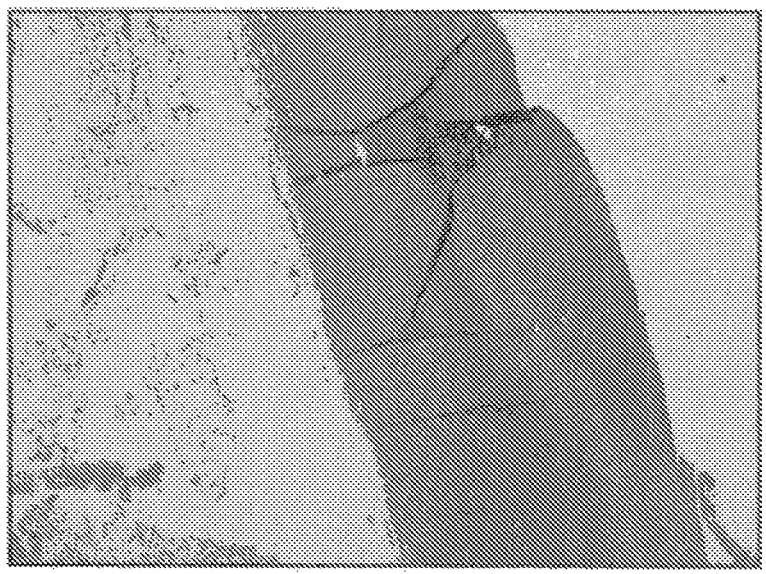

Referring now to FIG. 32A, this graph shows tissue signature measurements and tissue signature profile results obtained from a human aorta specimen, with these results for an engaged fibrous plaque before and after treatment, FIGS. 32B and 32C show histopathology slides of the tissue. The cracks visible on each slide may be artifacts of the mounting process. The nucleation or voids that show up in FIG. 32C, however, may indicate a remodeling of the tissue itself.

EXPERIMENTAL

Testing of the delivery of energy to tissue proximate to a lumen has included the treatment of in-stent restenosis, trials have yielded preclinical and in-human data.

1. Preclinical

An experiment was conducted to establish a comparison of temperature measurement during different energy doses at four depth levels, upon low pressure (less than 6 atmospheres) balloon inflation: 1) 0 mm, at the surface of the balloon, representing the endothelial layer of the vessel wall; 2) 1 mm, representing the b order between the neointima and the media, at the stent location; 3) 2 mm, representing 0.5 mm into the adventitia; and 4) 3 mm, representing 1.5 mm into the adventitia. Comparisons of temperature were made between two population groups; one group in tissue with an implanted stent, and the second group without an implanted stent. The objective of the study is to determine the energy dosing that would provide a temperature of about 55° C. or greater while having minimal temperature elevation beyond the stent (1 mm and deeper).

Measuring temperature at the surface of three pairs of electrodes (7-8, 8-9, and 9-10), and 1, 2 and 3 mm deep, bipolar radiofrequency energy delivery was conducted in two rounds: for the first round only half of the electrodes are activated (electrodes 1-2, 3-4, 5-6, 7-8, 9-10 each pair energized in sequence), and for the second round, the other half of electrodes are activated (electrodes 2-3, 4-5, 6-7, 8-9, 10-1, again, pair energized in sequence). The test medium is heated to a baseline temperature of 37° C. representing nominal human body temperature. Temperature was captured from each of six thermocouples, starting 1-2 seconds before the electrodes were activated, and lasting for about 10 seconds following the activation of the last electrode (10-1). In all treatments, all the electrodes were activated, meaning that both first and second rounds were activated, leading to a "full circumferential" (FC) treatment.

Referring to FIGS. 43A-48, the individual lines demonstrate temperature measurement at the surface of three pairs of electrodes 705 (7-8; blue line), 706 (8-9; red line), 707 (9-10; green line), and measurement at three depths 708 (1 mm deep; purple line), 709 (2 mm deep; light blue line), and 710 (3 mm deep; orange line). As may be seen in FIGS. 43A-44B, the temperature measurements for energy doses, with stent vs. without a stent, are comparable. The peak temperature for each round is slightly higher with stent, vs. without a stent. In addition, the temperature measured in 1 mm deep, is slightly higher with a stent vs. without a stent. Proposed energy doses for in-stent tissue are shown in FIGS. 45A-48; among the energy doses tested, the dose of 4 watts for 2 seconds for the first round, followed by 4 watts for 1 second for the second round ("4×2×1") shown by FIG. 48, demonstrated the highest preferred peak surface temperature (~60° C.) while maintaining a preferred temperature at 1 mm depth. A peak temperature of about 55° to about 65° C. may enable collagen denaturation of the neointima tissue, dehydration and volume reduction, and, cell death is expected to be limited to the neointima tissue. Prevention of heat penetration into the adventitia may better avoid injury, inflammation, fibrosis and restenosis, while neointima volume reduction during balloon inflation, may prevent flow-limiting dissections inside the stent, which, can lead to better acute and low term results.

Figure 52A:
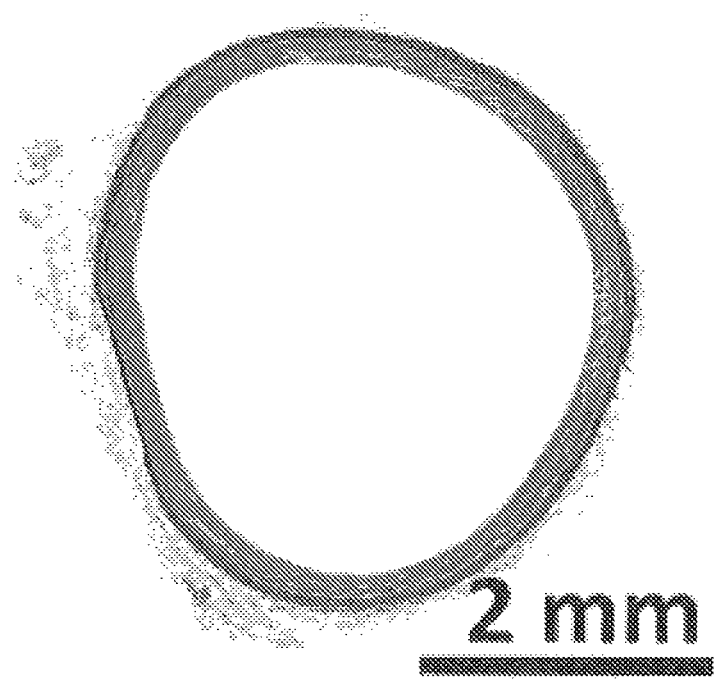
FIG. 52A illustrates 27-day histology results in a porcine left femoral artery for 4 W×2 s×1 s energy treatment.
Figure 52B:
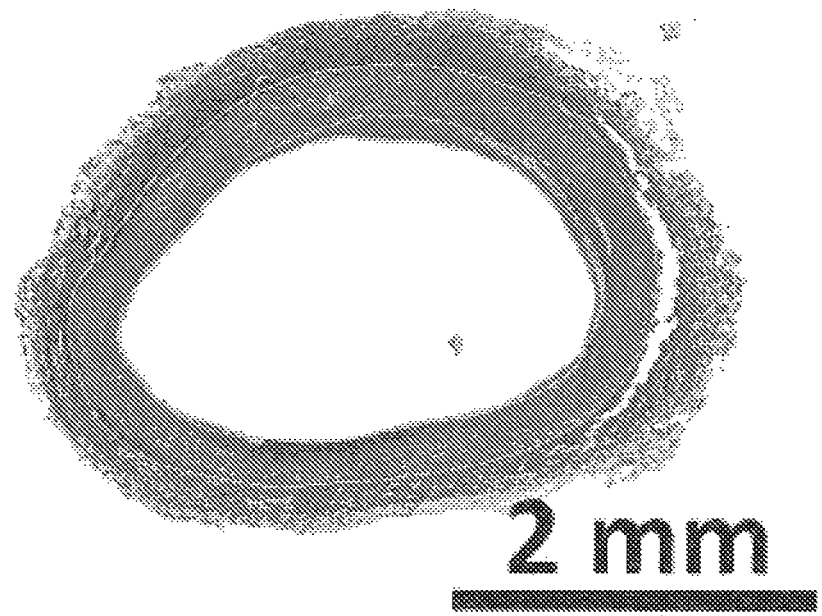
FIG. 52B illustrates 27-day histology results in a porcine left iliac artery for 4 W×2 s×1 s energy treatment.

Poreine animal subjects were treated with the 4×2×1 energy treatment and sacrificed at 27 days. A representative histology sample of the left femoral artery and of the left iliac artery are shown in FIGS. 52A and 52B, respectively. It is observed that luminal patency is maintained after energy treatment in subject vessels, the vessels showing re-endothelialization and no thrombus formation. The greatest observed post-treatment luminal stenosis in response to 4×2×1 energy treatment was approximately 10.6% supporting the conclusion that such treatment may be a preferred means for heating a tissue treatment zone while avoiding subsequent stenosis response in either target or collateral tissues.

2. In-Human

Applying the understanding of preferred energy delivery from preclinical testing, the 4 W×2 s×1 s energy dose (electrodes fired sequentially, full circumference) was applied to a first in human trial under the appropriate procedures and protocols. A pool of patients were selected, each having a significantly restenosed 6 mm×150 mm stent implanted in the superficial femoral artery. Pre-operative assessment of each patient was conducted to verify the degree of in-stent restenosis and any pertinent additional lesion information (for example, the presence of calcification). Each patient received a number of energy treatments based on the length of the stenotic lesion relative to the working length of the balloon-mounted electrodes, wherein a 6 mm diameter balloon was used in for each patient. As is shown in Table 3, percent stenosis is reported as the percentage of the native artery diameter that is reduced by tissue in-growth. A pre-treatment stenosis of 95% would therefore correspond to only 5% of the natural lumen diameter remaining open; the lesser the reported percentage of stenosis, the more favorable the result in terms of restoring normal blood flow through the artery, however, both the percentage reduction in stenosis and the remaining percentage of stenosis may be considered as factors for determining an overall result. The data in Table 3 show a substantial reduction of in-stent restenosis lasting beyond an acute result. As is shown in FIGS. 49A-51C, pre-operative angiograms for each patient as compared to post-operative and 90-day post-operative angiograms demonstrate a substantial restoration of blood flow and an observable removal of the previously present in-stent restenosis. As one of skill in the art will appreciate, diffuse arterial disease in the leg is know to be tenacious, and often present along a significant portion of the diseased artery.

TABLE 3

| Patient Number | Pre-Treatment % Stenosis | Post-Treatment % Stenosis | 90-Day % Stenosis |
| --- | --- | --- | --- |
| 001 | 90-95% | 23-26% | 32% |
| 002 | 66% | 21% | 12% |
| 005 | 55% | 24% | 19% |

Figure 49A:
FIGS. 49A-49C show patient number 001's in-stent restenosis pre-operatively, acutely post-operative, and at 90 days post-operative, respectively.
Figure 49B:
Figure 49C:

Biomechanics of arteries of the leg are known to include pulsatile, bending, torsion, and elongation/foreshortening motions that further complicate treatment options both for initial stenosis treatment and more so for restenosis treatment. Referring now to FIG. 49A, patient number 001's pre-operative condition shows substantial and readily observable narrowing of the artery by in-stent restenosis (shown by arrow markers) along the entire length of the 150 mm stent, with the most highly stenosed location being 90% to 95% reduced from the native artery diameter (shown inside of circled portion). FIGS. 49B and 49C respectively show patient number 001's acute post-operative and 90-day post-operative lumen diameter to be visibly improved throughout the length of the 150 mm stent.

Figure 50A:
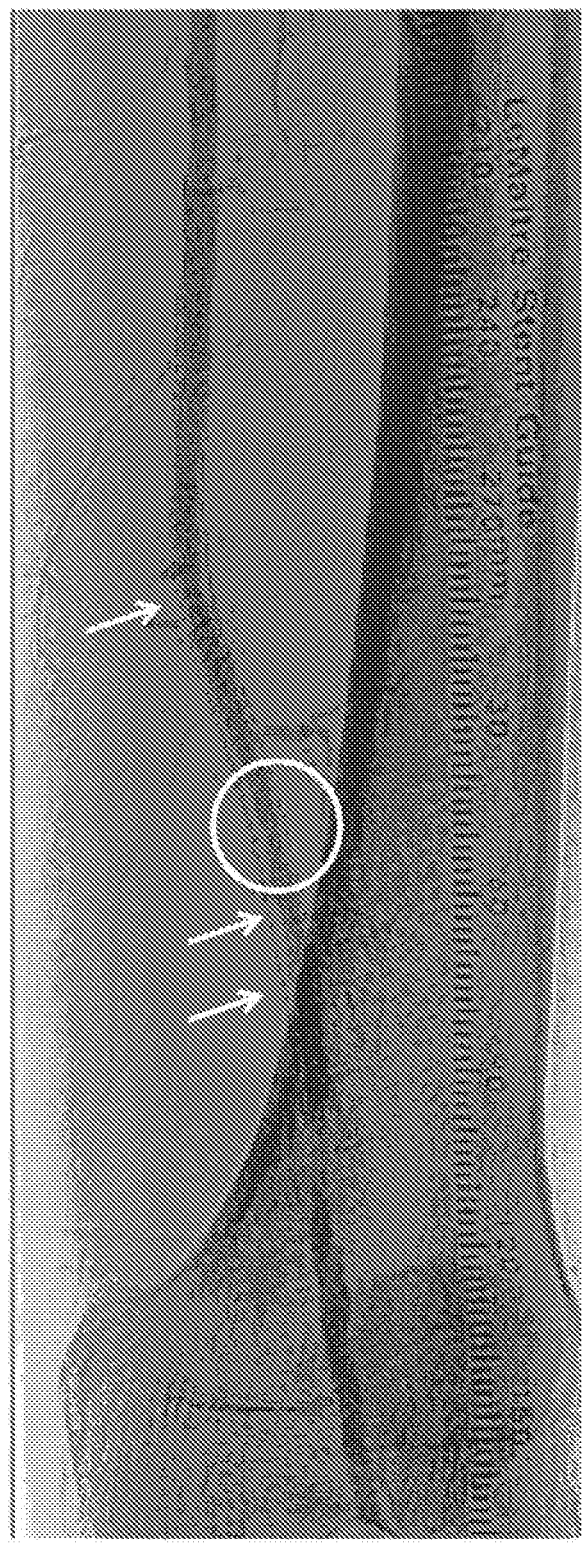
FIGS. 50A-50C show patient number 002's in-stent restenosis pre-operatively, acutely post-operative, and at 90 days post-operative, respectively.
Figure 50B:
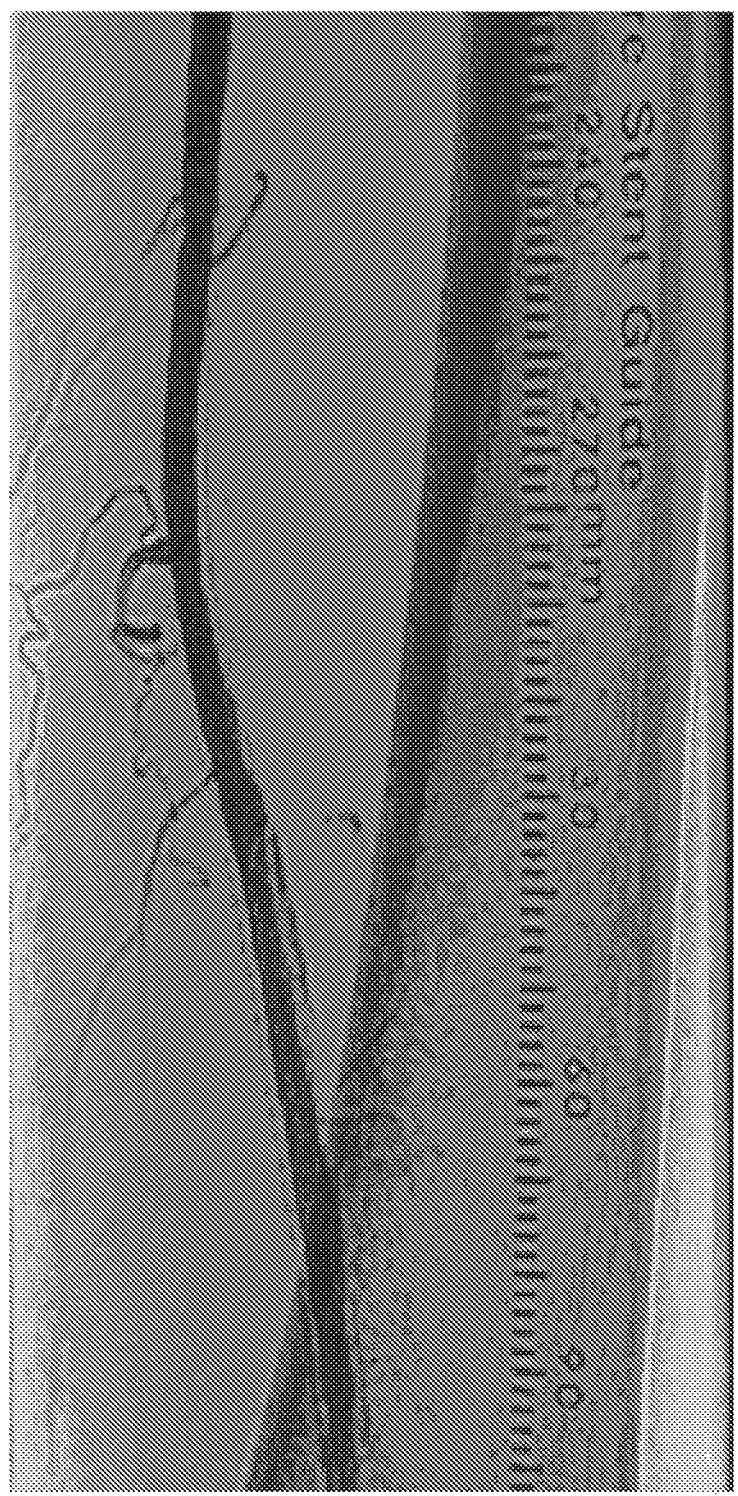
Figure 50C:

As shown in FIG. 50A, patient number 002's most stenosed section is more focal (shown inside of circled portion) than patient number 001's lesions, however, as is common for in-stent restenosis in the leg, diffuse stenosis can be observed along the full length of the 150 mm stent (shown by arrow markers). As seen in FIGS. 50B and 50C respectively, patient number 002's acute post-operative and 90-day post-operative lumen diameter is observably improved.

Figure 51A:
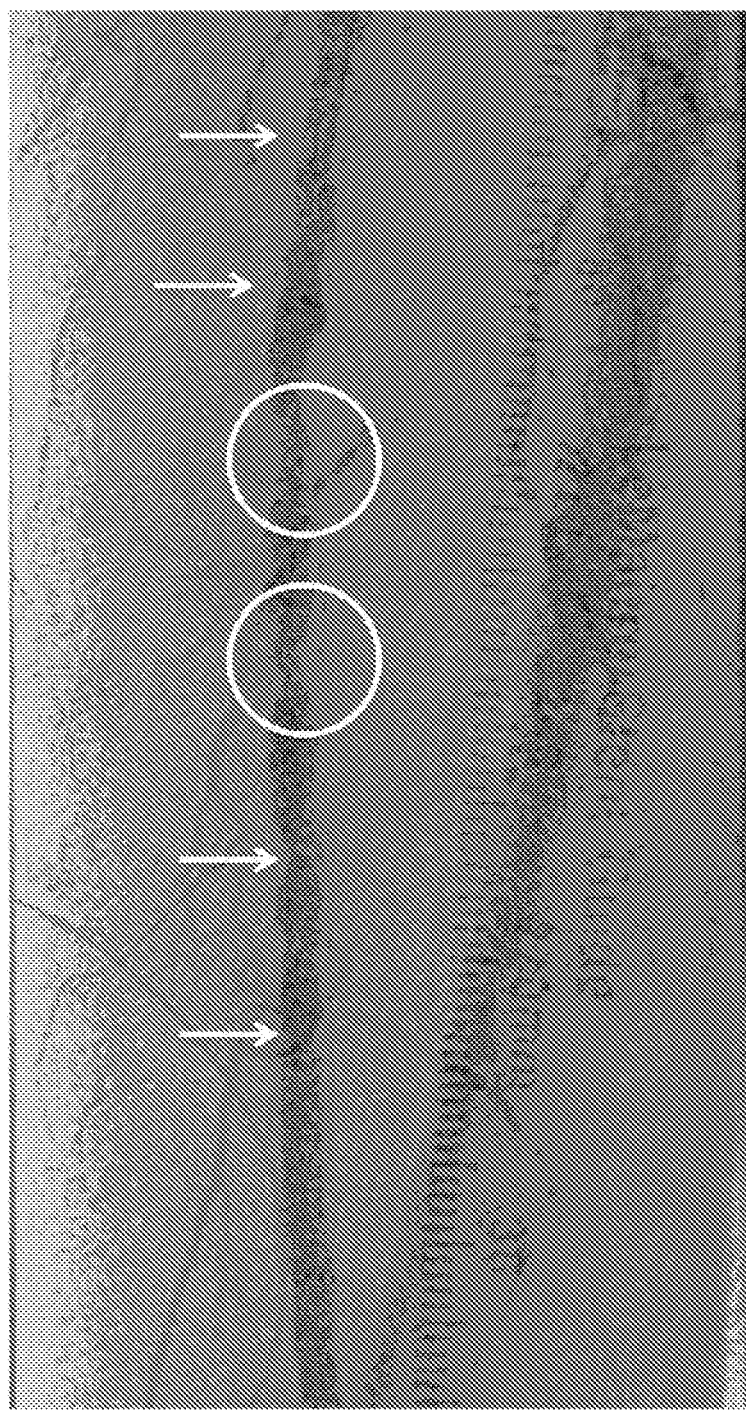
FIGS. 51A-51C show patient number 005's in-stent restenosis pre-operatively, acutely post-operative, and at 90 days post-operative, respectively.
Figure 51B:
Figure 51C:
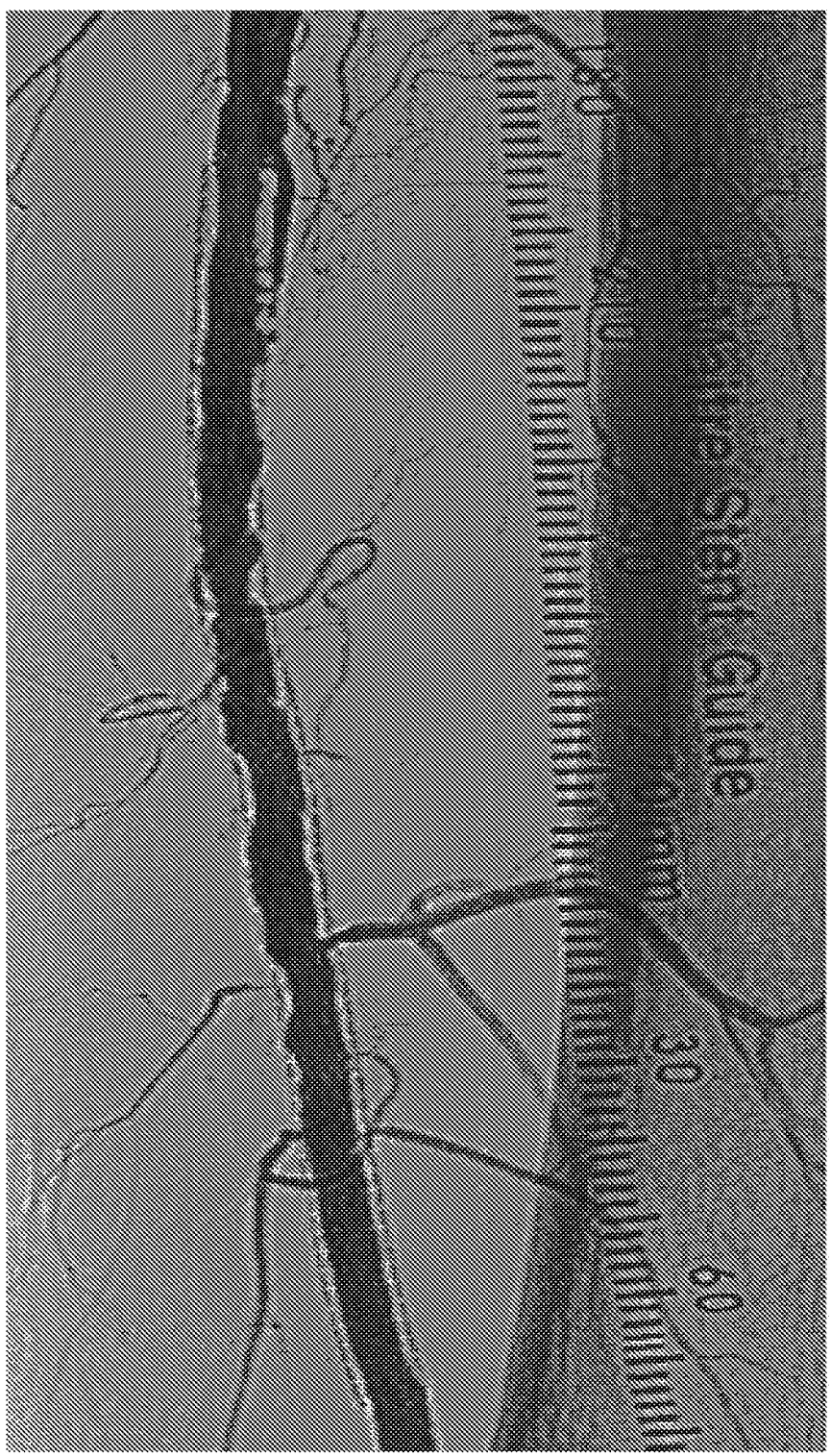

Referring to FIG. 51A, patient number 005 has two focally stenotic sections pre-operatively (shown inside of circled areas), but, similar to patient numbers 001 and 002, has diffuse stenosis throughout most of the length of the 150 mm stent (shown by arrow markers). The acute post-operative and 90-day post-operative lumen diameters shown respectively in FIGS. 51B and 51C again provide readily observable improvement of luminal patency as compared to the pre-operative condition. Table 3 reports the measured changes in stenosis acutely post-operative and at 90 days corresponding to FIGS. 49A-51C.

While the exemplary embodiments have been described in some detail, by way of example and for clarity of understanding, those of skill in the art will recognize that a variety of modifications, adaptations, and changes may be employed.

What is claimed is:

1. A method for delivering energy-based treatment to a wall of a lumen in a patient's body, the method comprising:
positioning a radially expandable structure located at a distal end of an elongate flexible catheter body in the body lumen adjacent to the wall, the catheter body having a longitudinal axis;
expanding the radially expandable structure, such that a plurality of electrodes positioned on the radially expandable structure engage tissue of a portion of the body lumen wall within a treatment zone to complete an electrical circuit that includes a power source, at least one of the plurality of electrodes, and the engaged tissue;
energizing the electrical circuit using the power source; and
controlling the delivery of energy using a processor coupled with the power source based on monitoring feedback from the electrical circuit, such that energy delivered to the treatment zone heats the engaged tissue to a surface temperature of about 55° C. to about 75° C. while tissue collateral to the treatment zone 1 mm from the surface and deeper is heated to less than about 45° C. and such that in response to a change in at least one of frequency range, impedance magnitude, impedance phase angle, temperature, power, voltage, and current, the change being associated with proximity to a metallic implanted structure, energy delivery to the at least one of the plurality of electrodes is modified.

2. The method of claim 1, wherein the expandable structure comprises a balloon.

3. The method of claim 2, wherein the plurality of electrodes positioned on the balloon are included in one or more flex circuits, each flex circuit including a monopolar electrode or a bipolar electrode pair.

4. The method of claim 3, wherein the one or more flex circuits further comprise a temperature sensing structure electrically coupled to the processor so as to provide additional feedback for control by the power source by sensing temperature in proximity to at least one of the plurality of electrodes.

5. The method of claim 1, wherein the processor characterizes engaged tissue within the treatment zone using a tissue signature profile curve, within a frequency range, of impedance magnitude and phase angles of the electrical circuit.

6. The method of claim 5, wherein the processor localizes and characterizes discrete engaged tissue within the treatment zone, and selectively treats the discrete tissue by applying different energy treatments to selected electrodes of the plurality of electrodes.

7. The method of claim 6, wherein the processor selectively energizes an electrode of the plurality of electrodes, and characterizes the discrete tissue to be treated using at least one of a relative slope of the tissue signature profile curves and an offset between the tissue signature profile curves.

8. The method of claim 1, wherein the processor selectively energizes an electrode of the plurality of electrodes, by modulating one or more of power, duty cycle, current, and voltage based on monitoring the feedback from the electrical circuit.

9. A method for treating a body lumen wall, the method comprising:

placing an energy delivery catheter having a distal end including an expandable structure, with a plurality of electrodes thereon, proximate to the body lumen wall;

expanding the expandable structure so as to engage at least one electrode of the plurality of electrodes with tissue of a portion of the body lumen wall within a treatment zone, such that an electrical circuit comprising a power source, the at least one electrode and the tissue is formed; and energizing the electrical circuit so as to apply energy to the treatment zone sufficient to heat the engaged tissue to a surface temperature of about 55° C. to about 75° C. while tissue collateral to the treatment zone 1 mm from the surface and deeper is heated to less than about 45° C. wherein in response to a change in at least one of frequency range, impedance magnitude, impedance phase angle, temperature, power, voltage, and current, the change being associated with proximity to a metallic implanted structure, the energy applied to the at least one of the plurality of electrodes is modified.

10. The method of claim 9, wherein the plurality of electrodes are distributed about a circumference of the expandable structure so as to form an electrode array, the electrodes having an elongate shape oriented to be substantially parallel to a longitudinal axis of the catheter upon expansion of the expandable structure.

11. The method of claim 9, wherein a first group of electrodes of the plurality of electrodes is energized in a sequence that defines a first pattern within the treatment zone, and wherein a second group of electrodes of the plurality of electrodes is energized in a sequence that defines a second pattern within the treatment zone.

12. The method of claim 9, wherein an electrode of the electrical circuit is energized with a power of 0.5 Watts to 20 Watts for 0.5 seconds to 180 seconds.

13. A method for treating a body lumen wall, the method comprising:

placing an energy delivery catheter having a distal end including a balloon with a plurality of energy delivery surfaces thereon proximate to the body lumen wall;

expanding the balloon so as to place one or more of the plurality of energy delivery surfaces in sufficient proximity to tissue of a portion of the body lumen wall within a treatment zone, so as to allow energy to be transferred from the one or more of the plurality of energy delivery surfaces to the tissue; and energizing the one or more of the plurality of energy delivery surfaces with a power source coupled to the energy delivery surfaces so as to apply energy sufficient to heat the tissue to a tissue surface temperature of about 55° C. to about 75° C. while tissue collateral to the treatment zone 1 mm from the surface and deeper is heated to less than about 45° C. wherein the plurality of energy delivery surfaces correspond to a plurality of electrodes, and wherein in response to a change in at least one of frequency range, impedance magnitude, impedance phase angle, temperature, power, voltage, and current, the change being associated with proximity to a metallic implanted structure, the energy applied to at least one of the one or more of the plurality of electrodes is modified.

14. The method of claim 13, wherein the balloon is inflated with an inflation pressure of about 10 atmospheres or less.

15. The method of claim 13, wherein an expanded diameter of the balloon is about 2 mm to about 10 mm.

16. The method of claim 13, wherein the power source includes a radiofrequency generator.

17. The method of claim 13, wherein the body lumen is a blood vessel in a patient's vasculature.

18. The method of claim 17, wherein the blood vessel is a renal artery and the treatment zone includes innervated tissue.

* * * * *